(12) United States Patent
Houser et al.

(10) Patent No.: US 6,740,101 B2
(45) Date of Patent: *May 25, 2004

(54) SUTURELESS ANASTOMOSIS SYSTEMS

(75) Inventors: Russell A. Houser, Livermore, CA (US); James G. Whayne, San Jose, CA (US); Sidney D. Fleischman, Menlo Park, CA (US)

(73) Assignee: Converge Medical, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/329,503

(22) Filed: Jun. 10, 1999

(65) Prior Publication Data

US 2002/0173808 A1 Nov. 21, 2002

Related U.S. Application Data

(60) Provisional application No. 60/088,705, filed on Jun. 10, 1998, and provisional application No. 60/111,948, filed on Dec. 11, 1998.

(51) Int. Cl.[7] ............................................. A61B 17/08
(52) U.S. Cl. ..................................................... 606/153
(58) Field of Search .................. 606/153, 74, 154, 606/155, 156, 157, 158, 151, 191, 194, 228; 439/578, 82, 408; 411/107, 66, 67, 57, 337, 182

(56) References Cited

U.S. PATENT DOCUMENTS 4,214,587 A      7/1980  Sakura, Jr.
4,312,165 A  *  1/1982  Mizusawa .................... 52/511
4,366,819 A      1/1983  Kaster
4,368,736 A      1/1983  Kaster
4,509,890 A  *  4/1985  Hill ............................. 411/337

(List continued on next page.)

FOREIGN PATENT DOCUMENTS

EP      824 901 A2 A3   2/1998
EP        894 475 A1    2/1999

(List continued on next page.)

OTHER PUBLICATIONS

Cragg et al. (1982). "Endovascular diathermic vessel occlusion," *Radiology* 144:303–308.

(List continued on next page.)

*Primary Examiner*—Vy Q. Bui
(74) *Attorney, Agent, or Firm*—Carol M. LaSalle; Bozicevic, Field & Francis LLP

(57) ABSTRACT

Anastomosis systems include fittings and compression mechanisms for effecting end-end or end-side couplings of biological or synthetic bypass grafts to vessel locations. The fittings are tubular and surround end regions of the graft. In some applications an end region of the graft is everted and surrounds an exterior of the fitting, in which case the preferred compression mechanism is a retaining ring. A tool is used to evert the graft end region. In other applications, the fitting has an interior groove that receives an expandable retaining ring that urges the graft end region radially outwardly against the fitting. A graft deploying and securing system includes a needle for puncturing vessel tissue, a dilator, and a sheath adapted for containing a graft/fitting combination and guiding the combination into the vessel through an opening formed by the needle and dilator.

14 Claims, 70 Drawing Sheets

U.S. PATENT DOCUMENTS

| | | | |
|---|---|---|---|
| 4,607,637 A | 8/1986 | Berggren et al. | |
| 4,624,257 A | 11/1986 | Berggren et al. | |
| 4,657,019 A | 4/1987 | Walsh et al. | |
| 4,665,906 A | 5/1987 | Jervis | |
| 4,787,386 A | 11/1988 | Walsh et al. | |
| 4,917,087 A | 4/1990 | Walsh et al. | |
| 4,917,090 A | 4/1990 | Berggren et al. | |
| 4,917,091 A | 4/1990 | Berggren et al. | |
| 4,950,227 A | 8/1990 | Savin et al. | |
| 5,024,608 A * | 6/1991 | Heng et al. | 439/579 |
| 5,067,957 A | 11/1991 | Jervis | |
| 5,078,736 A | 1/1992 | Behl | |
| 5,156,613 A | 10/1992 | Sawyer | |
| 5,190,546 A | 3/1993 | Jervis | |
| 5,234,447 A | 8/1993 | Kaster et al. | |
| 5,259,689 A * | 11/1993 | Arand et al. | 403/337 |
| 5,391,156 A | 2/1995 | Hildwein et al. | |
| 5,405,322 A | 4/1995 | Lennox et al. | |
| 5,423,821 A * | 6/1995 | Pasque | 606/74 |
| 5,443,497 A | 8/1995 | Venbrux | |
| 5,503,635 A | 4/1996 | Sauer et al. | |
| 5,571,167 A | 11/1996 | Maginot | |
| 5,591,226 A | 1/1997 | Trerotola et al. | |
| 5,597,378 A | 1/1997 | Jervis | |
| 5,628,784 A | 5/1997 | Strecker | |
| 5,657,429 A | 8/1997 | Wang et al. | |
| 5,665,117 A | 9/1997 | Rhodes | |
| 5,669,934 A | 9/1997 | Sawyer | |
| 5,676,670 A | 10/1997 | Kim | |
| 5,690,675 A | 11/1997 | Sawyer et al. | |
| 5,695,504 A | 12/1997 | Gifford, III et al. | |
| 5,697,968 A | 12/1997 | Rogers et al. | |
| 5,702,418 A | 12/1997 | Ravenscroft | |
| 5,713,917 A | 2/1998 | Leonhardt et al. | |
| 5,720,755 A | 2/1998 | Dakov | |
| 5,725,544 A | 3/1998 | Rygaard | |
| 5,728,133 A | 3/1998 | Kontos | |
| 5,749,375 A | 5/1998 | Maginot | |
| 5,749,895 A | 5/1998 | Sawyer et al. | |
| 5,755,775 A | 5/1998 | Trerotola et al. | |
| 5,755,778 A | 5/1998 | Kleshinski | |
| 5,762,458 A | 6/1998 | Wang et al. | |
| 5,779,718 A | 7/1998 | Green et al. | |
| 5,797,920 A | 8/1998 | Kim | |
| 5,797,934 A | 8/1998 | Rygaard | |
| 5,810,884 A | 9/1998 | Kim | |
| 5,814,005 A | 9/1998 | Barra et al. | |
| 5,824,015 A | 10/1998 | Sawyer | |
| 5,824,061 A * | 10/1998 | Quijano et al. | 623/1.13 |
| 5,861,003 A | 1/1999 | Latson et al. | |
| 5,868,759 A | 2/1999 | Peyser et al. | |
| 5,868,761 A | 2/1999 | Nicholas et al. | |
| 5,868,770 A | 2/1999 | Rygaard | |
| 5,871,536 A | 2/1999 | Lazarus | |
| 5,931,842 A | 8/1999 | Goldsteen et al. | |
| 5,934,286 A | 8/1999 | Maginot | |
| 5,938,672 A | 8/1999 | Nash | |
| 5,938,696 A | 8/1999 | Goicoechea et al. | |
| 5,944,019 A | 8/1999 | Knudson et al. | |
| 5,944,730 A | 8/1999 | Nobles et al. | |
| 5,944,738 A | 8/1999 | Amplatz et al. | |
| 5,944,750 A | 8/1999 | Tanner et al. | |
| 5,954,735 A | 9/1999 | Rygaard | |
| 5,957,940 A | 9/1999 | Tanner et al. | |
| 5,964,782 A | 10/1999 | Lafontaine et al. | |
| 5,968,053 A | 10/1999 | Revelas | |
| 5,968,089 A | 10/1999 | Krajíček | |
| 5,968,090 A | 10/1999 | Ratcliff et al. | |
| 5,972,017 A | 10/1999 | Berg et al. | |
| 5,972,023 A | 10/1999 | Tanner et al. | |
| 5,976,178 A | 11/1999 | Goldsteen et al. | |
| 5,979,455 A | 11/1999 | Maginot | |
| 5,984,955 A | 11/1999 | Wisselink | |
| 5,989,276 A | 11/1999 | Houser et al. | |
| 5,989,287 A | 11/1999 | Yang et al. | |
| 5,993,468 A | 11/1999 | Rygaard | |
| 6,001,124 A | 12/1999 | Bachinski | |
| 6,004,347 A | 12/1999 | McNamara et al. | |
| 6,007,576 A | 12/1999 | McClellan | |
| 6,010,529 A | 1/2000 | Herweck et al. | |
| 6,017,352 A | 1/2000 | Nash et al. | |
| 6,019,788 A | 2/2000 | Butters et al. | |
| 6,030,370 A | 2/2000 | Kupka et al. | |
| 6,030,392 A | 2/2000 | Dakov | |
| 6,030,395 A | 2/2000 | Nash et al. | |
| 6,036,702 A | 3/2000 | Bachinski et al. | |
| 6,036,703 A | 3/2000 | Evans et al. | |
| 6,036,705 A | 3/2000 | Nash et al. | |
| 6,048,362 A | 4/2000 | Berg | |
| 6,056,762 A | 5/2000 | Nash et al. | |
| 6,059,824 A | 5/2000 | Taheri | |
| 6,063,114 A * | 5/2000 | Nash et al. | 623/1.36 |
| 6,068,654 A | 5/2000 | Berg et al. | |
| 6,071,305 A | 6/2000 | Brown et al. | |
| 6,074,416 A | 6/2000 | Berg et al. | |
| 6,113,612 A | 9/2000 | Swanson et al. | |
| 6,117,147 A | 9/2000 | Simpson et al. | |
| 6,120,432 A | 9/2000 | Sullivan et al. | |
| 6,149,681 A | 11/2000 | Houser et al. | |
| 6,293,955 B1 | 9/2001 | Houser et al. | |

FOREIGN PATENT DOCUMENTS

| | | |
|---|---|---|
| WO | WO 96/22745 | 8/1996 |
| WO | WO 97/13462 | 4/1997 |
| WO | WO 97/13471 | 4/1997 |
| WO | WO 97/16122 A1 | 5/1997 |
| WO | WO 97/27893 | 8/1997 |
| WO | WO 97/27897 | 8/1997 |
| WO | WO 97/27898 | 8/1997 |
| WO | WO 97/31575 A1 | 9/1997 |
| WO | WO 97/40754 A1 | 11/1997 |
| WO | WO 97/43961 | 11/1997 |
| WO | WO 98/03118 | 1/1998 |
| WO | WO 98/06356 | 2/1998 |
| WO | WO 98/07399 | 2/1998 |
| WO | WO 98/08456 | 5/1998 |
| WO | WO 98/19608 | 5/1998 |
| WO | WO 98/19618 | 5/1998 |
| WO | WO 98/19629 | 5/1998 |
| WO | WO 98/19630 | 5/1998 |
| WO | WO 98/19631 | 5/1998 |
| WO | WO 98/19632 | 5/1998 |
| WO | WO 98/19634 | 5/1998 |
| WO | WO 98/19635 | 5/1998 |
| WO | WO 98/19636 A2 | 5/1998 |
| WO | WO 98/19732 | 5/1998 |
| WO | WO 98/19625 A2 A3 | 5/1998 |
| WO | WO 98/38939 | 9/1998 |
| WO | WO 98/38941 | 9/1998 |
| WO | WO 98/40036 A1 | 9/1998 |
| WO | WO 98/42262 A1 | 10/1998 |
| WO | WO 98/52474 A1 | 11/1998 |
| WO | WO 98/55027 A2 | 12/1998 |
| WO | WO 98/57590 | 12/1998 |
| WO | WO 98/57591 | 12/1998 |
| WO | WO 98/57592 | 12/1998 |
| WO | WO99/00055 A2 A3 | 1/1999 |
| WO | WO 99/18887 | 4/1999 |
| WO | WO 99/38454 A2 | 8/1999 |

| | | |
|---|---|---|
| WO | WO 99/45852 A2 | 9/1999 |
| WO | WO 99/48427 A1 | 9/1999 |
| WO | WO 99/62408 | 12/1999 |
| WO | WO 99/62415 | 12/1999 |
| WO | WO 99/63910 A1 | 12/1999 |
| WO | WO 99/65409 A1 | 12/1999 |
| WO | WO 00/09040 | 2/2000 |
| WO | WO 00/15144 A1 | 3/2000 |
| WO | WO 00/24339 | 5/2000 |
| WO | WO 00/27311 A1 | 5/2000 |
| WO | WO 00/27313 A2 A3 | 5/2000 |
| WO | WO 00/40176 A1 | 7/2000 |
| WO | WO 00/53104 A1 | 9/2000 |
| WO | WO 01/41653 A2 A3 | 6/2001 |

OTHER PUBLICATIONS

Gorisch et al. (1982). "Heat–induced contraction of blood vessels," *Lasers in Surgery and Medicine* 2:1–13.

Heijmen et al. (1999). "A novel one–shot anastomotic stapler prototype for coronary bypass grafting on the beating heart: feasibility in the pig," *J. Thorac Cardiovasc. Surg.* 117:117–125.

Yusuf, S. W. et al. (1994). "Transfemoral Endoluminal Repair of Abdominal Aortic Aneurysm with Bifuricated Graft," *Lancet* 344(8923):650–651.

* cited by examiner

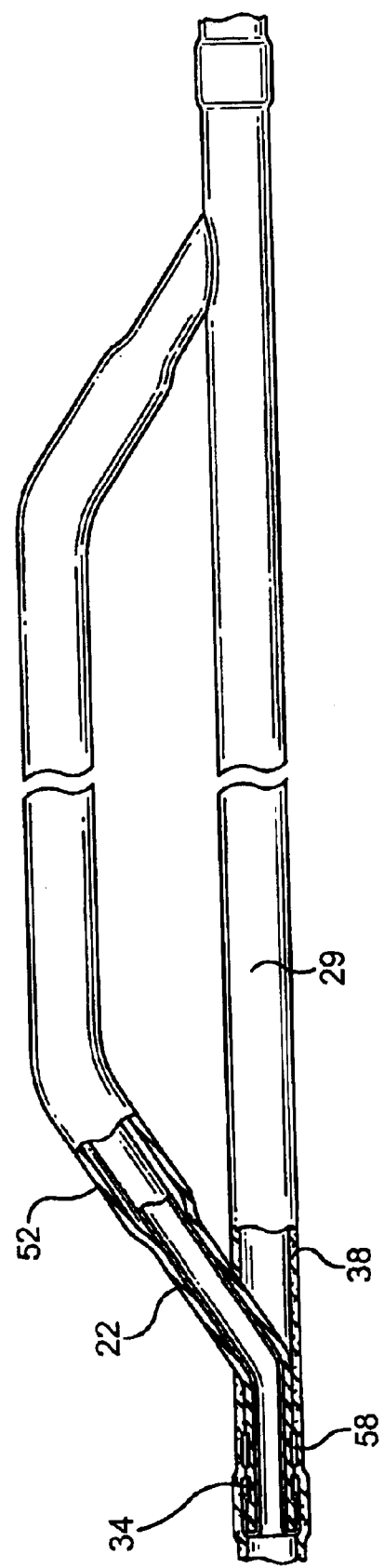

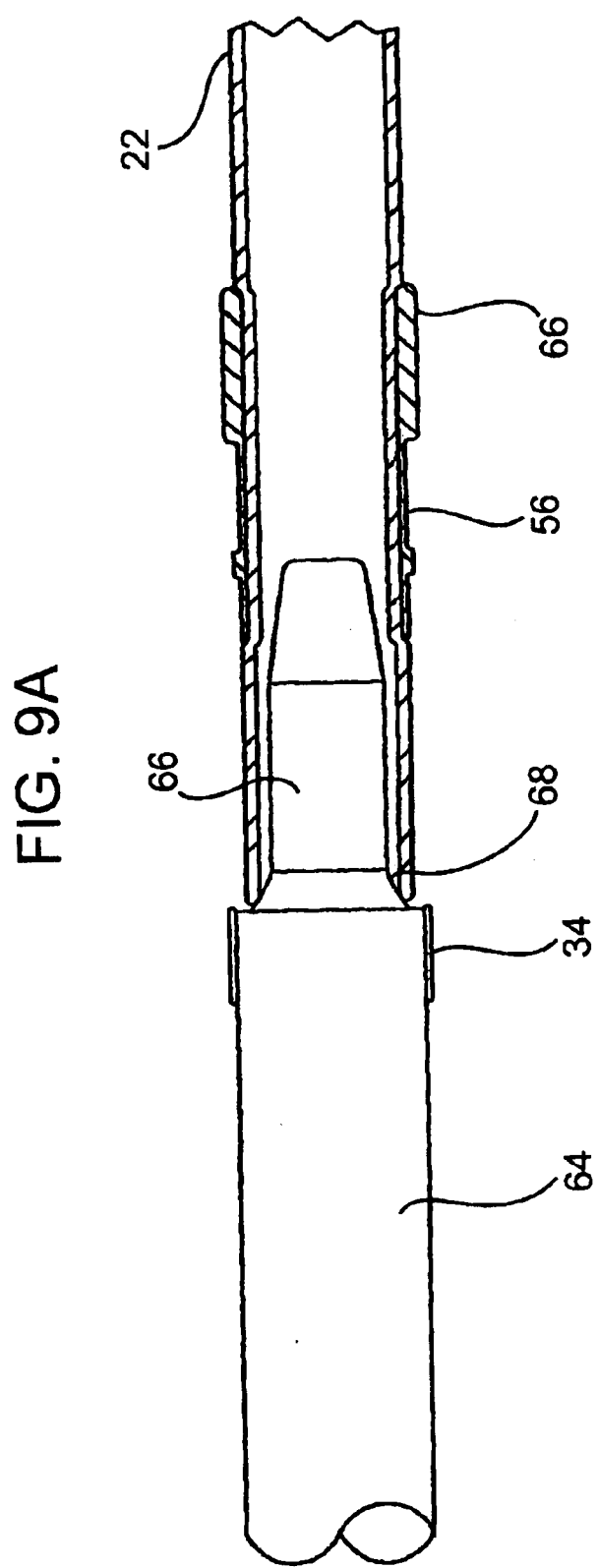

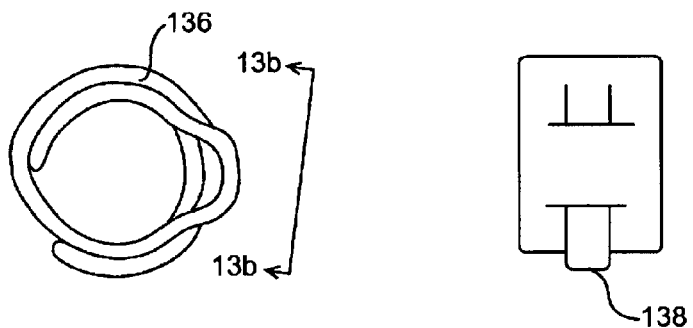
FIG. 12A  FIG. 12B
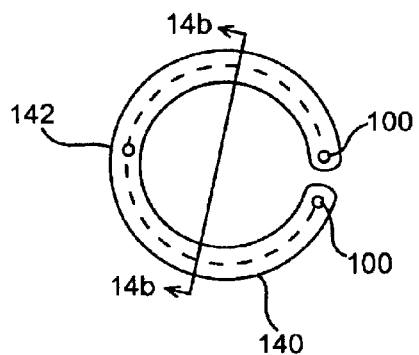
FIG. 13A
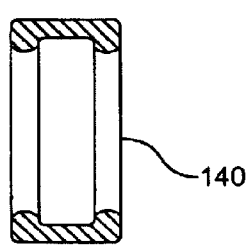 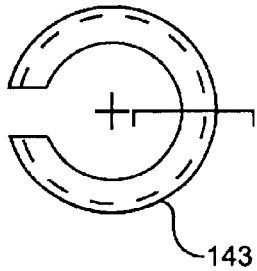 
FIG. 13B  FIG. 13C  FIG. 13D

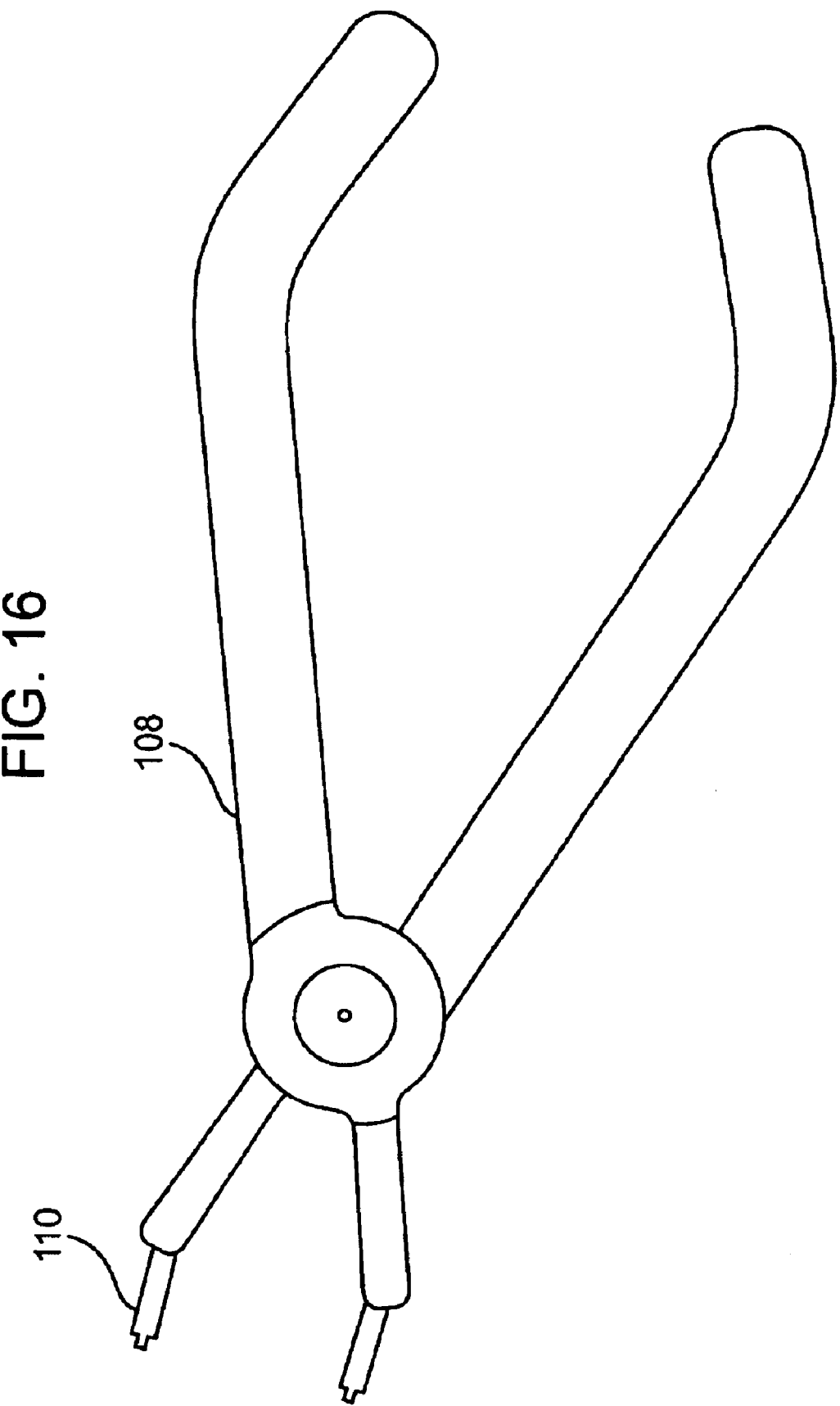

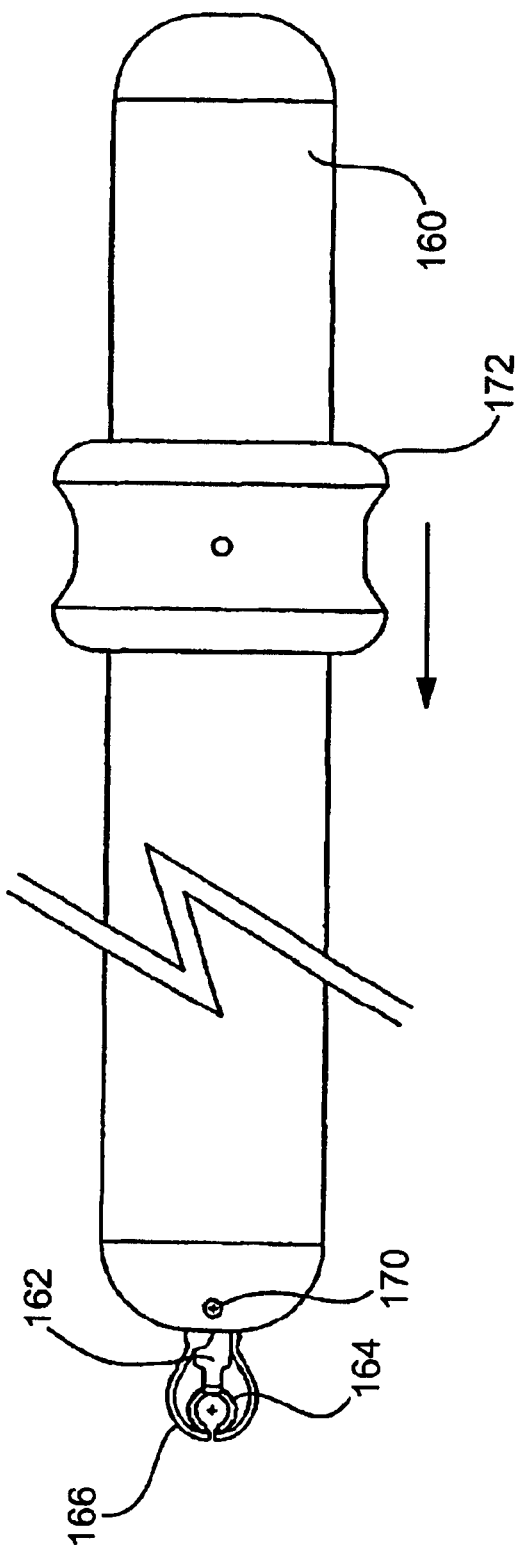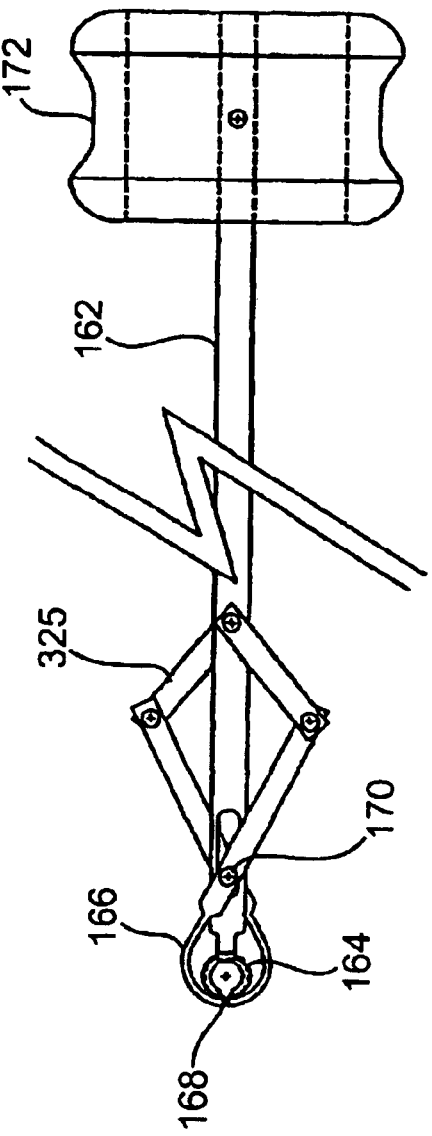
FIG. 17A
FIG. 17B

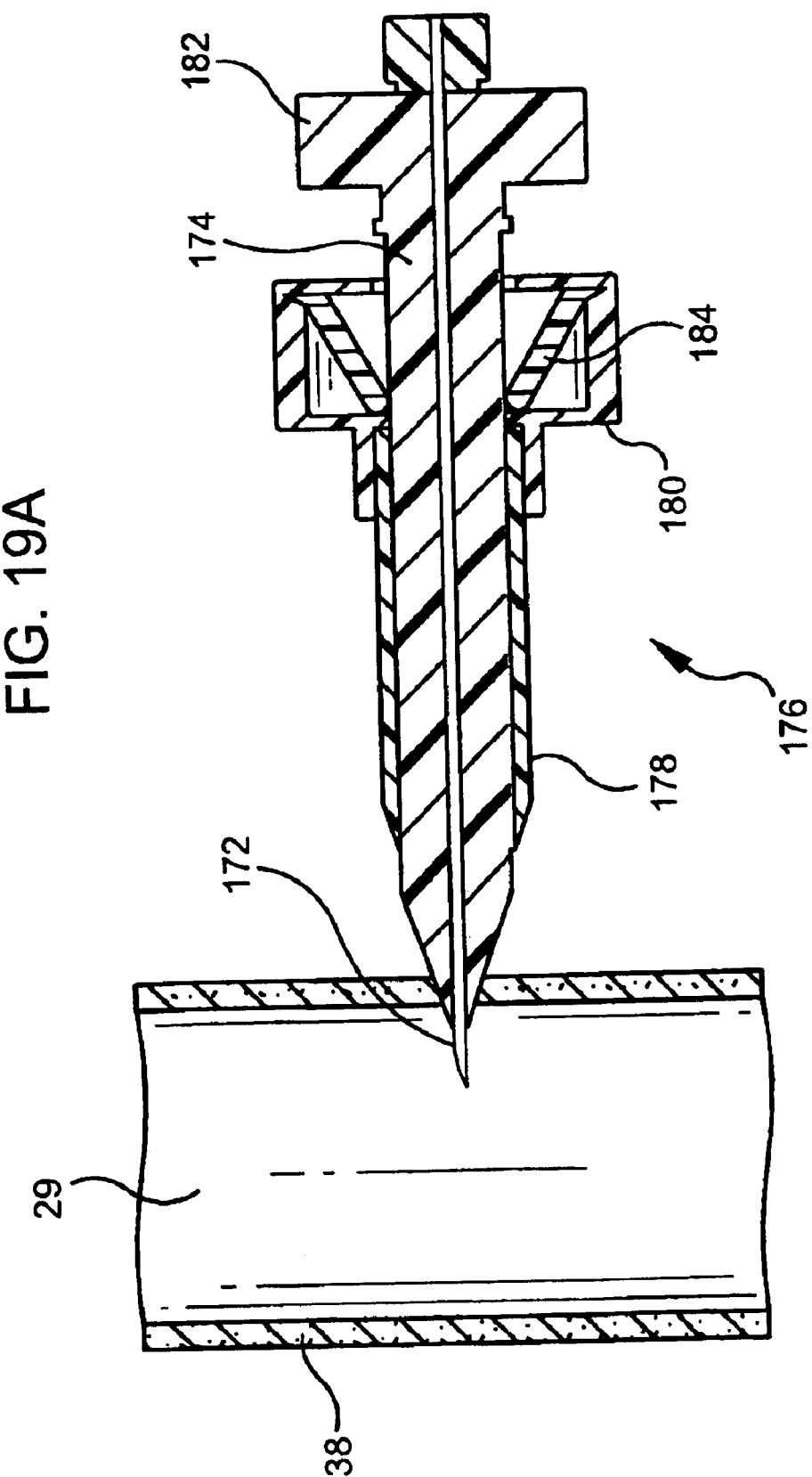

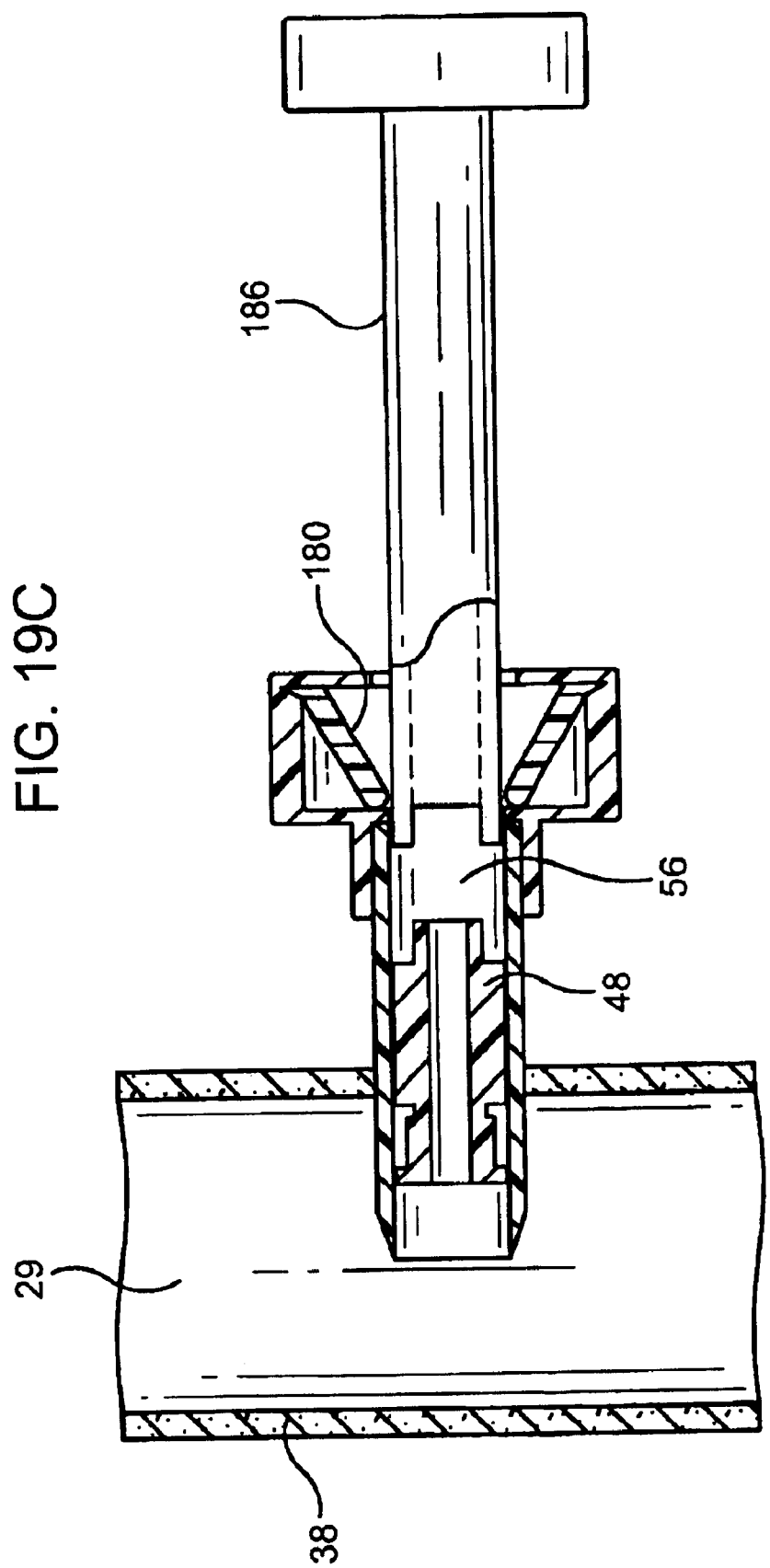

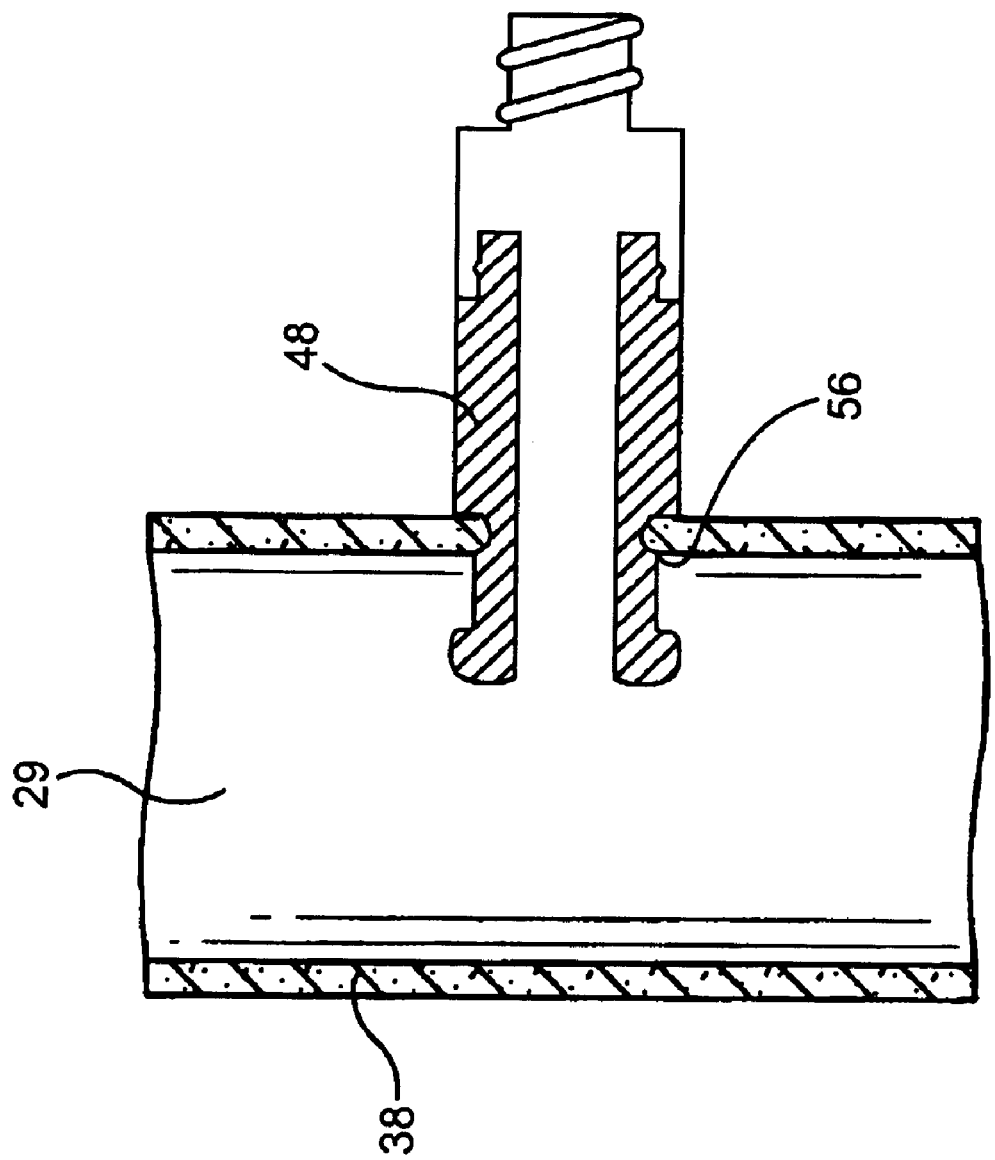

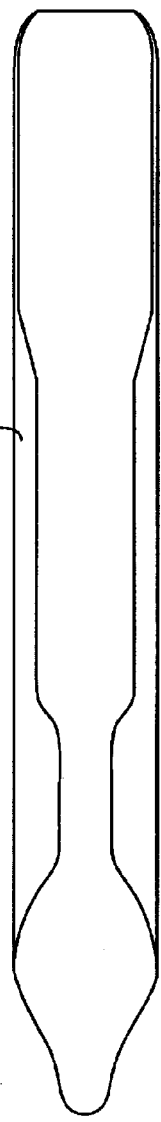
FIG. 29A
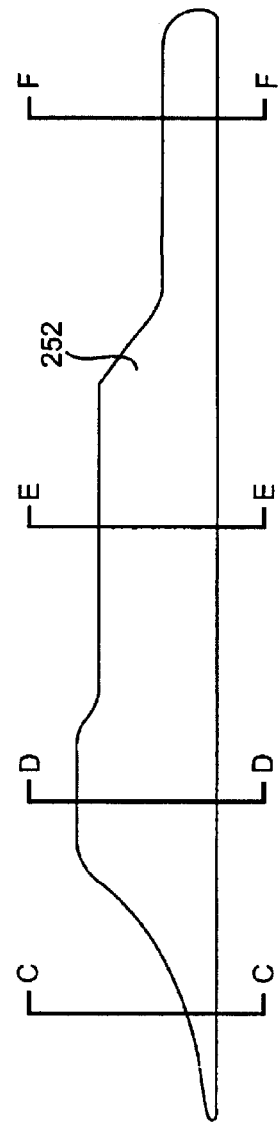
FIG. 29B
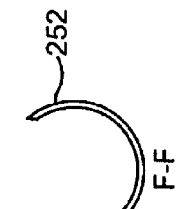
FIG. 29F
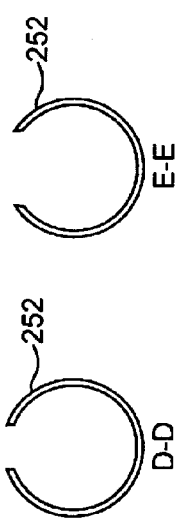
FIG. 29E
FIG. 29D
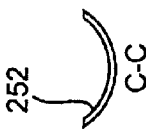
FIG. 29C

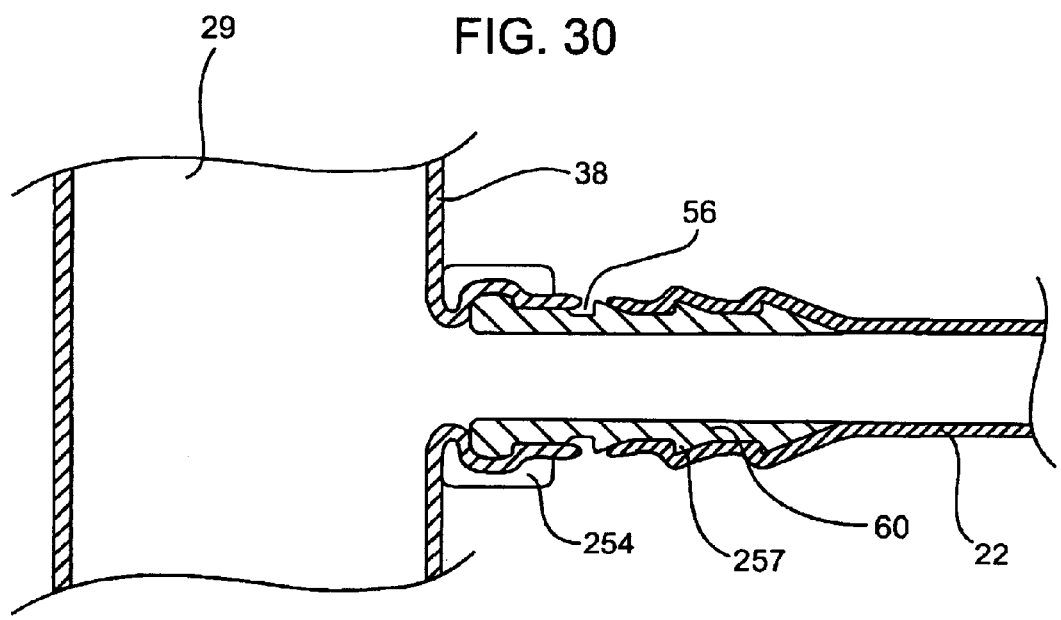

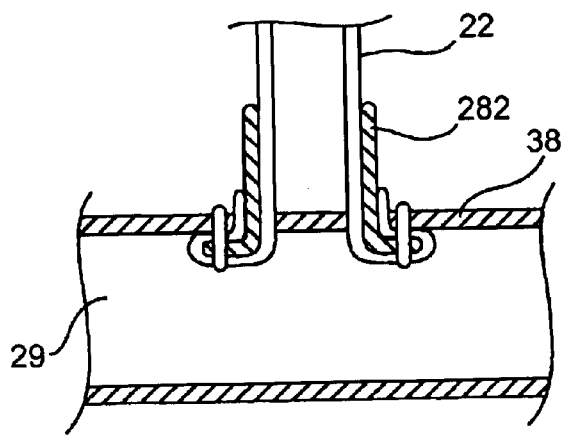
FIG. 34A
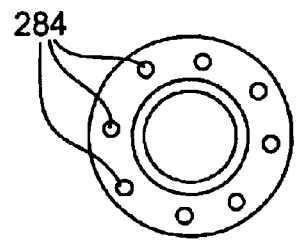
FIG. 34B
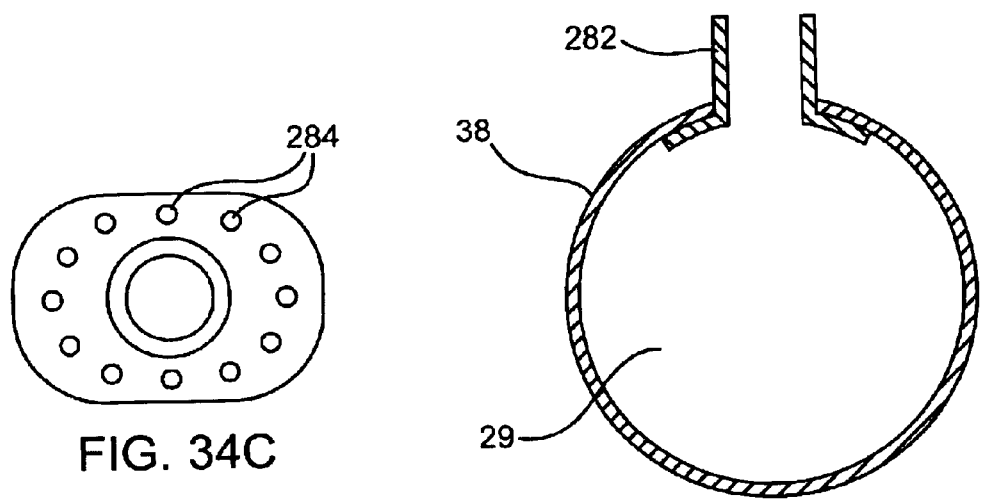
FIG. 34C
FIG. 34D
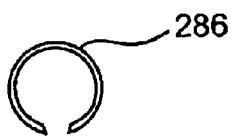
FIG. 35

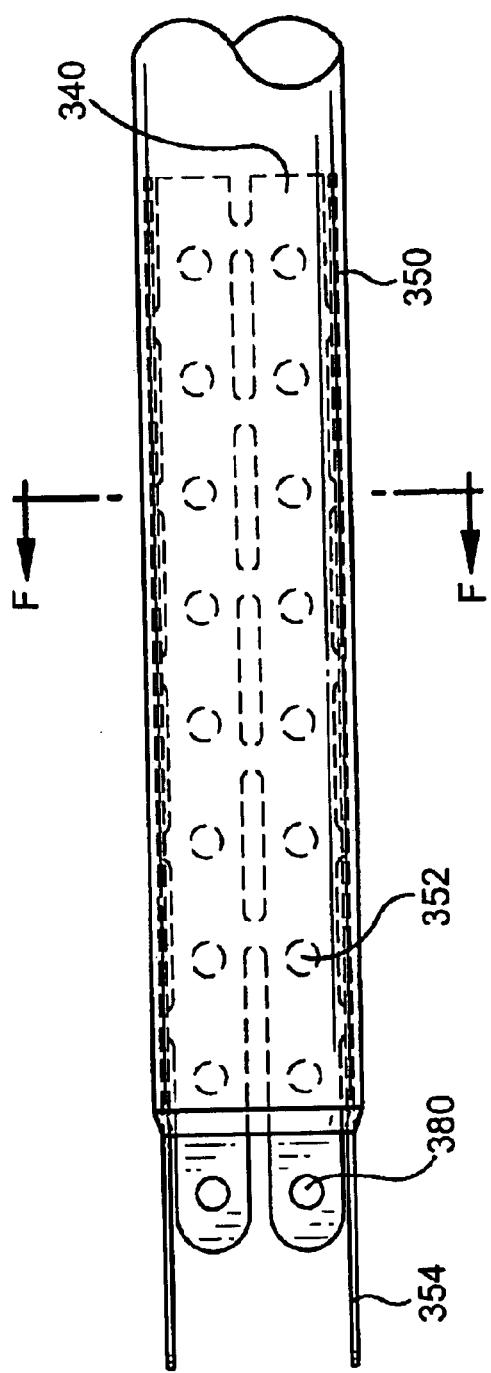
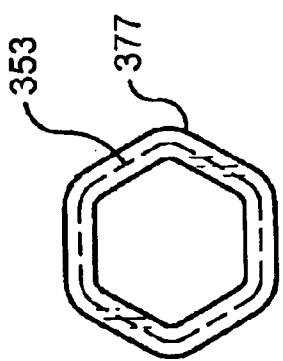
FIG. 41E
FIG. 41F

SUTURELESS ANASTOMOSIS SYSTEMS

This application claims the benefit of Provisional Application No. 60/088,705 entitled "Bypass Graft Mechanical Securing Systems" filed Jun. 10, 1998, and Provisional Application No. 60/111,948 entitled "Bypass Graft Positioning and Securing Systems" filed Dec. 11, 1998.

BACKGROUND OF THE INVENTION

This invention relates to devices for deploying and securing the ends of bypass grafts designed to provide a fluid flow passage between at least two host vessel regions (or other tubular structure regions). More particularly, the invention relates to bypass grafts that are secured at target host vessel locations thereby producing a fluid flow passage from the first host vessel location through the bypass graft and to the second host vessel location. The bypass grafts and deployment systems of the invention do not require stopping or re-routing blood flow to perform an anastomosis between a bypass graft and a host vessel. Accordingly, this invention describes sutureless anastomosis systems that do not require cardiopulmonary bypass support when treating coronary artery disease.

Current techniques for producing anastomoses during coronary artery bypass grafting procedures involve placing the patient on cardiopulmonary bypass support, arresting the heart, and interrupting blood flow to suture, clip, or staple a bypass graft to the coronary artery and aorta; cardiopulmonary bypass support is associated with substantial morbidity and mortality. The embodiments of the invention position and secure bypass grafts at host vessel locations without having to stop or re-route blood flow. Accordingly, the embodiments of the invention do not require cardiopulmonary bypass support and arresting the heart while producing anastomoses to the coronary arteries. In addition, the embodiments of the invention mitigate risks associated with suturing, clipping, or stapling the bypass graft to the host vessel(s), namely bleeding at the attachment sites and collapsing of the vessel around the incision point.

The invention addresses vascular bypass graft treatment regimens requiring end-end anastomoses and end-side anastomoses to attach bypass grafts to host vessels. The scope of the invention includes systems to position and secure bypass grafts used to treat vascular diseases such as atherosclerosis, arteriosclerosis, fistulas, aneurysms, occlusions, and thromboses. In addition, the systems may be used to bypass stented vessel regions that have restenosed or thrombosed. The bypass grafts and delivery systems of the invention are also used to attach the ends of ligated vessels, replace vessels harvested for bypass grafting procedures (e.g. radial artery), and re-establish blood flow to branching vessels which would otherwise be occluded during surgical grafting procedures (e.g. the renal arteries during abdominal aortic aneurysm treatment). In addition, the invention addresses other applications such as, but not limited to, producing arterial to venous shunts for hemodialysis patients, bypassing lesions and scar tissue located in the fallopian tubes causing infertility, attaching the ureter to the kidneys during transplants, and bypassing gastrointestinal defects (occlusions, ulcers).

DESCRIPTION OF THE RELATED ART

Stenosed blood vessels cause ischemia potentially leading to tissue infarction. Conventional techniques to treat partially or completely occluded vessels include balloon angioplasty, stent deployment, atherectomy, and bypass grafting.

Coronary artery bypass grafting (CABG) procedures to treat coronary artery disease have traditionally been performed through a thoracotomy with the patient placed on cardiopulmonary bypass support and using cardioplegia to induce cardiac arrest. Cardiac protection is required when performing bypass grafting procedures having prolonged ischemia times. Current bypass grafting procedures involve interrupting blood flow to suture or staple the bypass graft to the host vessel wall and create the anastomoses. When suturing, clipping, or stapling the bypass graft to the host vessel wall, a large incision is made through the host vessel and the bypass graft is sewn to the host vessel wall such that the endothelial layers of the bypass graft and vessel face each other. Bypass graft intima to host vessel intima apposition reduces the incidence of thrombosis associated with biological reactions that result from blood contacting the epithelial layer of a harvested bypass graft. This is especially relevant when using harvested vessels that have a small inner diameter (e.g. 2 mm).

Less invasive attempts for positioning bypass grafts at target vessel locations have used small ports to access the anatomy. These approaches use endoscopic visualization and modified surgical instruments (e.g. clamps, scissors, scalpels, etc.) to position and suture the ends of the bypass graft at the host vessel locations. Attempts to eliminate the need for cardiopulmonary bypass support while performing CABG procedures have benefited from devices that stabilize the motion of the heart, retractors that temporarily occlude blood flow through the host vessel, and shunts that re-route the blood flow around the anastomosis site. Stabilizers and retractors still require significant time and complexity to expose the host vessel and suture the bypass graft to the host vessel wall. Shunts not only add to the complexity and length of the procedure, but they require a secondary procedure to close the insertion sites proximal and distal to the anastomosis site.

Attempts to automate formation of sutureless anastomoses have led to mechanical stapling devices. Mechanical stapling devices have been proposed for creating end-end anastomoses between the open ends of transected vessels. Berggren, et al propose an automatic stapling device for use in microsurgery (U.S. Pat. Nos. 4,607,637; 4,624,257; 4,917,090; 4,917,091). This stapling device has mating sections containing pins that are locked together after the vessel ends are fed through lumens in the sections and everted over the pins. This stapling device maintains intima to intima apposition for the severed vessel ends but has a large profile and requires impaling the everted vessel wall with the pins. Sakura describes a mechanical end-end stapling device designed to reattach severed vessels (U.S. Pat. No. 4,214,587). This device has a wire wound into a zig-zag pattern to permit radial motion and contains pins bonded to the wire that are used to penetrate tissue. One vessel end is everted over and secured to the pins of the end-end stapling device, and the other vessel end is advanced over the end-end stapling device and attached with the pins. Sauer, et al proposes another mechanical end-end device that inserts mating pieces into each open end of a severed vessel (U.S. Pat. No. 5,503,635). Once positioned, the mating pieces snap together thereby bonding the vessel ends. These end-end devices are amenable to reattaching severed vessels but are not suitable to producing end-end anastomoses between a bypass graft and an intact vessel, especially when exposure to the vessel is limited.

Mechanical stapling devices have also been proposed for end-side anastomoses. These devices are designed to insert bypass grafts, attached to the mechanical devices, into the host vessel through a large incision and secure the bypass graft to the host vessel. Kaster describes vascular stapling apparatus for producing end-side anastomoses (U.S. Pat. Nos. 4,366,819; 4,368,736; and 5,234,447). Kaster's end-side apparatus is inserted through a large incision in the host vessel wall. The apparatus has an inner flange that is placed against the interior of the vessel wall, and a locking ring that is affixed to the fitting and contains spikes that penetrate into the vessel thereby securing the apparatus to the vessel wall. The bypass graft is itself secured to the apparatus in the everted or non-everted position through the use of spikes incorporated in the apparatus design.

U.S. Surgical has developed automatic clip appliers that replace suture stitches with clips (U.S. Pat. Nos. 5,868,761; 5,868,759; 5,779,718). These clipping devices have been demonstrated to reduce the time required when producing the anastomosis but still involve making a large incision through the host vessel wall. As a result, blood flow through the host vessel must be interrupted while creating the anastomoses.

Gifford, et al provides end-side stapling devices (U.S. Pat. No. 5,695,504) that secure harvested vessels to host vessel walls maintaining intima to intima apposition. This stapling device is also inserted through a large incision in the host vessel wall and uses staples incorporated in the device to penetrate into tissue and secure the bypass graft to the host vessel.

Walsh, et al propose a similar end-side stapling device (U.S. Pat. Nos. 4,657,019; 4,787,386; 4,917,087). This end-side device has a ring with tissue piercing pins. The bypass graft is everted over the ring; then, the pins penetrate the bypass graft thereby securing the bypass graft to the ring. The ring is inserted through a large incision created in the host vessel wall and the tissue piercing pins are used to puncture the host vessel wall. A clip is then used to prevent dislodgment of the ring relative to the host vessel.

The end-side stapling devices previously described require insertion through a large incision, which dictates that blood flow through the host vessel must be interrupted during the process. Even though these and other clipping and stapling end-side anastomotic devices have been designed to decrease the time required to create the anastomosis, interruption of blood flow through the host vessel increases the morbidity and mortality of bypass grafting procedures, especially during beating heart CABG procedures. A recent experimental study of the U.S. Surgical One-Shot anastomotic clip applier observed abrupt ventricular fibrillation during four of fourteen internal thoracic artery to left anterior descending artery anastomoses in part due to coronary occlusion times exceeding 90 seconds (Heijmen, et al. A novel one-shot anastomotic stapler prototype for coronary bypass grafting on the beating heart: feasibility in the pig. *J Thorac Cardiovasc Surg.* 117:117–25; 1999).

A need thus exists for bypass grafts and delivery systems that are capable of quickly producing an anastomosis between a bypass graft and a host vessel wall without having to stop or re-route blood flow. These anastomoses must withstand the pressure exerted by the pumping heart and ensure blood does not leak from the anastomoses into the thoracic cavity, abdominal cavity, or other region exterior to the vessel wall.

SUMMARY OF THE INVENTION

The embodiments of the present invention provide sutureless anastomosis systems that enable a physician to quickly and accurately secure a bypass graft to a host vessel or other tubular body structure. In addition, the invention enables the physician to ensure bypass graft stability, and prevent leaking at the vessel attachment points. The delivery systems of the invention do not require stopping or re-routing blood flow while producing the anastomosis; current techniques require interrupting blood flow to suture, clip, or staple a bypass graft to the host vessel wall.

One aspect of the invention provides fittings designed to exert radial force at the vessel attachment points to maintain bypass graft patency. The fittings may be used to secure biological bypass grafts obtained by harvesting vessels from the patient or synthetic bypass graft materials. When using harvested vessels, fitting embodiments permit everting the harvested vessel to maintain intima to intima apposition between the bypass graft and the host vessel. When using synthetic bypass graft materials, the fittings may be incorporated in the bypass graft design to eliminate the step of attaching the bypass graft to the fitting prior to deploying the bypass graft. The fittings, with bypass grafts attached, are advanced through the delivery system and are secured to the host vessel wall at target locations.

The delivery systems enable inserting the fitting and bypass graft into the host vessel without having to interrupt blood flow through the host vessel. One delivery system embodiment is a combination of tear-away sheath, dilator, guidewire, and needle designed to be inserted into the host vessel at the desired anastomosis site. After attaching the bypass graft to the host vessel, the hub and valve of the tear-away sheath are configured to split so the entire sheath may be separated and removed from around the bypass graft. This facilitates attaching both ends of the bypass graft using the delivery system of the invention and removing the tear-away sheath from around the intact bypass graft. A plunger is used to insert the bypass graft and fitting combination through the sheath and into the host vessel. The plunger also protects the bypass graft during insertion into the host vessel, especially when advancing past the hemostatic valve. As described in co-pending U.S. application Ser. No. 08/966,003 filed Nov. 7, 1997, the dilator and needle may incorporate advanced features, such as steering, sensing, and imaging, used to facilitate placing and locating the bypass graft and fitting combination.

An alternative delivery system involves advancing a fitting embodiment through a puncture in the host vessel wall without the need to stop or re-route blood flow. The fitting may be partially inserted through an incision and rotated past the host vessel wall and into the interior of the host vessel. Additionally, a guidewire may serve as a passage to rotate and advance the fitting into the interior of the host vessel. Once inside the host vessel, the fitting may be secured thereby securing the bypass graft to the host vessel.

In accordance with the invention, fitting embodiments produce anastomoses between harvested vessels and host vessels such that only the endothelial layer of the bypass graft is exposed to blood flow. The invention also describes fittings designed to permit retrograde flow past the anastomosis site so as to maintain flow through the lesion and to branching vessels located proximal to the anastomosis site. A further aspect of the invention provides fittings having branches to accommodate multiple bypass grafts using a single proximal anastomosis.

Further features and advantages of the inventions will be elaborated in the detailed description and accompanying drawings.

BRIEF DESCRIPTION OF DRAWINGS

FIGS. 9a to c show an everting tool;

FIGS. 12a and b show a retaining ring in accordance with an embodiment of the invention;

FIGS. 13a and b show a retaining ring in accordance with an embodiment of the invention;

FIGS. 13c and d show an alternative expandable, collapsible retaining ring used with bypass graft fittings;

FIG. 16 shows an expanding tool used to position retaining rings having eyelets;

FIGS. 17a to c show an expanding tool used to open the diameter of and position the retaining ring shown in FIGS. 13c and d;

FIGS. 19a to d show a delivery system in accordance with an embodiment of the invention;

FIGS. 29a to f show an introduction device used to deploy the bypass graft and fitting combination through an incision in the vessel wall;

FIG. 30 is a cross-sectional view of a bypass graft and fitting combination attached to a vessel wall in accordance with an embodiment of the invention;

FIGS. 34a to d show a fitting incorporating flanges to secure a bypass graft to a host vessel wall;

FIG. 35 is an end view of a clip used instead of sutures to attach the flanges;

FIGS. 41a to h show radially expandable, collapsible end-side fittings;

DETAILED DESCRIPTION OF PREFERRED EMBODIMENT

The fittings and delivery systems of the invention are intended to produce anastomoses between bypass grafts and host vessels to treat vascular abnormalities such as stenoses, thromboses, other occlusions, aneurysms, fistulas, or other indications requiring a bypass graft. The systems of the invention are useful in bypassing stented vessels that have restenosed. Current approaches for treating stenosed stents have not been successful at safely and reliably removing the lesion and opening the vessel lumen. Therefore the approach described by this invention, which produces a blood flow conduit around the stented lesion, mitigates concerns associated with damaging the stent or forming emboli while removing deposits attached to the stent. The fittings are also intended to secure and support the ends of transected vessels such as those cut during organ transplantations. The embodiments of the invention also provide mechanisms to secure branching vessels to a replacement graft during surgical procedures in which the branching vessels would otherwise be occluded from blood flow (e.g. reattaching the renal arteries, mesenteric artery, celiac artery, and intercostal arteries during treatment of abdominal aortic aneurysms that are pararenal, suprarenal, or thoracoabdominal in classification).

Figure 1:
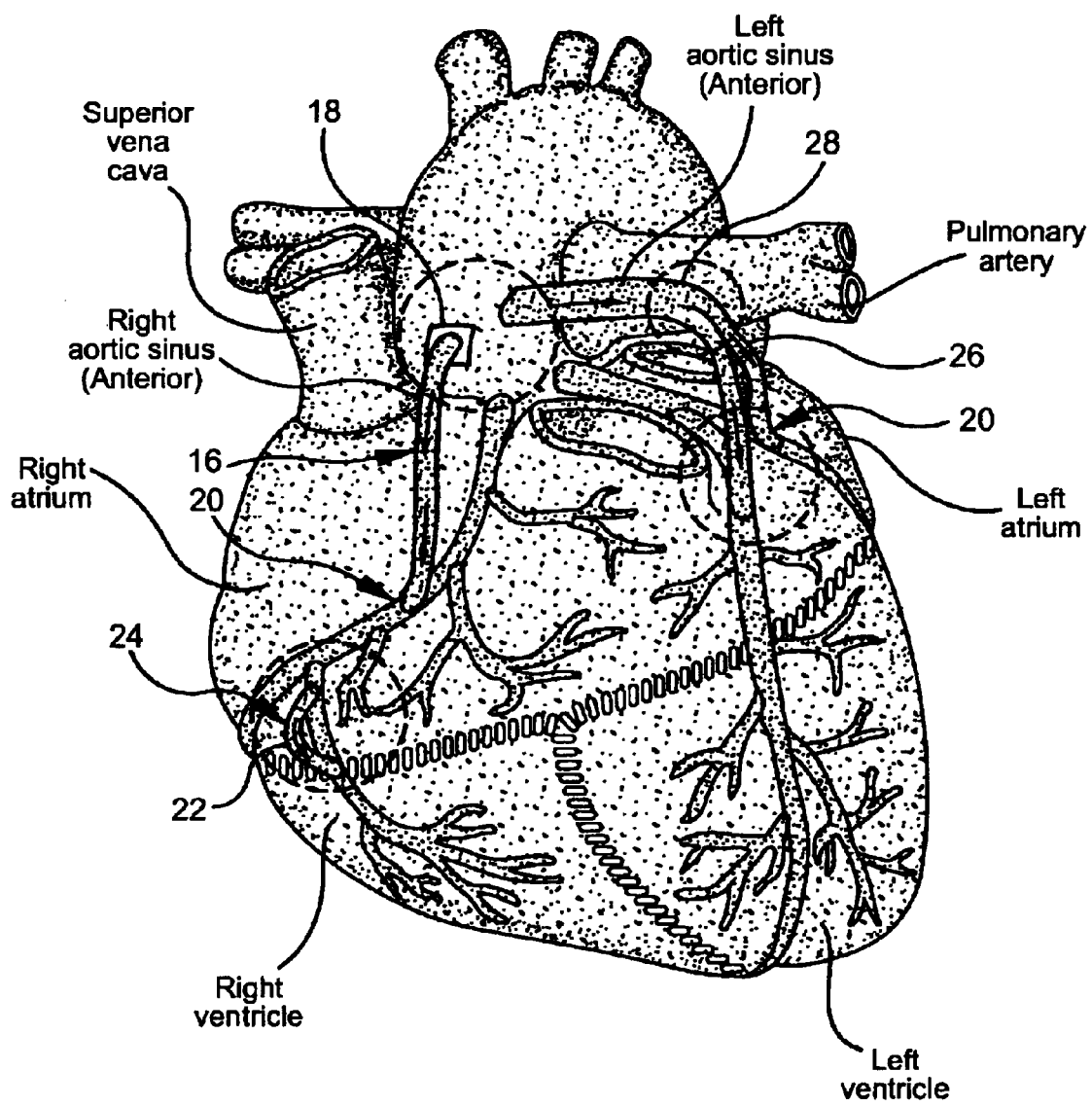
FIG. 1 shows a heart containing multiple bypass grafts positioned and secured to the host vessels.

Referring more particularly to the drawings there is seen, in FIG. 1, bypass grafts secured to host vessels during coronary artery bypass grafting (CABG) procedures. Bypass graft 16 provides a blood flow passage from the aorta to the right coronary artery. An end-side fitting 18 is used to secure the proximal end of the bypass graft 16 to the aorta. A fitting 20 (end-side or end-end) is used to secure the distal end of the bypass graft to the right coronary artery. An in-line bypass graft 22 provides a blood flow passage along a small or medium sized vessel, such as a coronary artery, by securing the bypass graft to the host vessel with end-end fittings 24 configured to shunt blood flow around a diseased section of the host vessel. A bypass graft 26 is secured to the aorta with an end-side fitting and branches at 28, into several distinct bypass grafts which are further secured to the left anterior descending artery and circumflex artery using end-end or end-side fittings 20. The specific bypass grafts and fittings in these examples demonstrate representative applications for the fittings and should not limit the scope of use for the embodiments of the invention. However, it should be noted that the combination of graft fittings (end-side and end-end) used to secure a bypass graft to a host vessel, along a host vessel, or between host vessels depends on the application.

Bypass Grafts

The bypass graft may be a synthetic graft material, harvested vessel, or other tubular body structure, depending on the indication for use. The harvested vessels may be an internal mammary artery, mesenteric artery, radial artery, saphenous vein or other body tubing. Harvested vessels may be dissected using newer minimally invasive, catheter-based techniques or standard surgical approaches. Fittings in accordance with the invention are designed to attach bypass grafts to host vessels (or other tubular structures). The fittings used to position and attach such bypass grafts are extensions of the collet and grommet embodiments described in U.S. application Ser. No. 08/966,003 filed Nov. 7, 1997 and incorporated herein by reference. The primary advantage of biological bypass grafts (e.g. harvested vessels) over currently available synthetic materials is the reduction in thrombosis especially when using small diameter (e.g. (2 mm) bypass grafts. However, the fittings and delivery systems of the invention are equally effective at positioning and securing all types of bypass grafts, biological and synthetic.

Synthetic bypass grafts may be manufactured by extruding, injection molding, weaving, braiding, or dipping polymers such as PTFE, expanded PTFE, urethane, polyamide, polyimide, nylon, silicone, polyethylene, collagen, polyester, composites of these representative materials, or other suitable graft material. These materials may be fabricated into a sheet or tubing using one or a combination of the stated manufacturing processes. The sides of sheet materials may be bonded using radiofrequency energy, laser welding, ultrasonic welding, thermal bonding, sewing, adhesives, or a combination of these processes to form tubing. The synthetic bypass graft may be coated, deposited, or impregnated with materials, such as paralyne, heparin solutions, hydrophilic solutions, or other substances designed to reduce thrombosis or mitigate other risks that potentially decrease the patency of synthetic bypass grafts.

The primary advantage of synthetic bypass graft materials is the ability to bond the bypass graft to the fittings prior to starting the procedure or incorporate the fittings into the bypass graft by injection molding or other manufacturing process. Currently, synthetic bypass grafts are indicated for blood vessels having medium and large diameters (e.g. >3 mm), such as peripheral vessels, tubular structures such as the fallopian tubes, or shunts for hemodialysis. However, medical device manufacturers such as Possis Medical, Inc. and Thoratec Laboratories, Inc. are evaluating synthetic bypass grafts for coronary indications. In this disclosure and the accompanying drawings, reference to bypass graft may pertain to either biological bypass grafts such as harvested vessels or synthetic bypass grafts, unless specifically stated.

As discussed in co-pending U.S. application Ser. No. 08/932,566 filed Sep. 19, 1997 and co-pending U.S. application Ser. No. 08/966,003 filed Nov. 7, 1997, support members may be incorporated into the graft. When using synthetic bypass grafts, the support members may be laminated between layers of graft material. The synthetic bypass graft encompassing support members may be fabricated by extruding, spraying, injection molding, or dipping a primary layer of graft material over a removable mandrel; positioning, winding or braiding the support members on the primary layer; and extruding, spraying, injection molding, or dipping a secondary layer over the graft material/support member combination. The support members may be fabricated from a metal, alloy (e.g. stainless steel), or polymer (e.g. nylon or polyester); however, the support members preferably have a shape memory. Support members enhance the performance of the bypass graft by maintaining lumenal patency, offering flexibility, and increasing the strength. Support members fabricated from memory elastic alloys, such as nickel titanium, exhibiting stress-induced martensite characteristics further reinforce the bypass graft and/or vessel wall and prevent permanent deforming upon exposure to external forces.

Alternatively, synthetic bypass grafts incorporating support members may be fabricated using cellulosic materials such as regenerated cellulose or cellulose acetate. Cellulosic materials may be extruded, wrapped, injection molded, or dipped to laminate the support members between graft material layers. Cellulosics, and other such materials that have a high water adsorption rate, are relatively stiff when dehydrated and flexible when hydrated. This characteristic provides a means to constrain a self-expanding material (i.e. the support members) in a reduced diameter since the cellulosic material in its dry, stiff state counteracts the radial force of the self-expanding support members thereby preventing the graft from expanding until it becomes hydrated, thus more flexible. Once the bypass graft is inserted through the delivery system and into the vessel, the cellulosic material contacts fluid. As the graft material adsorbs fluid, it tends to become more flexible, allowing the support members of the bypass graft to expand towards its resting state urging the graft into intimate contact with the vessel wall.

Figure 2:
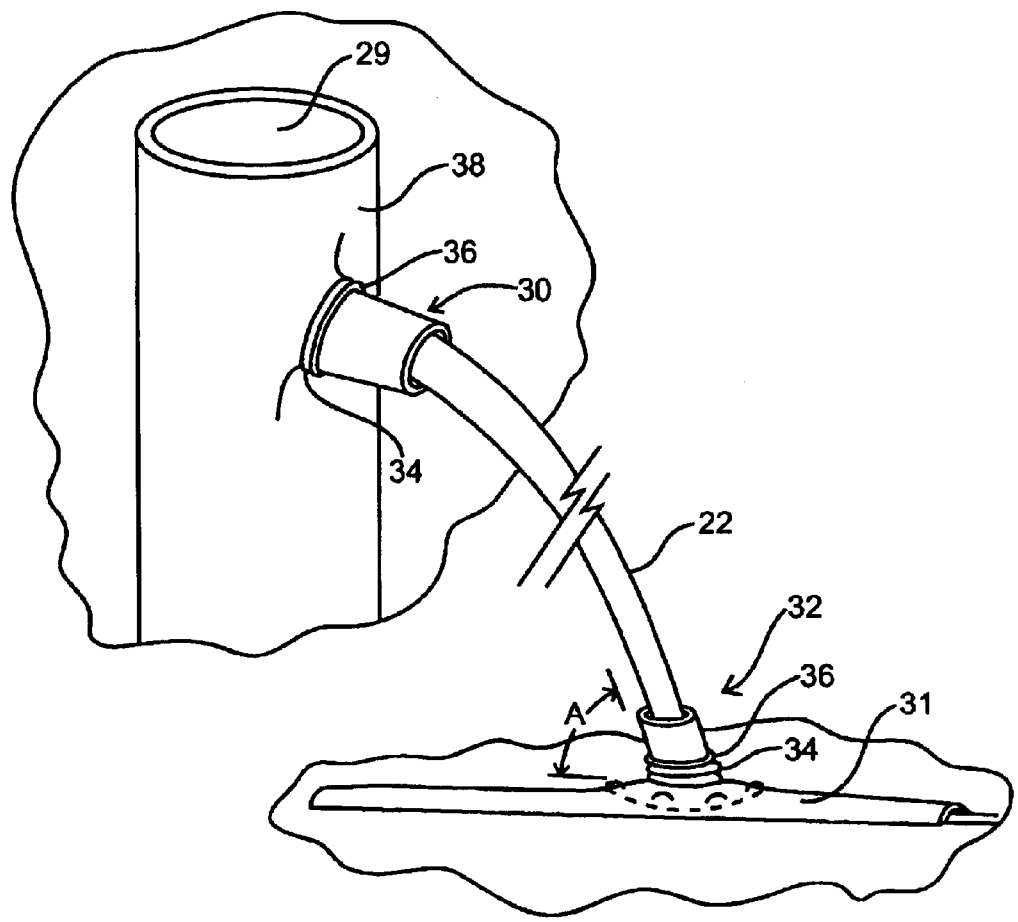
FIG. 2 shows a bypass graft secured between a large vessel and a small vessel.

FIG. 2 shows a bypass graft 22 with one end attached to a large vessel 29 using an end-side fitting 30 and a second end secured to a small or medium vessel 31 such as a coronary artery, using an end-side fitting 32. Fittings 30 and 32 are oriented at an angle A between the bypass graft and the host vessel ranging between 30 and 90 degrees, selected to optimize the fluid flow from one end to the other. Rings 34 secure portions 36 of the vessel walls 38 to the fittings.

Biological bypass grafts may be reinforced with support structures. This support structure may consist of a wire 40 wound into a helix (FIG. 3) or braided into a mesh. Other reinforcing structures that limit expansion of bypass graft 22 may be used. The support structure is bonded to fittings at each end by spot welding, crimping, soldering, ultrasonic welding, thermal bonding, adhesively bonding, or other bonding process, depending on the materials used. The support structure defines a lumen into which the bypass graft is inserted. After advancing the bypass graft through the support structure, the bypass graft is secured to the fittings at each end of the support structure. The support structure reduces the potential for kinking the bypass graft, limits its radial expansion, prevents aneurysm formation, limits longitudinal stretching, prevents excess twisting, and increases the graft burst strength. By mitigating the failure mechanisms of biological bypass grafts such as the saphenous veins, such reinforcing structures can improve the long-term durability and patency of biological bypass grafts.

Figure 3:
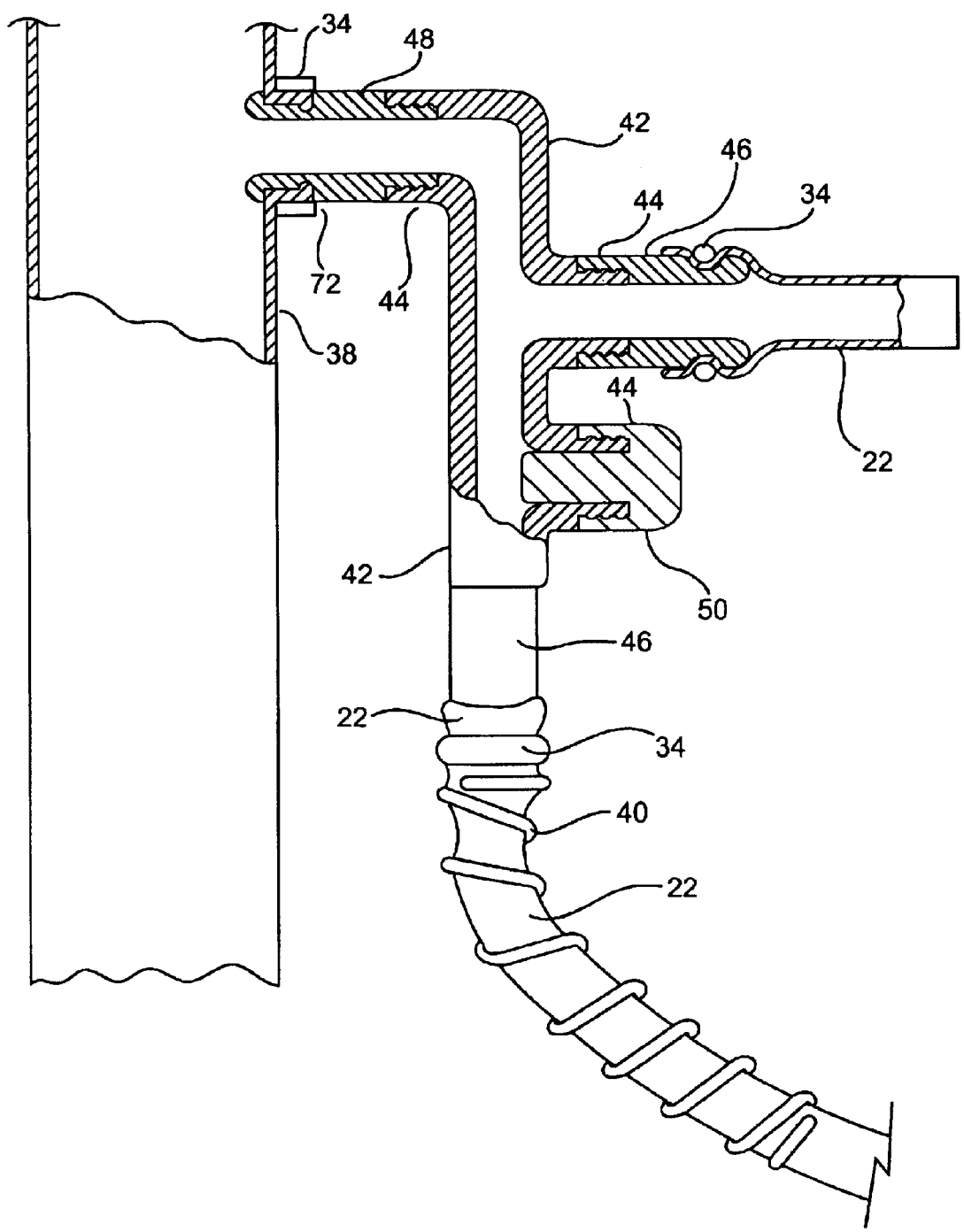
FIG. 3 shows modular fittings secured to the host vessel wall and branching into multiple passages and fittings that incorporate a support structure around the bypass graft.

Fittings can branch into multiple passages to attach multiple bypass grafts from a single vessel attachment point. FIG. 1 shows a bypass graft that is constructed with a bifurcation 28 and extends from the aorta to the left anterior descending and circumflex arteries. FIG. 3 shows modular or branching fittings 42 that have threads 44 to secure other fittings 46 and bypass graft and fitting combinations. A fitting 48 (also shown in FIG. 19d) is attached at a first host vessel location. Branching fitting 42 is threaded onto fitting 48 to produce a fluid tight seal. A bypass graft 22 and fitting 46 combination is threaded onto one extension of the branching fitting 42 producing a fluid tight seal. The opposite end of the bypass graft 22 is bonded to a second vessel location. Additional bypass graft and fitting combinations may be attached to the branching fitting 42 to produce multiple passages from a primary anastomosis. The fitting secured at the primary anastomosis may have a larger inner diameter than the branching bypass grafts to account for the increased cross-sectional area when considering multiple bypass grafts and provide enough cardiac output for all branches. When branches of the modular fitting 42 are not necessary, a cap 50 may be threaded onto the modular fitting 63 to close the desired branch and maintain a fluid tight seal.

Figure 4A:
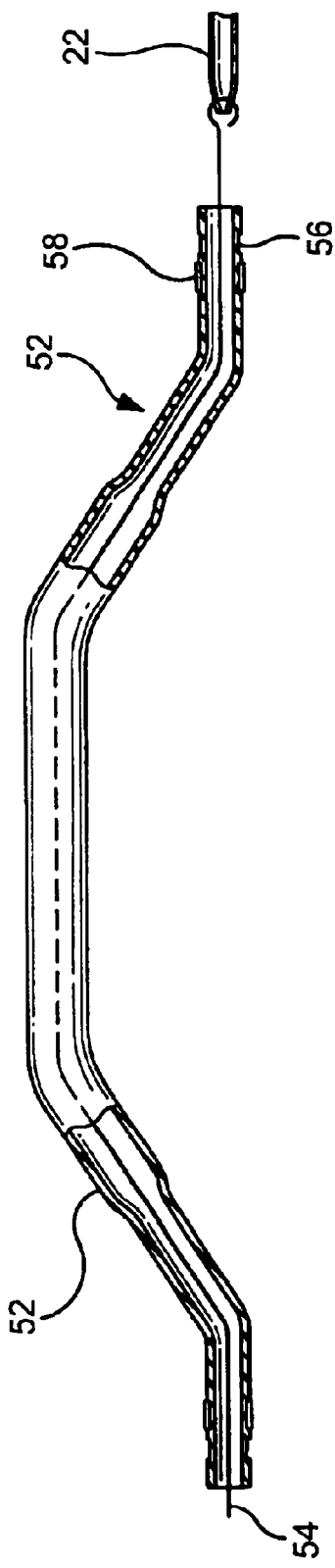
FIGS. 4a and b are side-sectional views of a bypass graft support structure incorporating fittings.
Figure 4B:
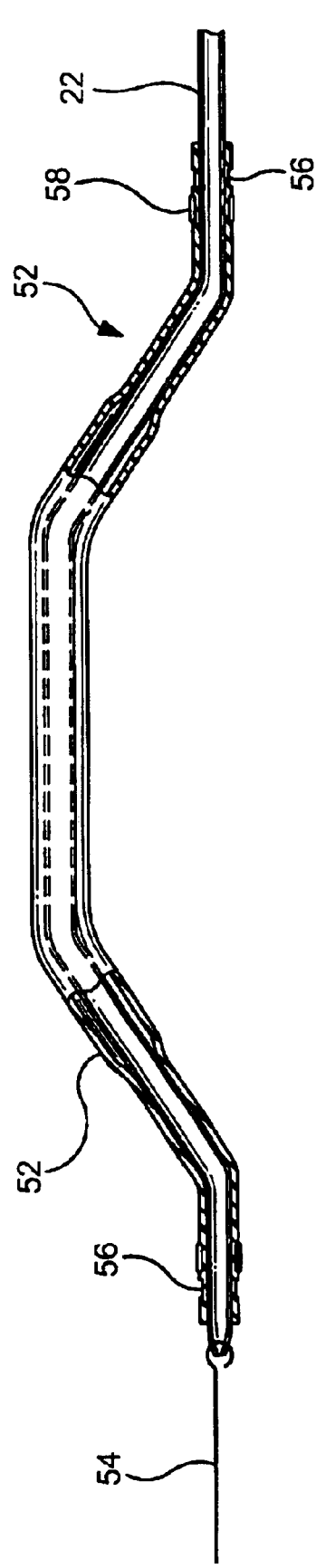
FIG. 4c shows the support structure of FIG. 4a with a bypass graft attached to the fittings and secured to the host vessel at two locations.

The support structure can be a synthetic graft formed into a tube, with or without support members, as shown in FIGS. 4a to c. A support structure 52 can be fabricated from a polymeric macroporous material to permit blood leaking through the bypass graft to flow outside the support structure. To produce macroporous support structures, pores can be laser drilled through the support structure material. Alternative manufacturing processes for creating pores may be used. Biological bypass grafts typically have branches that are sutured or stapled closed while harvesting the vessel and may leak for a period of time immediately after implantation. Blood leaking through a biological bypass graft enclosed in a nonporous or microporous (e.g. pore size less than 8 microns) support structure may accumulate in the space between the bypass graft and the support structure, possibly constricting or occluding the bypass graft. This depends on the pressure gradient from inside the biological bypass graft to the space between the bypass graft and the support structure. For applications where the biological bypass graft is completely impervious to leaking or the external surface of the biological bypass graft can be bonded to the support structure (e.g. using adhesives), nonporous or microporous support structures may be used.

Support structure 52 is preferably affixed to the fittings before attaching bypass graft 22 to the fittings. The support structure reinforces the entire length of the bypass graft. Using support structures that are not affixed to the fittings may cause kinking of the bypass graft between the anastomosis site and the end of the support structure. This defines a region where the bypass graft is not reinforced and a mismatch in compliance exists between a section of bypass graft strengthened by the support structure and a section of exposed bypass graft. Support structure 52 incorporates fittings at each end to attach a harvested vessel 22 and secure the bypass graft to a host vessel 29. A grasping tool 54, a suture with a noose or a wire having a distal gripping end such as forceps, is fed through the support structure to grab the end of the harvested vessel. As seen in FIG. 4b, the harvested vessel is pulled through support structure 52 such that a length of the harvested vessel extends beyond both ends of the support structure fittings. The ends of the harvested vessel are everted around the support structure fittings (FIG. 4c) and secured at the notched regions 56 of the fittings using retaining rings 34. Certain designs may incorporate an electrode 58 along each fitting near the notched region. In this embodiment, blood flowing through the bypass graft 22 contacts the endothelial layers of the harvested bypass graft and host vessel thereby minimizing the potential for thrombosis or biological reactions to foreign materials. Other fitting configurations designed to produce end-end or end-side anastomoses, as discussed below, may be attached to the support structure.

When microporous or nonporous support structures are used, the support structures serve dual purposes. They function as synthetic bypass grafts designed to produce end-end or end-side anastomoses at opposite ends of the bypass grafts. They also function as sutureless anastomosis devices to attach harvested vessels and reinforce the biological bypass grafts. This minimizes the product portfolio required for bypass grafting indications because a single device may reinforce and facilitate attaching harvested vessels between anastomosis sites and act as a synthetic bypass graft capable of producing sutureless anastomoses. In addition, these support structures enable using harvested vessels in catheter-based applications where harvested vessels do not have enough inherent column strength to be atraumatically advanced through a guiding catheter. The support structure protects the harvested vessel during deployment and reinforces the harvested vessel after bypass graft attachment.

Fittings

Bypass graft fittings preferably are constructed from a metal (e.g. titanium), alloy (e.g. stainless steel or nickel titanium), thermoplastic, thermoset plastic, silicone or combination of the aforementioned materials into a composite structure. Other materials may be used. The fittings can be coated with materials such as paralyne or other hydrophilic substrates that are biologically inert and reduce the surface friction. Alternatively, the fittings can be coated with heparin or thrombolytic substances designed to prevent thrombosis around the attachment point between the bypass graft and the host vessel. The fittings consist of one or more components designed to secure a bypass graft to the fitting and secure the fitting to the vessel wall, to produce a fluid tight bond between the bypass graft and the host vessel. The fittings may be used to produce end-end anastomoses for applications where retrograde blood flow is not essential (e.g. total occlusions and in-line bypass grafting), end-side anastomoses for medium and small diameter vessels (e.g. peripheral vessels and coronary vessels) where retrograde blood flow is essential, and end-side anastomoses for large diameter vessels (e.g. the aorta).

The fittings can include slots to maintain radial stiffness but increase axial flexibility. The slots can extend radially around a portion of each fitting at specific intervals along the fitting. The slots are formed by laser drilling, EDM, chemical etching or other suitable processes. Alternatively, the slots can be fabricated during injection molding, scintering or other material forming processes, depending on the type of material. The fitting also can be formed from a sheet of material laser drilled or chemically etched into a desired pattern, and bonded at the sides into a tubular fitting containing the slots. The slots preferably are located on the proximal portion of fitting to act as integrated strain relief to help prevent kinking of the attached bypass graft while permitting slight motion at the anastomosis site. The slots may also extend throughout the length of the fitting since the radial stiffness is sufficient to keep the vessel wall open at the insertion site into the host vessel. As described later, the slots also may be configured to facilitate compressing the fitting into a reduced diameter for insertion through a sheath having a smaller diameter than the expanded diameter of the fitting.

Fittings and fitting components can be made from biodegradable or bioabsorbable materials. Such fittings can be configured to break down after a set time period, e.g. three weeks, during which time the anastomosis site is reinforced with tissue in-growth producing a sufficiently strong bond between the bypass graft and the host vessel. This approach is useful when bonding biological bypass grafts to host vessels or reattaching to host vessel ends. Suitable bioabsorbable polymers include poly (L-lactic acid), polycaprolactone, poly (lactide-co-glycolide), poly (hydroxybutyrate), poly (hydroxybutyrate-co-valerate), polydioxanone, polyorthoester, polyanhydride, poly (glycololic acid), poly (D, L-lactic acid), poly (glycololic acid-co-trimethylene carbonate), polyphosphoester, polyphosphoester urethane, poly (amino acids), cyanoacrylates, poly (trimethylene carbonate), poly (iminocarbonate), copoly (ether esthers) (e.g., PEO/PLA), polyalkylene oxalates, polyphosphazenes, as well as biomolecules such as fibrin, fribrinogen, cellulose, starch, collagen and hyaluronic acid.

The bioabsorbable or biodegradable fittings may also incorporate the ability to diffuse drugs at a controllable rate at the anastomosis site. Manufacturing methods to provide this feature in fittings include adding a therapeutic agent to the base material during fabrication of the fitting components, and applying a coating containing a therapeutic agent after the fitting is fabricated. The approach can combine these methods. Suitable therapeutic coatings include dexamethasone, tocopherol, dexamethasone phosphate, aspirin, heparin, coumadin, urokinase, streptokinase, and TPA, applied by spraying, dipping or other means. The fittings also can be seeded with endothelial cells.

Figure 5A:
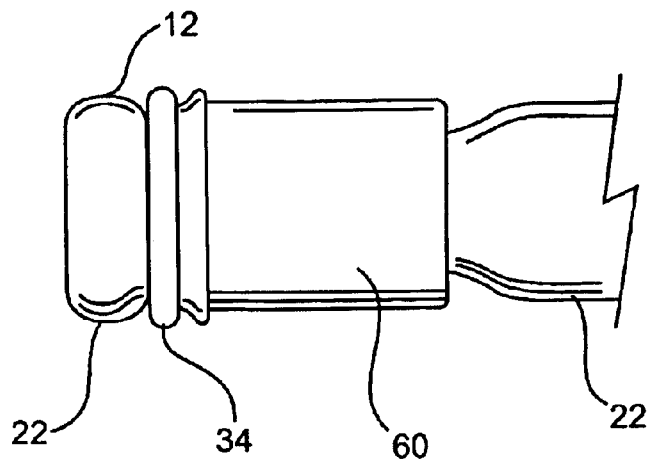
FIGS. 5a and b show a bypass graft attached to a fitting in accordance with an embodiment of the invention.
Figure 5B:
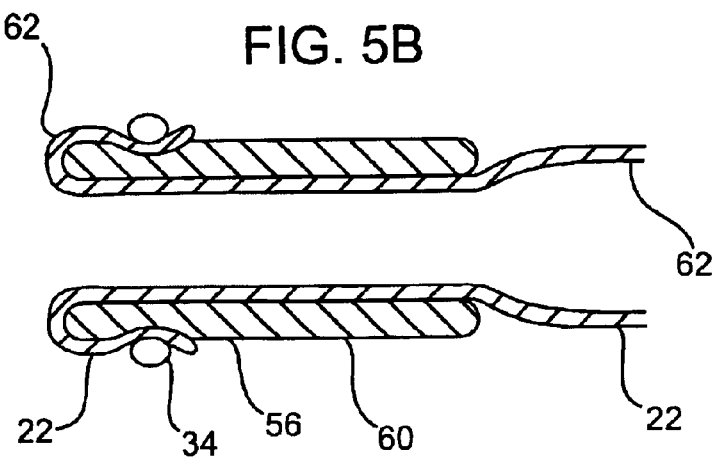

FIGS. 5a and b show an end-end fitting 60 designed to secure bypass grafts constructed from an internal mammary artery, radial artery, saphenous vein, or other harvested vessel such that only the endothelial layer 62 of the bypass graft is exposed to blood flow. Bypass graft 22 is fed through the interior of the fitting, everted and wrapped around the distal end. A grasping tool 54 (FIG. 4) is used to pull the bypass graft through the fitting, especially when using long fittings. A groove 56 is fabricated near the distal end of fitting 60 to prevent axial movement of retaining ring 34, thus retaining the bypass graft after positioning the retaining ring over the bypass graft and fitting combination. The retaining rings are designed to produce an interference fit between the bypass graft and fitting to hold the bypass graft in place and prevent leaking at the attachment point. Multiple retaining rings may be used to secure a bypass graft to a fitting.

Figure 9B:
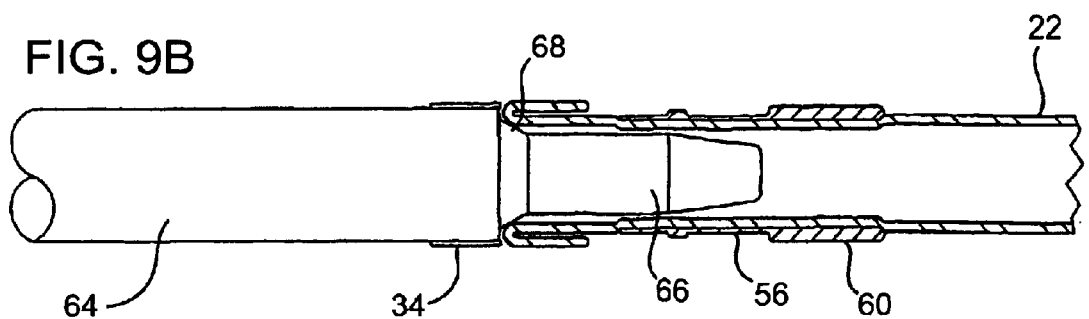
Figure 9C:
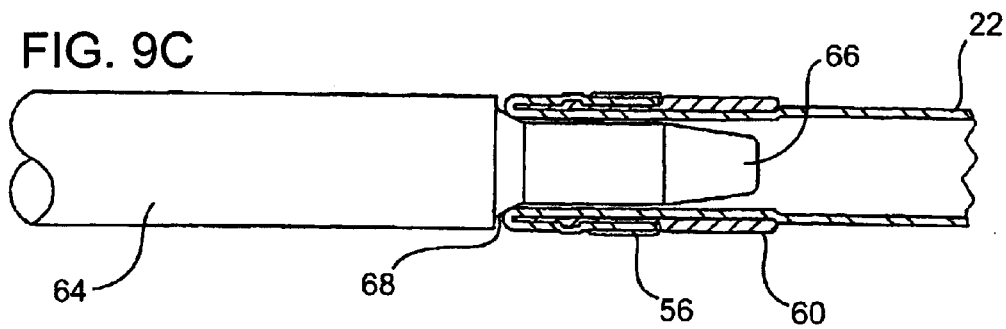
Figure 10A:
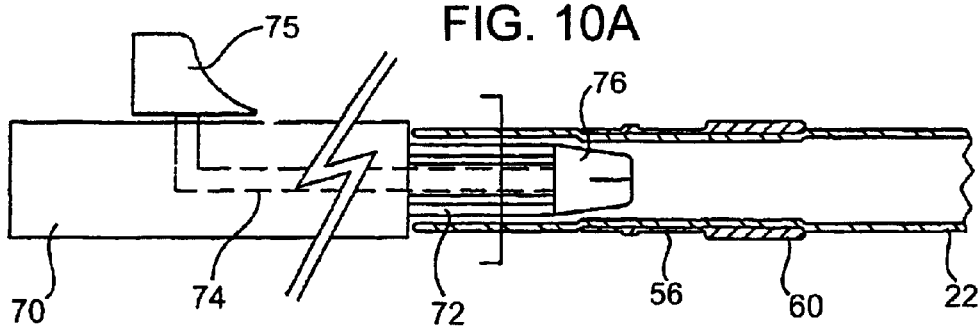
FIGS. 10a to d show an alternative everting tool.
Figure 10B:
Figure 10D:
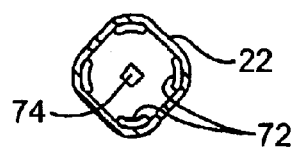
Figure 10C:
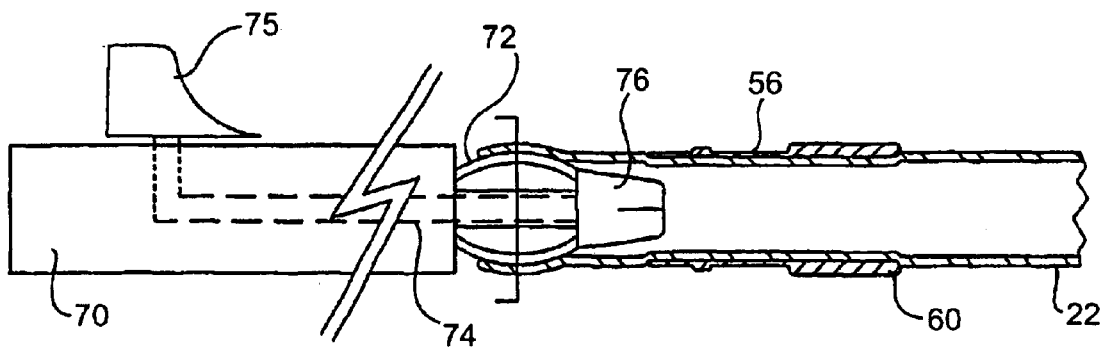

An everting tool preferably is used to wrap the bypass graft around the fitting prior to securing the bypass graft to the fitting. An everting tool 64 shown in FIGS. 9a to c is inserted into the distal end of the bypass graft 22 to be everted around fitting 60. The distal end 66 of the everting tool is designed to fit through the lumen of the bypass graft and the inner diameter of the fitting 60. Proximal to the everting tool distal end is a tapered or curved region 68 which causes the bypass graft 22 to wrap around the distal end of the fitting 60 as the bypass graft and fitting are advanced over the everting tool 64. A retaining ring 34 is housed around the everting tool 64 and is advanced over the bypass graft and fitting to secure the bypass graft 22 to the fitting 60.

This eversion process can be performed with the end of the bypass graft intact. Alternatively, one or more short, longitudinal incisions may be created at the end of the bypass graft. The sides of the cut bypass graft are pulled over the distal end of the fitting causing the bypass graft to wrap around the fitting. This method is particularly useful when using harvested vessels from patients that are partially diseased reducing the elasticity of the vessel and inhibiting the ability to evert the intact vessel over the fitting.

Another everting tool 70 (FIGS. 10a to d) uses an expansion mechanism to mechanically wrap the bypass graft around the distal end of the fitting. Strands 72 are attached together and to a stylet 74 with a distal cap 76 by spot welding or soldering the distal ends of the strands and distal end of the stylet together and covering this joint with a shrink tubing or adhesive. The proximal ends of the strands 72 are attached to everting tool 70. Stylet 74 is attached to a movable control knob 75 for moving the stylet relative to the rest of everting tool 70. As the knob is pulled, the strands bow radially outward causing the distal end of the bypass graft to expand. The bypass graft is then wrapped around the fitting 60 by advancing the expanded end of the bypass graft over the fitting.

Figure 6A:
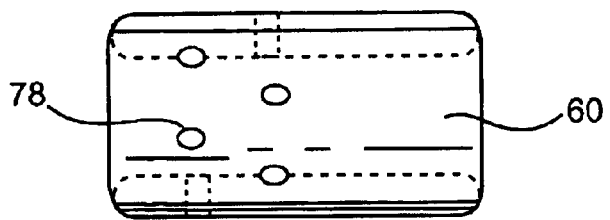
FIGS. 6a to c show an embodiment in which suture is used to secure the bypass graft to the fitting.
Figure 6B:
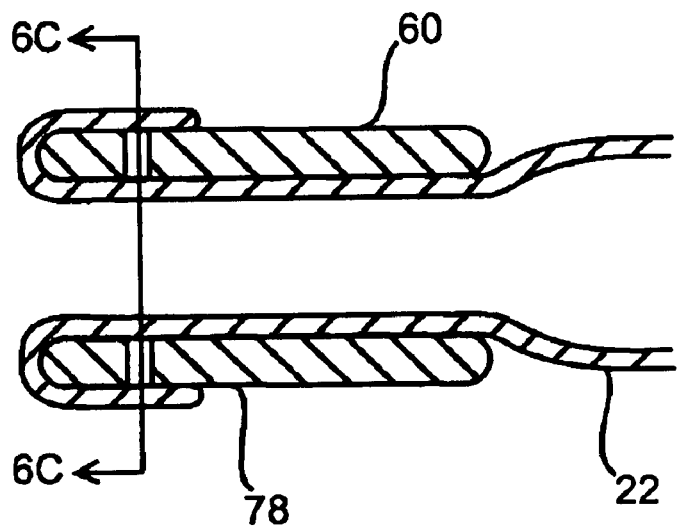
Figure 6C:
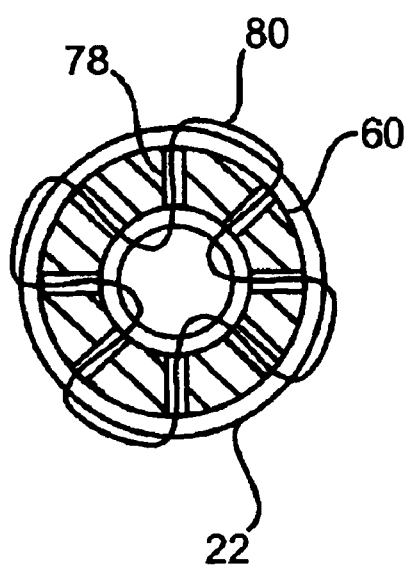

As shown in FIGS. 6a to c, the bypass graft 22 may be sutured or clipped to the fitting. Fitting 60, shown in FIG. 6a, incorporates holes 78 at spaced intervals around its circumference. The bypass graft is fed through and wrapped around the fitting as described above. The bypass graft is then secured by feeding sutures 80 through the holes 78 and tying the bypass graft to the fitting 60. Conventional suturing techniques may be used to secure the bypass graft to the fitting. Alternatively clips or staples may be used to secure the bypass graft to the fitting.

Figure 7A:
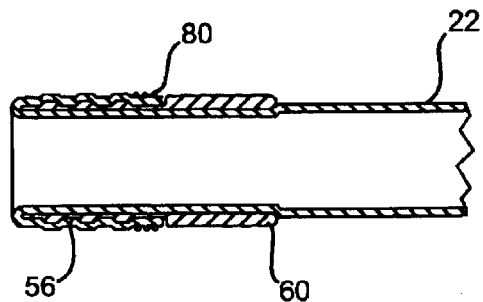
FIGS. 7a to c show an alternative end-end fitting securing the bypass graft to the fitting and the fitting to the host vessel using sutures.
Figure 7B:
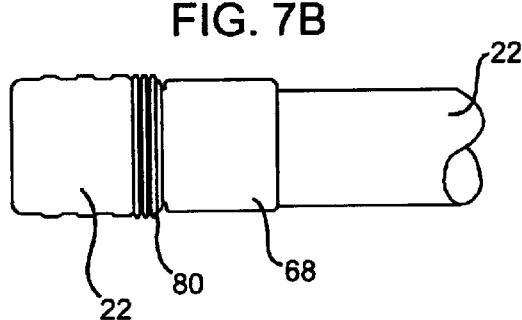
Figure 7C:
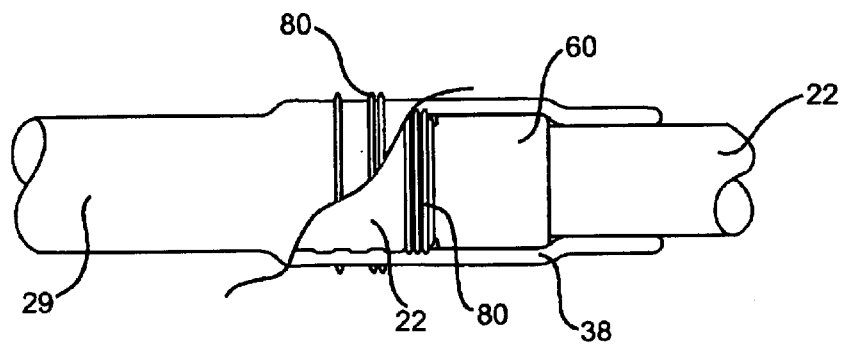

FIGS. 7a to c show another method of suturing a bypass graft to a fitting. The fitting 60 has notches 56 designed to provide an indentation to secure a bypass graft using the retaining ring or suture. Once the bypass graft 22 is advanced through the fitting and everted around the distal end, one or more strands of suture 80 are tied around the everted bypass graft and located in the notches 56 thereby producing a fluid tight seal. Sutures may also be used to attach bypass grafts to the outside of a fitting without everting the bypass graft. In addition, as shown in FIG. 7c, an end-end anastomosis may be produced between a bypass graft and fitting combination, such as that shown in FIGS. 7a and b, and a host vessel 29. The host vessel 29 is advanced over the bypass graft and fitting combination or the bypass graft and fitting are inserted into the host vessel 29 and suture 80 is tied around the host vessel, positioned in the notches of the fitting. This not only secures the host vessel to the bypass graft and fitting combination, but it produces a fluid tight seal.

An alternative mechanism to produce end-end anastomoses between grafts and host vessels is to insert the graft incorporating end-end fittings through the delivery system of the invention (described below) into the host vessel. Fittings similar to the compressible retaining rings shown in FIGS. 15a to d and having a compressible or deformable characteristic but incorporating a shape memory, are either laminated (synthetic grafts) or wrapped (synthetic or biological grafts) between layers of the graft material. When wrapping the end-end fitting between layers of graft material, the graft is inserted through the inner surface of the fitting and is wrapped at least once around the outer surface of the fitting. The graft material may be rolled around the end-end fitting to wrap the material more than once around the fitting. Then, adjacent layers of graft material are sutured, ultrasonically welded, thermally bonded or adhesively attached to incapsulates the fitting between the layers.

Once the ends of the graft are positioned at the correct anastomosis sites, the end-end fittings are sutured to the host vessel by inserting sutures around or through the end-end fitting from the exterior surface to the host vessel. The fittings are constructed from a memory elastic alloy, silicone, or polymer having a stiffness and elasticity selected to impose a shape memory to the resting geometry. Once the end-end fittings are positioned within the host vessel, they return towards their pre-shaped geometry causing them to contact the interior surface of the host vessel wall. The operator can determine the position of the end-end fittings within the host vessel by feeling for a change in compliance along the vessel. After locating the fittings, the operator uses attached needles to insert sutures through the vessel wall. The needles then are used to pass sutures either around or through the fittings. When memory elastic alloys are used for the fittings, the sutures must pass around the fittings, but may pass through the graft material. When silicone or polymers such as urethane having a relatively large percent elongation characteristic are used for the fittings, the sutures may pass through the fittings. Then the needles are used to pass the sutures back through the vessel wall on the opposite end of the end-end fitting. Alternatively, as shown in FIG. 6a to c and described above, the end-end fitting may incorporate holes that accept sutures for securing the fitting to the host vessel. In this case, a needle is used to puncture the vessel wall and insert the attached suture through one hole in the fitting and pass back through the vessel wall. After the sutures are placed, they are knotted to secure the fittings to the vessel wall. This method is used to secure bypass grafts with end-end fittings placed inside the host vessel. This method also may be used to secure reinforcing grafts with end-end fittings that are placed completely within the host vessel through a delivery system embodiment of the invention.

Figure 8A:
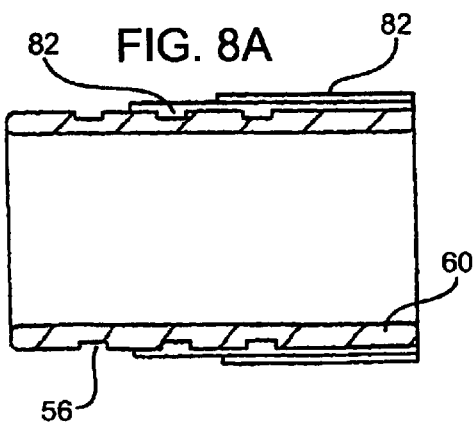
FIGS. 8a to d show alternative end-end fittings.
Figure 8B:
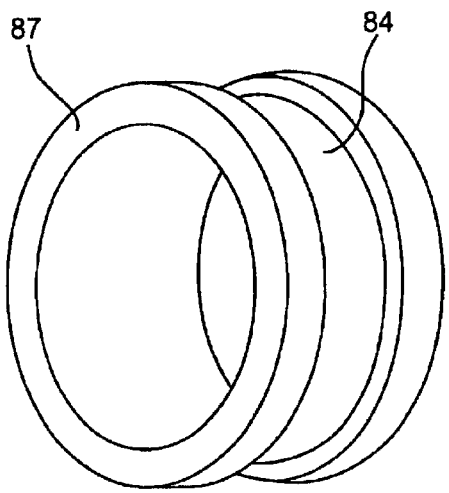
Figure 8C:
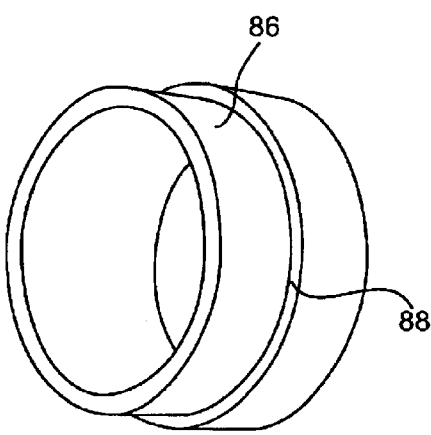

FIGS. 8a to d show various fitting embodiments that enable attaching bypass grafts using retaining rings. FIG. 8a shows a fitting embodiment that has steps 82 to accommodate varying diameter vessels with a single fitting. Fitting 83 (FIG. 8b) incorporates a notched middle region 84 to accept one or more retaining rings for securing the bypass graft to the fitting and/or the fitting to the host vessel. The fitting can have a slotted middle region to enable suturing or clipping the bypass graft to the fitting and/or the fitting to the host vessel. A fitting 86 (FIG. 8c) incorporates a notched distal region 88 to accept the bypass graft and retaining ring and create a smooth transition from the external surface of the fitting to the external surface of the retaining ring and bypass graft. This prevents excess material that could hinder insertion of the bypass graft and fitting combination through the delivery system. The devices shown in FIG. 8 may function as retaining rings to compress the bypass graft against a fitting as the retaining ring is advanced over the bypass graft toward a fitting interface.

Figure 8D:
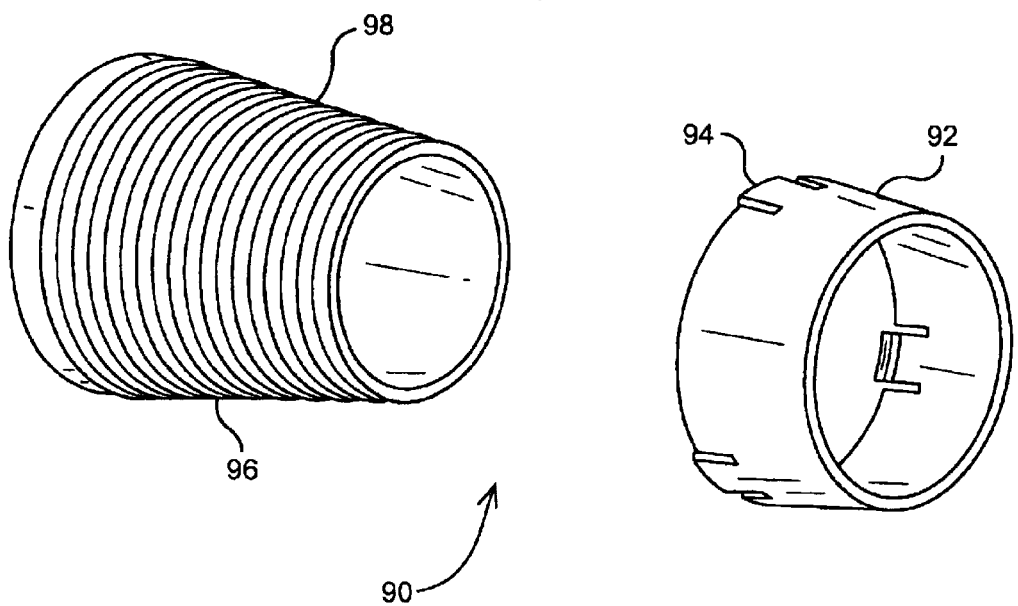

FIG. 8d shows a snap fitting 90 designed to facilitate bonding the bypass graft. A distal piece 92 of the snap fitting incorporates extensions 94 to lock distal piece 92 to mating teeth 96 of a proximal snap fitting piece 98. The proximal piece is tapered to accommodate a range of bypass graft diameters. The bypass graft is inserted through proximal piece 98 and everted over the external surface of the proximal piece. Alternatively, the bypass graft is positioned over the exterior surface of proximal piece 98. Then, distal piece 92 is advanced over the bypass graft and proximal piece interface, and is locked to the teeth thereby securing the bypass graft to the proximal piece. The distal piece is configured for end-end anastomoses. It can be modified to accommodate end-side anastomoses. The bypass graft and snap fitting combination can be secured to a host vessel using retaining rings (for end-end anastomoses) or compression rings (for end-side anastomoses), as will be described below. Alternatively, a second distal snap fitting piece like 92 designed to fit over distal piece 92 may be used to secure the host vessel to the bypass graft and snap fitting combination. This is especially useful when reattaching severed vessel ends.

FIGS. 11a to f show retaining rings used to secure the bypass graft 22 to the fitting. In FIGS. 11a to d, the retaining rings are pre-shaped and have rectangular, circular, or elliptical cross-sections with eyelets 100 that facilitate positioning the retaining ring over the fitting and may be used to suture the retaining rings closed for additional support.

Figure 11A:
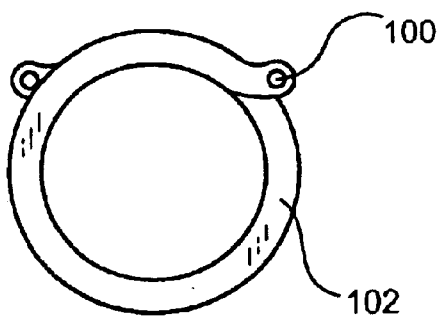
FIGS. 11a to i are end views of retaining rings used to bond the bypass graft to the fitting and/or the fitting to the vessel wall in accordance with embodiments of the invention.
Figure 11B:
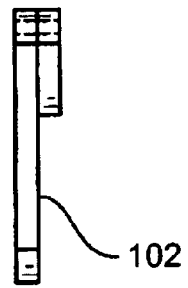
Figure 11C:
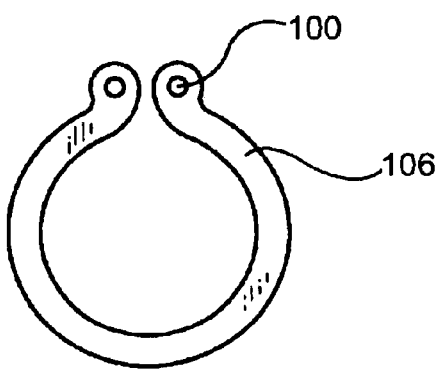
Figure 11D:
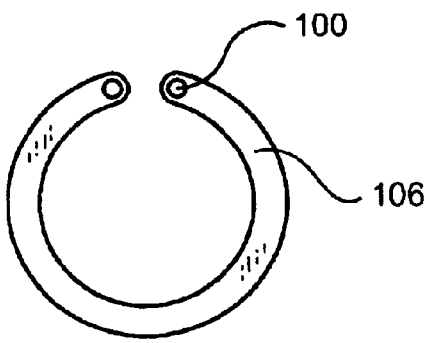

A retaining ring 102 in FIGS. 11a and b is preshaped to be wound beyond a single turn. When eyelets 100 are squeezed together, the diameter of the retaining ring enlarges making it easier to position over the bypass graft and fitting combination. Rings 104 and 106 in FIGS. 11c and d have the coiled wire extending short of a single turn. When eyelets 100 are spread apart, the diameter of the retaining ring enlarges. An expanding tool 108 shown in FIG. 16 has two extensions 110 insertable through the eyelets of the retaining ring. The expanding tool is used to expand the retaining rings above by squeezing the eyelets together for retaining ring 102 or spreading the eyelets apart for the retaining rings 104 and 106.

Figure 11E:
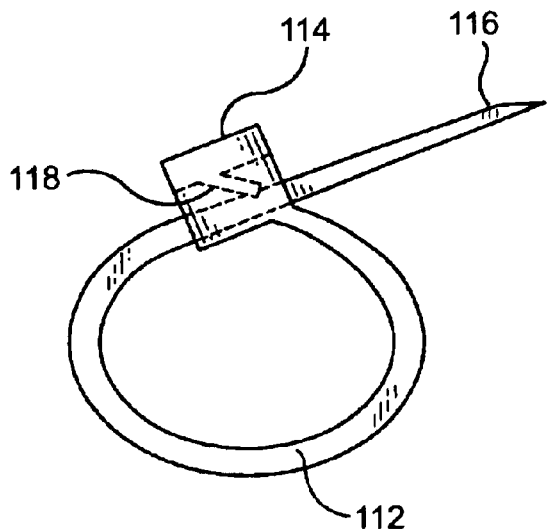

FIG. 11e shows a retaining ring 112 that incorporates a ratchet mechanism 114. As the distal end 116 of the retaining ring is advanced through the ratchet mechanism, a latch 118 prevents the retaining ring from opening by grasping the teeth of the retaining ring. This locks the retaining ring around the bypass graft and fitting interface producing a fluid tight fit. This retaining ring may also be used to secure the host vessel to the graft fitting, as in FIGS. 43a and b.

Figure 11F:
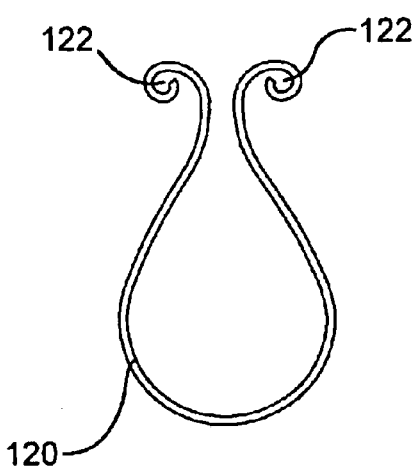

A retaining ring 120 shown in FIG. 11f is similar to ring 104 but incorporates looped regions 122. This retaining ring atraumatically slides over the bypass graft and fitting combination without the need to pull the ends of the retaining ring apart. The distal region of the retaining ring spreads open while advancing over the bypass graft and fitting combination and springs closed after extending past the maximum diameter of the bypass graft and fitting combination. Alternatively, the retaining ring can be an enclosed circle and exhibit an elastic characteristic to permit stretching into an enlarged diameter and compress around the bypass graft to fitting interface when released.

Figure 11G:
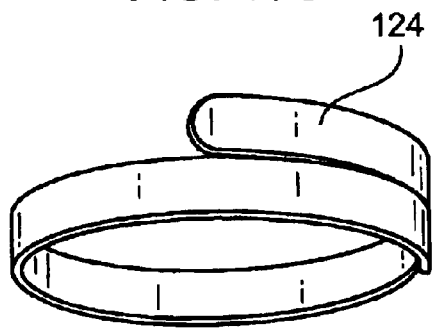

A retaining ring 124 shown in FIG. 11g is a preshaped member wound beyond a single turn and having radiused edges and ends. One representative fabrication process for the preshaped retaining ring involves forming the raw material into a desired geometry and exposing the material to sufficient heat to anneal the material into this predetermined shape. This process applies to metals, alloys (e.g. nickel titanium) and polymers. The preshaped retaining ring configuration is expanded by inserting the expansion tool into the middle of the retaining ring and opening the expansion tool thereby enlarging the diameter of the retaining ring. Once the retaining ring is positioned, the force causing the retaining ring to enlarge is removed causing the retaining ring to return towards its preformed shape thereby compressing the bypass graft against the fitting. This retaining ring may also be used to secure a fitting to a host vessel since this retaining ring may be expanded to expose an opening between opposite ends adapted for placement over the host vessel. Once positioned over the host vessel to fitting interface, the retaining ring is allowed to return towards its preformed shape thereby compressing the host vessel against the fitting. Retaining ring 124 can be manufactured from a deformable material and crimped over the bypass graft to fitting interface or host vessel wall to fitting interface for securing purposes.

Figure 11H:
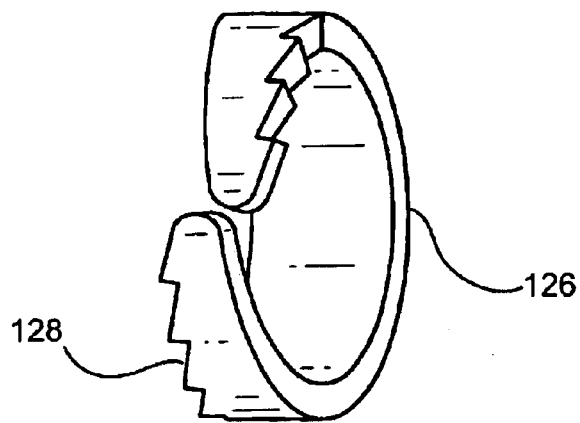
Figure 11I:
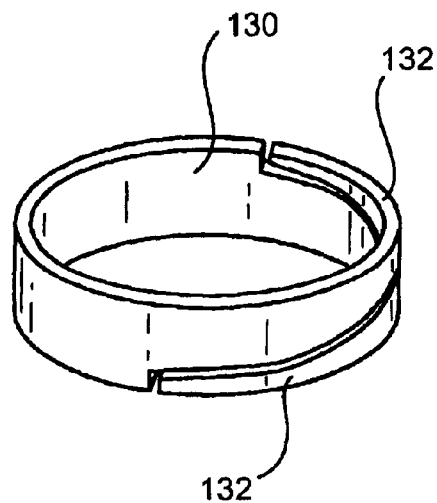
Figure 14C:
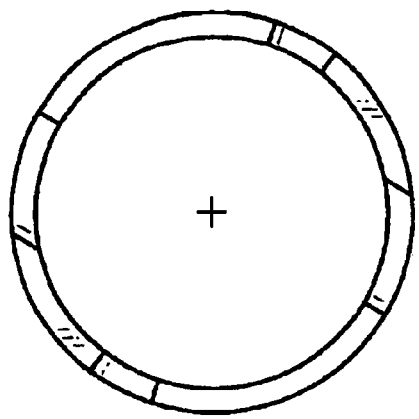
FIGS. 14a to e show alternative retaining ring embodiments.
Figure 14B:
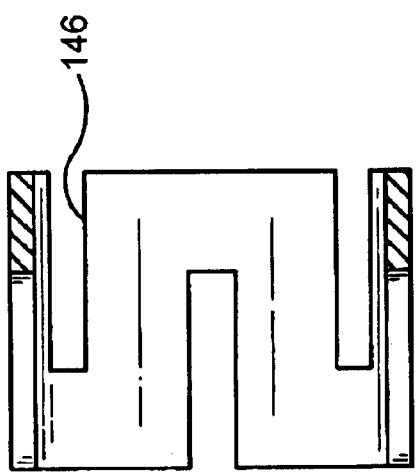
Figure 14A:
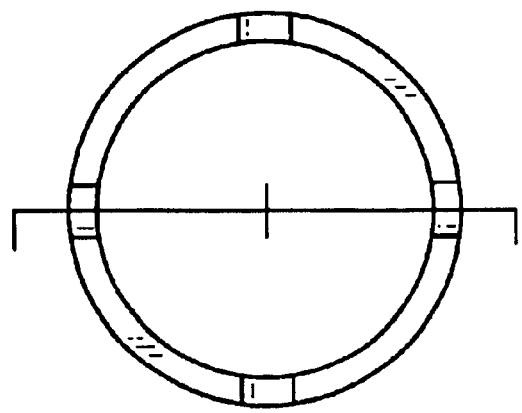
Figure 14D:
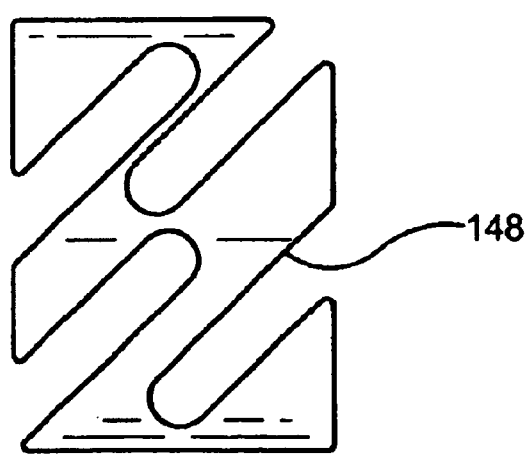
Figure 14E:
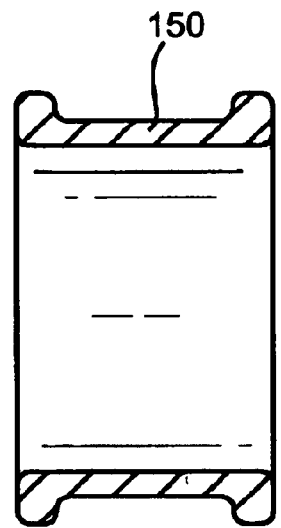

FIG. 11h shows another retaining ring 126 that does not incorporate elastic memory characteristics. This retaining ring is opened for positioning around the bypass graft to fitting interface or the host vessel to fitting interface and is closed, causing teeth 128 to engage and lock the retaining ring in the closed position. Further closing the retaining ring causes the diameter to decrease and exert additional compression force. FIG. 11i shows another retaining ring 130 having preshaped members 132 wound beyond a single turn. This embodiment also permits expansion of the retaining ring to facilitate positioning, but is configured to form a complete ring in its resting shape.

FIGS. 12a and 12b show a retaining ring 136 with an end extension 138 that fits through a slot. FIGS. 13a and b show a retaining ring 140 with eyelets 100 and a pivot point 142.

The retaining ring shown in FIGS. 13c and d has semicircular sections 144 for increased stiffness. The retaining ring may be fabricated from a metal, alloy, thermoplastic material, thermoset, or composite. However, the retaining ring must permit approximately 30% enlargement in diameter without becoming permanently deformed. Thus, after placement, the retaining ring will collapse around the bypass graft and fitting interface to form a secure seal.

Other retaining ring embodiments, shown in FIGS. 14a to e and FIGS. 15a to d, are fabricated as enclosed rings but enable expansion to position around the bypass graft to fitting interface. The retaining rings 146–154 shown in FIGS. 14a to e and FIGS. 15a to d are enlarged to deploy around the bypass graft and fitting combination and are allowed to return towards their preformed shape, once positioned, thereby securing the bypass graft to the fitting and providing a fluid tight seal. Another expandable retaining ring 156, shown in FIGS. 15e and f, incorporates petals 158 so an end-end fitting may be used to produce an end-side anastomosis.

Figure 17C:
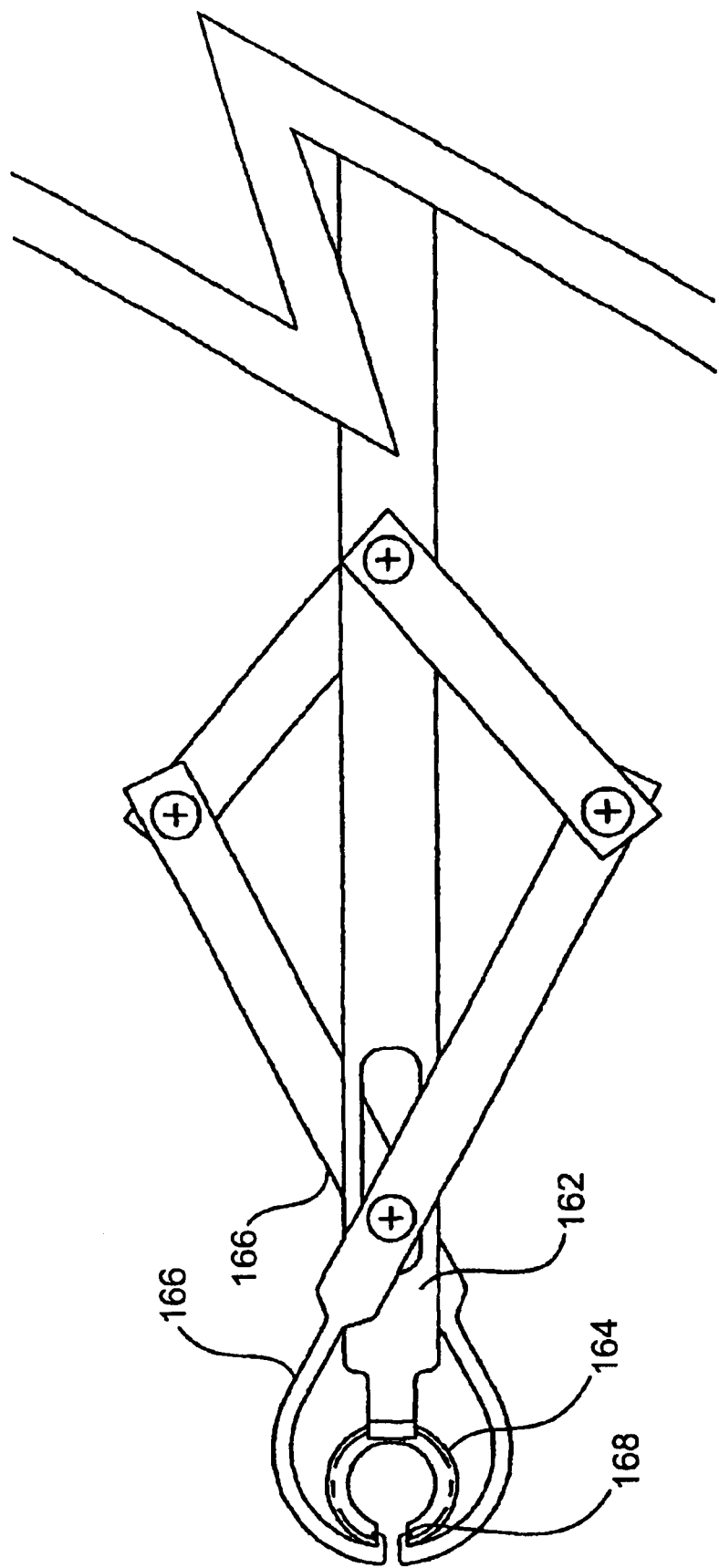

An alternative expansion tool 160 is shown in FIGS. 17a to c. This expansion tool is designed to expand the retaining ring by pulling the ends of the retaining ring relative to an anchor point. A stylet 162 holds a retaining ring 164 in place and produces the anchor point. Legs 166 of the expansion tool have notches 168 positioned at the edges of the retaining ring. The legs rotate about a pivot pin 170 fixed to the handle. When a knob 172 is advanced relative to the handle, the legs move radially outward thereby opening the diameter of the retaining ring. Once positioned around the bypass graft and fitting interface, tension on the knob is released allowing the retaining ring to compress the bypass graft against the fitting. The expansion tools described above may also be used to position retaining rings around a host vessel to fitting interface producing a fluid tight bond between the bypass graft and the host vessel.

Figure 18:
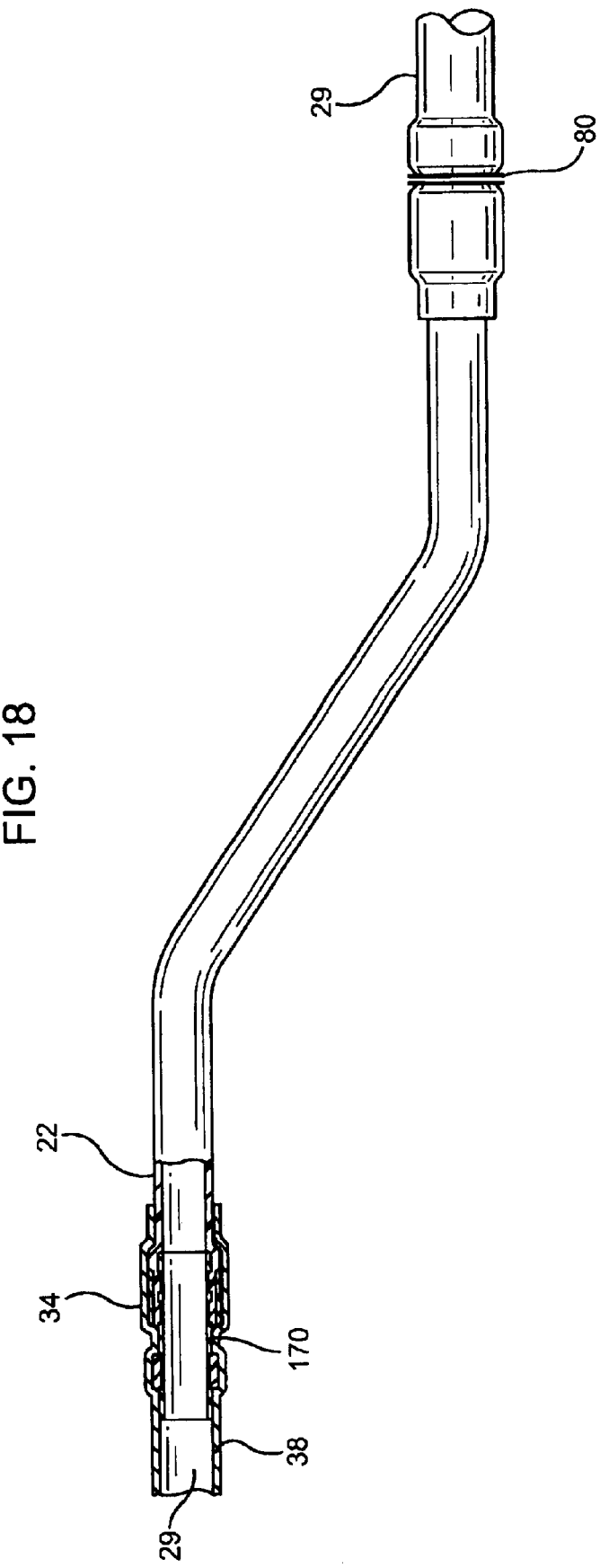
FIG. 18 shows a bypass graft attached to end-end fittings and secured to the host vessel.

Alternative embodiments of the invention involve attaching the bypass graft around the exterior of the fitting as opposed to feeding the bypass graft through the interior and wrapping it around the end of the fitting as discussed above. For example, FIG. 18 shows a bypass graft 22 secured around the exterior of fittings 170 using retaining rings 34. The bypass graft 22 is advanced over the exterior of fitting 170 and is secured with a retaining ring 34, suture 80, or staples (not shown).

Delivery Systems

Conventional anastomosis techniques require a relatively large incision through the vessel wall and use sutures, commercially available clips, or stapling devices to bond the end of the bypass graft to the exposed edges of the vessel wall. In certain cases, the structural integrity of the vessel wall may be weakened causing the vessel to collapse at the anastomosis site, especially when the bypass graft is not appropriately aligned to the host vessel incision. Therefore, the delivery system embodiments of the invention are designed to quickly access the host vessel through a small puncture in the vessel wall. As such, the delivery systems are designed to prevent excess blood loss when accessing the host vessel and deploying the bypass graft and fitting combination, thereby eliminating the need to stop or re-route blood flowing through the host vessel. This approach also improves the leak resistance around the fitting due to elastic compression of the vessel wall around the fitting and automatically aligns the bypass graft to the host vessel wall at the anastomosis site.

The delivery system embodiment depends on the application. For catheter-based bypass grafting applications, as discussed in U.S. application Ser. No. 08/966,003 filed Nov. 7, 1997, a catheter (e.g. guiding member) is intralumenally advanced to the proximal anastomosis site. A puncture device (e.g. needle) is used to perforate the vessel wall and enable advancing a guiding member exterior to the vessel. A dilating member expands the opening to atraumatically advance the guiding member through the vessel wall. A balloon may be attached to the guiding member and inflated to restrain the guiding member outside the host vessel and prevent leaking at the puncture site; the balloon would be deflated while the guiding member is advanced through the vessel wall. The catheter is then manipulated (e.g. steered, advanced, retracted, and/or rotated) to the distal anastomosis site. The puncture device is used to perforate the vessel wall and access the interior of the vessel at the distal anastomosis site. A guidewire may be advanced through the puncture device or the puncture device may function as a guidewire to provide a passage to advance the guiding member into the interior of the host vessel at the distal anastomosis site. Once the guiding member is advanced through the puncture and into the interior of the host vessel, the bypass graft is advanced inside or outside the guiding member to the distal anastomosis site. A stylet may be used to advance the bypass graft along the guiding member or maintain the position of the bypass graft as the guiding member is retracted. The balloon attached to the guiding member may again be inflated to keep the guiding catheter within the vessel at the distal anastomosis site and prevent leaking. The bypass graft is secured to the host vessel at the distal anastomosis site. Then, the guiding member is retracted so the bypass graft is able to contact the host vessel wall at the proximal anastomosis site. If a balloon was inflated to maintain the position of the guiding member within the vessel, it must be deflated prior to retracting the guiding member through the vessel wall. The bypass graft is then secured to the host vessel wall at the proximal anastomosis site and the guiding member is removed leaving the bypass graft as a conduit for blood to flow from the proximal anastomosis to the distal anastomosis. As previously stated, the fittings used to secure the bypass graft to the host vessel wall at the proximal and distal anastomosis sites depends on the application and whether retrograde blood flow through the anastomosis site is desired.

Figure 19B:
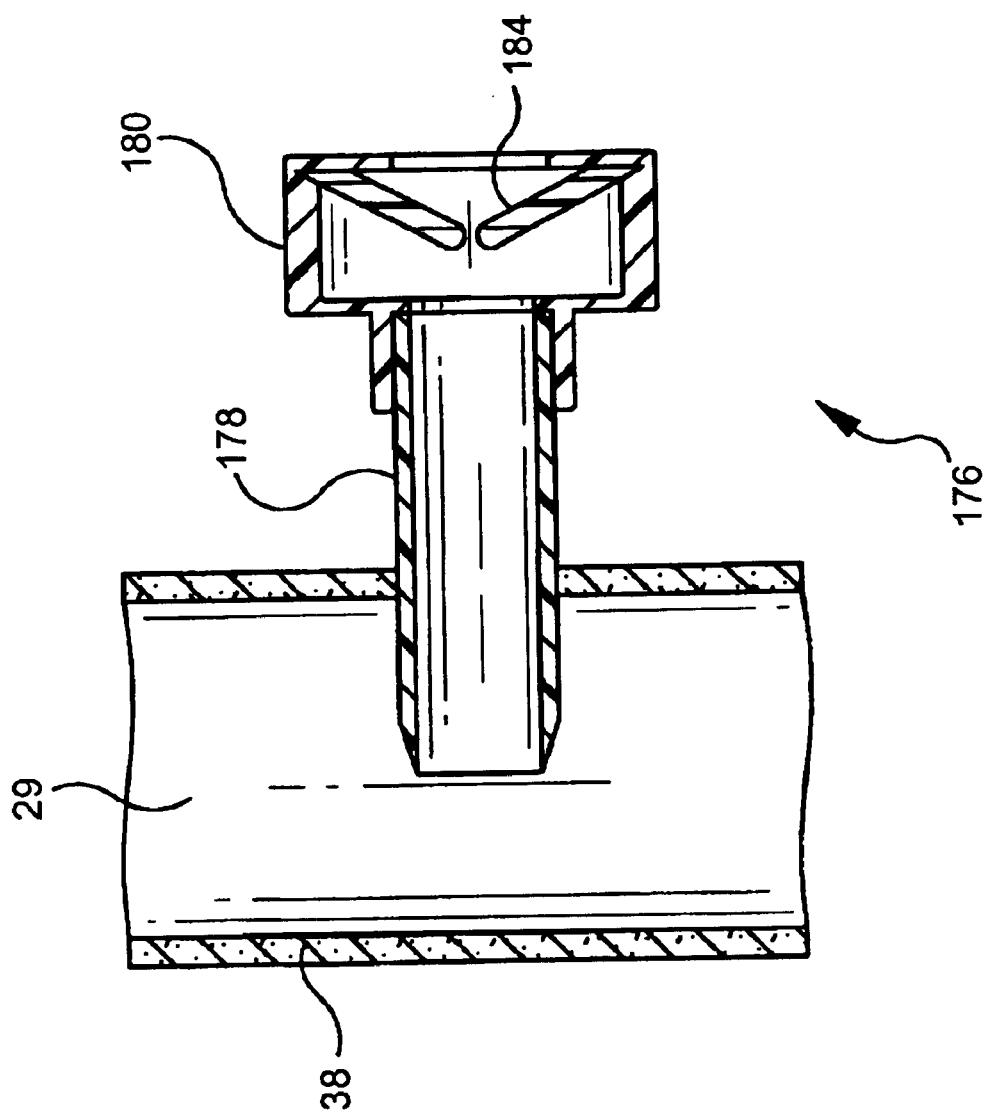

For surgical applications, physicians are able to access the anastomosis sites from the exterior surface of the host vessel(s). Unlike the catheter-based approach where the bypass graft is advanced past the distal end of the delivery catheter during deployment, the delivery system of the surgical approach must permit removal after both ends of the bypass graft are secured and the delivery system resides around the attached bypass graft. FIGS. 19a to c show representative steps to position a bypass graft and fitting combination through a vessel wall. A needle 172 is inserted through a dilator 174 that has been inserted through a sheath 176. The needle, dilator, and sheath combination is positioned at the target vessel location. Especially for minimal access procedures involving endoscopic visualization and manipulation through small incisions, sensors may be incorporated in the needle, dilator, and/or sheath to position the delivery system at the target location. As described in U.S. application Ser. No. 08/966,003 filed Nov. 7, 1997, the sensors can include ultrasonic transducers, such as those fabricated from piezoelectric material, doppler crystals, infrared transducers, or fiberoptics. Alternatively a lumen may permit the injection of radiopaque contrast material within the vessel to verify the position using fluoroscopy.

Needle 172 is used to puncture the vessel wall 38 and is advanced into the interior of the host vessel 29. The needle may be designed with a tapered or stepped distal end to restrict movement of the needle beyond the end of the dilator and prevent perforating the opposite side of the vessel or unwanted anatomy. A guidewire (not shown) may be advanced through the needle to provide a path over which the dilator and sheath may be advanced. When using a guidewire, the needle may be retracted to prevent unwanted perforations or abrasions to the host vessel or adjacent anatomy. Dilator 174 is then advanced over the needle or guidewire and into the host vessel. Subsequently, the needle (if not already retracted to insert the guidewire) may be removed from the vessel or retracted inside the dilator. The dilator is tapered to provide a smooth transition when advancing the dilator through the vessel wall. The vessel wall inherently forms a seal around the dilator preventing excess blood leakage from the vessel.

Sheath 176 has a radius or tapered distal end 178 and forming a smooth transition from the dilator to the body of the sheath is contained around the dilator. Once the dilator is positioned within the vessel, the sheath may be advanced over the dilator and into the vessel as shown in FIG. 19b. At this point, the dilator may be removed. This technique of inserting a sheath into a vessel over a dilator and needle is commonly used by physicians when performing the Seldinger technique during catheterization procedures or inserting I.V. catheters into veins for withdrawal of blood or introduction of medicines. The sheath and dilator may be constructed from polyethylene, or other polymer that may be extruded or molded into a tube. The sheath and dilator may incorporate a braided layer laminated between two polymer layers to resist kinking and improve the column strength and torque response. A taper and radius may be formed in the distal end of the dilator and sheath by thermally forming the raw tubing into the desired shape. In addition, the sheath may incorporate a softer distal tip fabricated by thermally bonding a short section of lower durometer tubing to the sheath or tapering the thickness of the sheath tubing.

Hubs 180 and 182 on the sheath and dilator respectively may be fabricated from polycarbonate, polyethylene, PEEK, urethane or other material, which may be injection molded, adhesively bonded, ultrasonically welded, or thermally bonded to the tube. Hub 180 contains at least one and preferably two grooves, slits, or series of perforations along the hub to enable the operator to split the hub when removing the sheath from around the bypass graft. Hub 180 houses a hemostatic valve 184 constructed of silicone, urethane, or other material having a low durometer and a large percent elongation characteristic. The hemostatic valve prevents excess blood loss through the sheath when positioned inside the vessel. The valve also incorporates at least one groove, slit, or series of perforations to permit separation when tearing the sheath from around the bypass graft. A side port may be included to aspirate and flush the sheath. The hub may alternatively be a separate piece from the tear-away sheath such that it may be independently removed from around the bypass graft. This hub would include a luer fitting to enable securing onto a mating piece of the tear-away sheath, or other mechanism to permit removably attaching the hub to the tear-away sheath. This hub may incorporate at least one groove, slit, or series of perforations to enable splitting the hub to form an opening to remove the hub from around the bypass graft. Alternatively, the hub may include a slot, which during use is closed to prevent fluid from leaking, but can be aligned to form an opening for removal from around the bypass graft.

As shown in FIGS. 19c and d, the sheath provides a mechanism to insert a fitting. In FIG. 19d, the bypass graft is not attached to the fitting 48 prior to insertion into the vessel 29. However, the bypass graft may be attached to the fitting prior to inserting the fitting into the vessel. A plunger 186 will vary depending on whether the bypass graft 22 is attached to the fitting before or after inserting the fitting into the host vessel.

After securing the bypass graft to the fitting and advancing the fitting into the host vessel, as previously described, the bypass graft and fitting combination must be attached to the vessel wall. For some applications, the fitting may be attached to the host vessel prior to securing the bypass graft to the fitting, as seen in FIG. 19d.

Figure 20A:
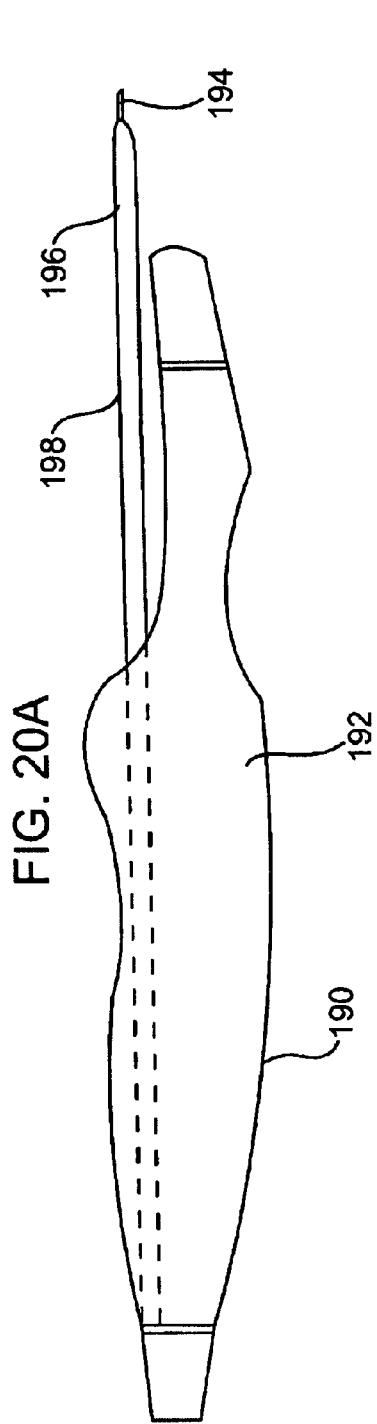
FIGS. 20a to c show an access device designed to puncture the vessel wall and insert a sheath into the vessel.
Figure 20B:
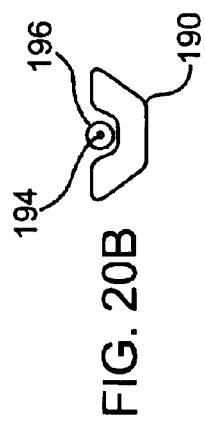
Figure 20C:
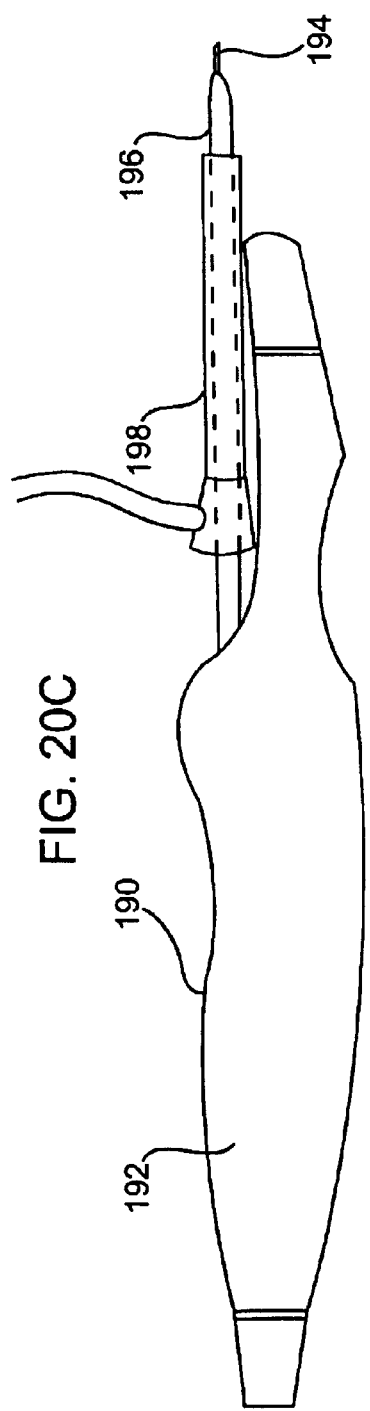

The delivery system used to access the vessel and position a sheath through the vessel wall may be consolidated into a single puncture device. The puncture device 190 shown in FIGS. 20a to c includes a handle 192 designed to push a perforating member 194 and dilating member 196 through the vessel wall and into the vessel interior. A sheath 198 is positioned around the dilating member for deployment through the vessel wall. A guidewire may also be advanced through the perforating member once positioned inside the vessel to provide a line to advance the dilating member and sheath without perforating the opposite end of the vessel wall or adjacent anatomy. This puncture device also facilitates incorporating advanced features, such as forward looking imaging and steering, since the handle provides a structure to connect transducer leads and acts as an anchor from which to retract pull-wires and deflect the distal end of the puncture device.

Figure 21A:
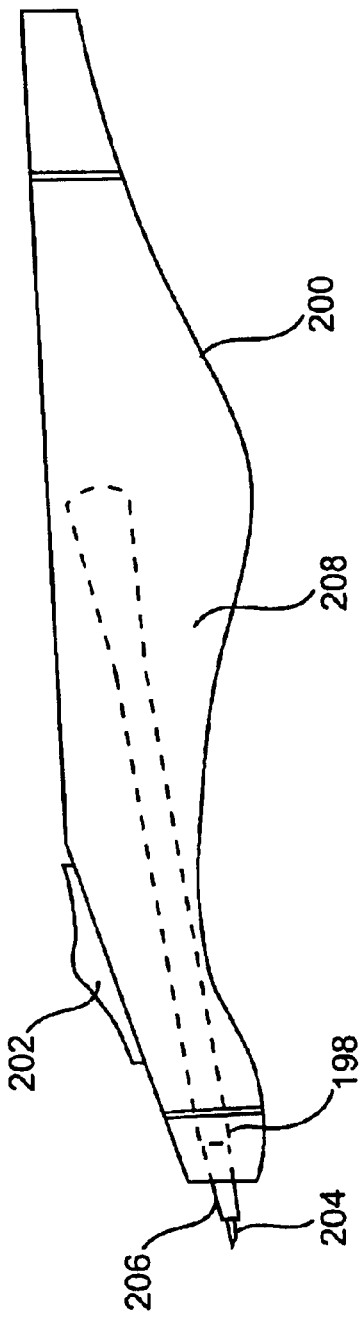
FIGS. 21a to c show an access device having a movable mechanism to puncture the vessel wall and insert a sheath into the vessel.
Figure 21B:
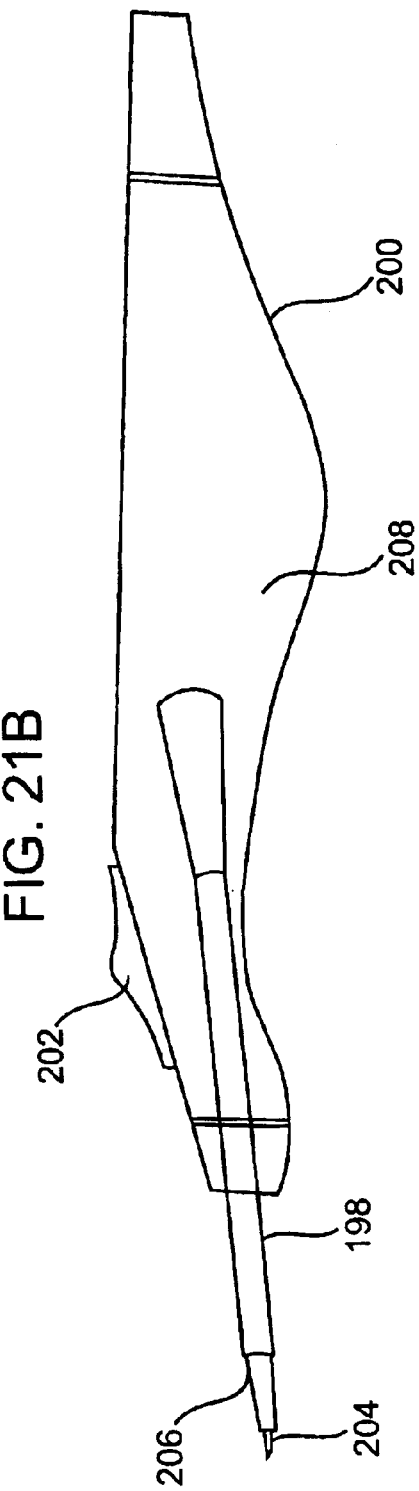
Figure 21C:
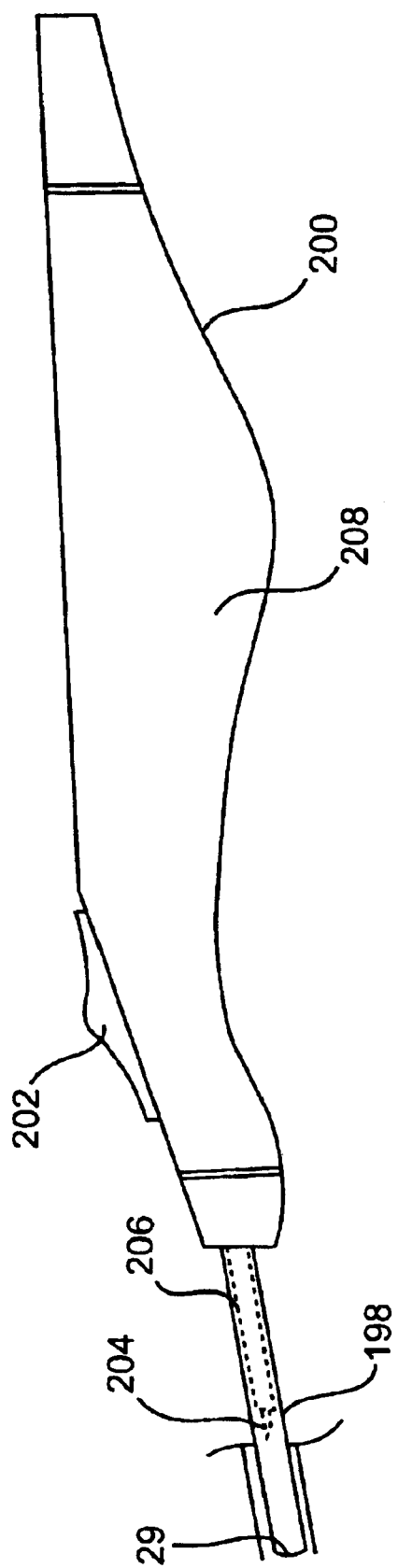
Figure 22:
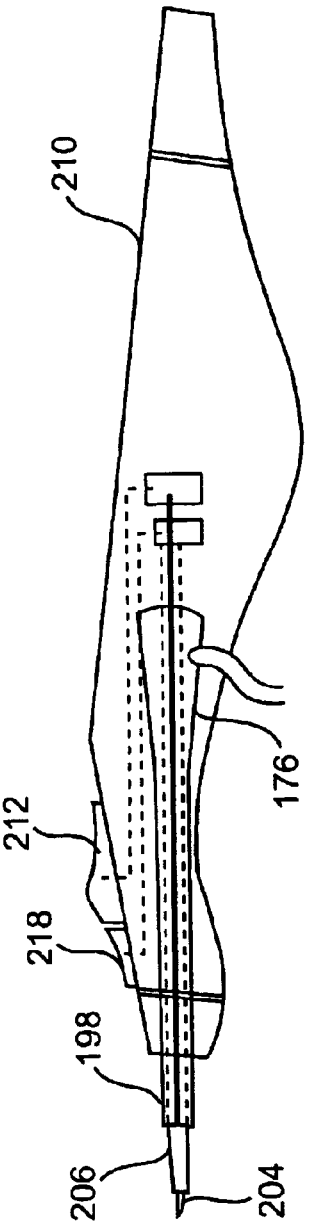
FIG. 22 shows an access device having dual movable mechanisms to independently puncture the vessel wall and advance a sheath into the vessel.

The puncture device 200 shown in FIGS. 21a to c further includes an actuator 202 to advance a perforating member 204 and dilating member 206 relative to a handle 208. This mechanism provides more controllable movement of the perforating member and dilating member. An adaptation of the puncture device is shown in FIG. 22. This puncture device 210 includes dual actuators used to more precisely puncture the vessel wall and advance the dilating member and sheath. When advancing the proximal actuator 212 forward, a perforating member 204, dilating member 206, and the sheath 198 are advanced. However, retracting the proximal actuator 212 pulls only the perforating member. This permits covering the tip of the perforating member within the dilating member after obtaining access through the vessel wall. Since the perforating member is movable relative to the dilating member, a hemostatic valve is formed between the perforating member and dilating member to prevent blood from flowing back through the gap between the perforating member and dilating member. Pushing the distal actuator 218 advances the dilating member and sheath. This permits advancing the dilating member and sheath into the vessel without the risk of puncturing the opposite side of the vessel or damaging adjacent anatomy with the perforating member.

More actuators may be added to the puncture device or the operation of the illustrated actuators may be modified. For example, one actuator may be used to facilitate advancing a guidewire through the perforating member and dilating member once access into the vessel has been obtained. A single actuator may be used to advance the perforating member beyond the dilating member when advanced; this actuator would also be spring-loaded so the resting position of the perforating member is such that the tip is covered inside the dilating member.

Figure 23A:
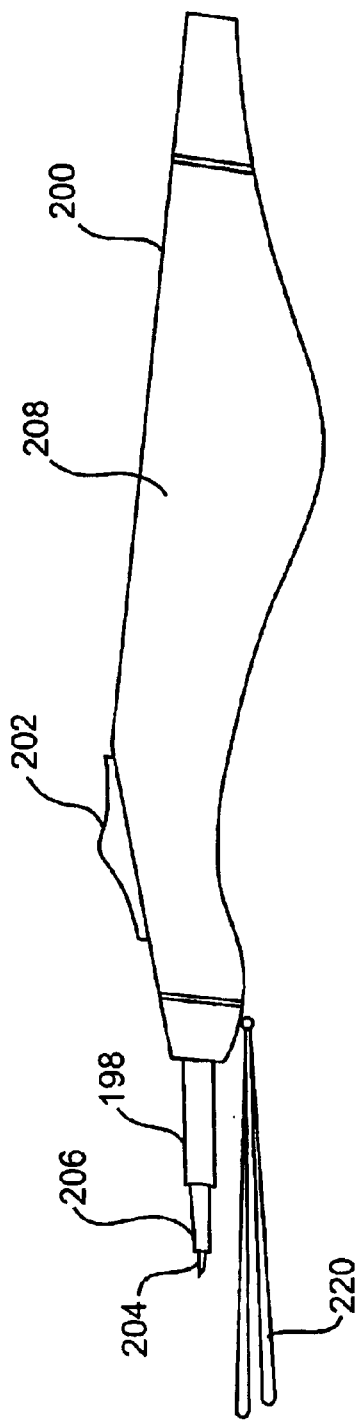
FIGS. 23a and b show the access device of FIG. 21a incorporating a stabilizing structure.
Figure 23B:
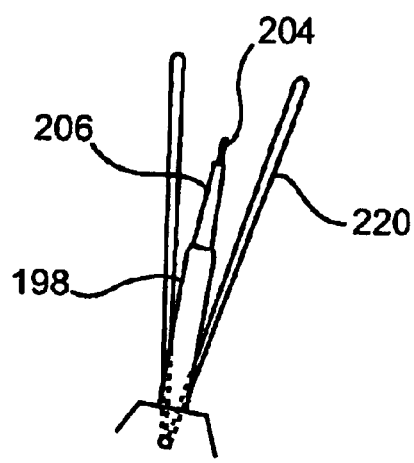
Figure 24:
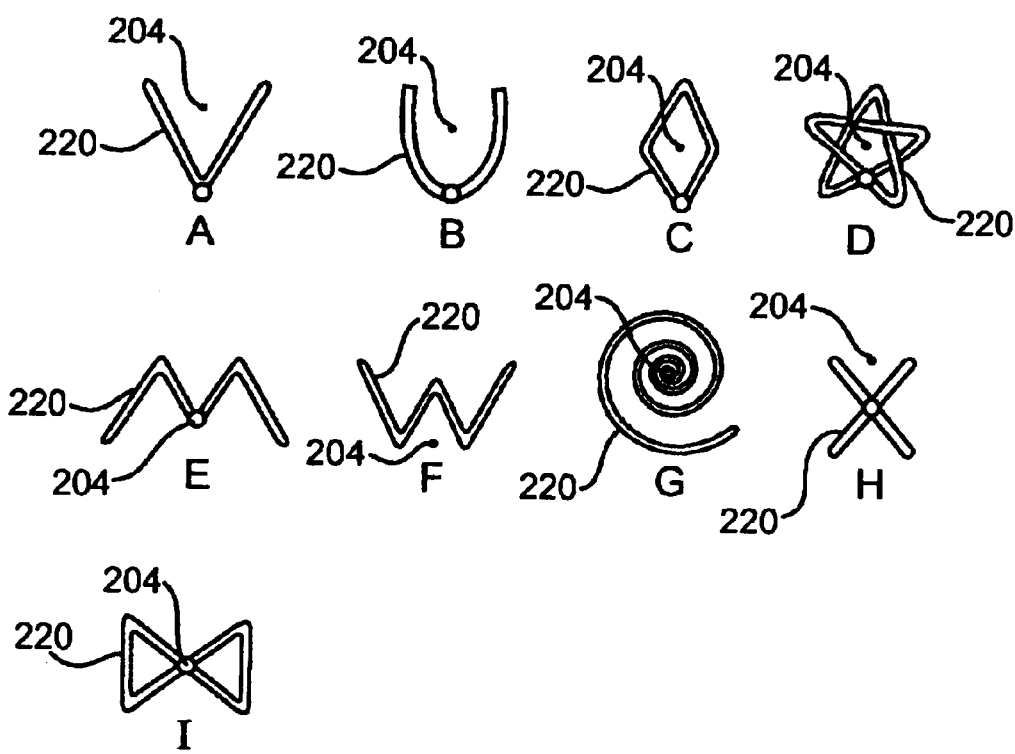
FIGS. 24a to i show the top views of alternative stabilizing structures.

Another feature that may improve the performance of the puncture device is a stabilizing extension. The stabilizing extension 220 shown in FIGS. 23a and b is formed from two legs shaped into a "V". The legs may be fabricated from a metal or polymer and have a circular, elliptical, or rectangular cross-section. The stabilizing extension 220 is designed to decrease the movement of the vessel relative to the puncture device. This is especially important when accessing the coronary vessels. Several alternative configurations for the stabilizing extension are shown in FIGS. 24a to i. Alternative stabilizing extensions, as shown in FIGS. 24h and i, may be configured to fit around the vessel to better stabilize the puncture device relative to the host vessel.

Figure 25:
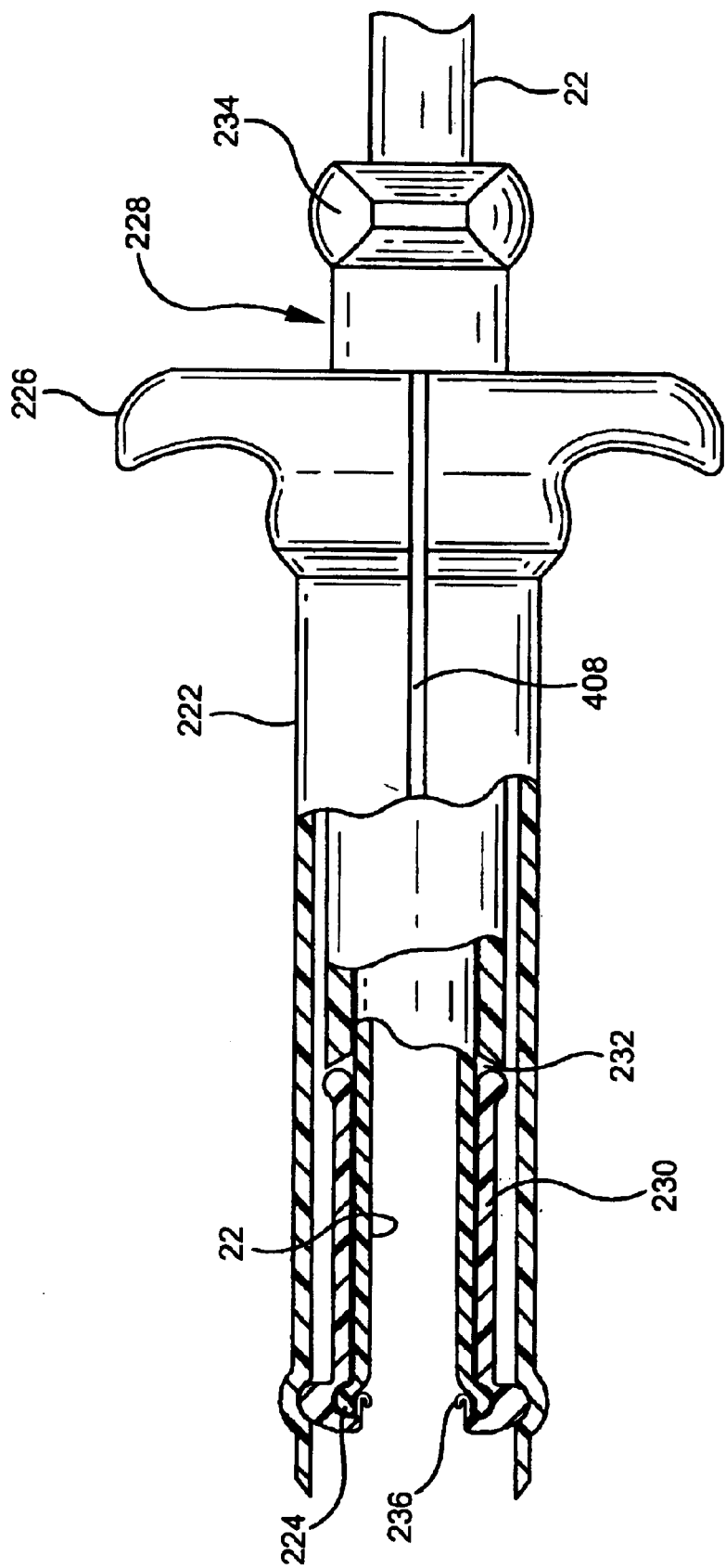
FIG. 25 shows a delivery system in accordance with an embodiment of the invention.

As shown in FIG. 25, a sheath 222 may be fabricated with at least one groove 224 (or a slit or series of perforations) formed along the tube and hub 226 to provide a guide to tear-away the sheath along at least one side, after securing the bypass graft to the vessel wall. Alternatively, the sheath may include a section of tubing material already split into at least two sections such that the sheath tubing tends to continue to split into two pieces as the two sections are pulled apart. The ability to split is essential to removing the sheath from around a bypass graft 22 when the sheath is unable to slide past the opposite end of the bypass graft. When incorporating supporting material into a tear-away sheath to improve column strength, this material should ensure the sheath may be split along the grooves, slits, or perforations formed in the sheath. This supporting material may be fabricated into two braided sections, or other support member sections oriented on opposite sides of the sheath such that the grooves reside along the spaces between the braided sections. Alternatively, the supporting material may be strands of wire (stainless steel, nylon, etc.) laminated between layers of sheath material and oriented axially along the longitudinal axis of the sheath.

A plunger 228 is designed to insert bypass graft 22 and a fitting 230 as an attached unit, therefore it includes a lumen to pass bypass graft 22 while inserting the fitting into the host vessel. A plunger is essential when inserting biological bypass grafts or synthetic bypass grafts that do not have adequate column strength to be pushed through the hemostatic valve of the sheath. In addition, the plunger protects the bypass graft while inserting the bypass graft through the tubing and hemostatic valve of the tear-away sheath. After use of the plunger to advance one side of the bypass graft at a first vessel location, it must be removed. The plunger may be retracted beyond the opposite end of the bypass graft, or the plunger is split along at least one groove 232, slits, or perforations incorporated along the side(s) of the plunger. Then a plunger similar to plunger 228 is used to insert the opposite end of the bypass graft, attached to a fitting, through a second sheath inserted at a second vessel location. After attaching the second end of the bypass graft to the host vessel, the plunger is contained between the ends of the attached bypass graft and must be removed by tearing the plunger along the groove, slit, or series of perforations. The tear-away groove must permit splitting the plunger wall and a hub 234 along at least one side to remove the plunger from around the bypass graft. To facilitate removal from around the bypass graft, the plunger (and tear-away sheath above) preferably incorporates grooves, slits, or perforations on two sides of the plunger to enable separating the tube and hub.

As shown in FIG. 25, a retaining ring 236 may also be used to bond a bypass graft to the fitting from the interior of the fitting 230. In this embodiment, the fitting has an internal groove 224 to accept retaining ring 236 which is wound into a smaller diameter and inserted inside the bypass graft and fitting combination. When the constrained retaining ring is released, it expands to compress the bypass graft 22 between the retaining ring and fitting.

Figure 26:
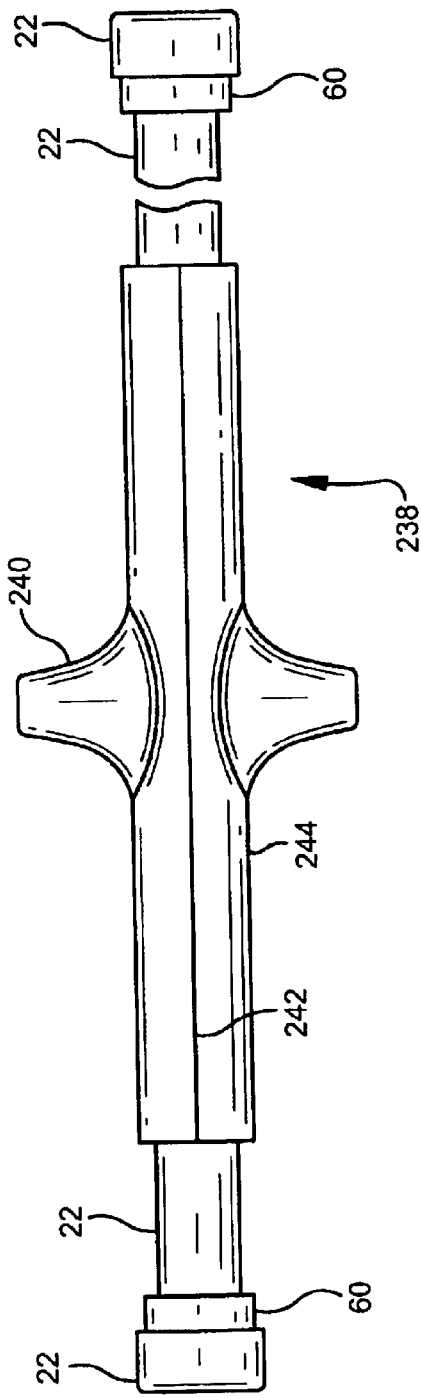
FIG. 26 shows a two-way plunger used to deliver the bypass graft and fitting combination through the sheath and into the host vessel.

FIG. 26 shows a bypass graft assembly containing fittings 60 already attached at bypass graft 22 ends and an alternative plunger 238 preloaded onto the bypass graft. This plunger is designed with the hub 240 located at the middle of the plunger to facilitate inserting both ends of the bypass graft and attached fittings without having to remove and reposition the plunger before inserting the second end of the bypass graft. The plunger has grooves, slits, or perforations 242 along at least one side of a plunger tube 244 and hub 240 to permit removal of the plunger after positioning and attaching the bypass graft at both ends.

Figure 27A:
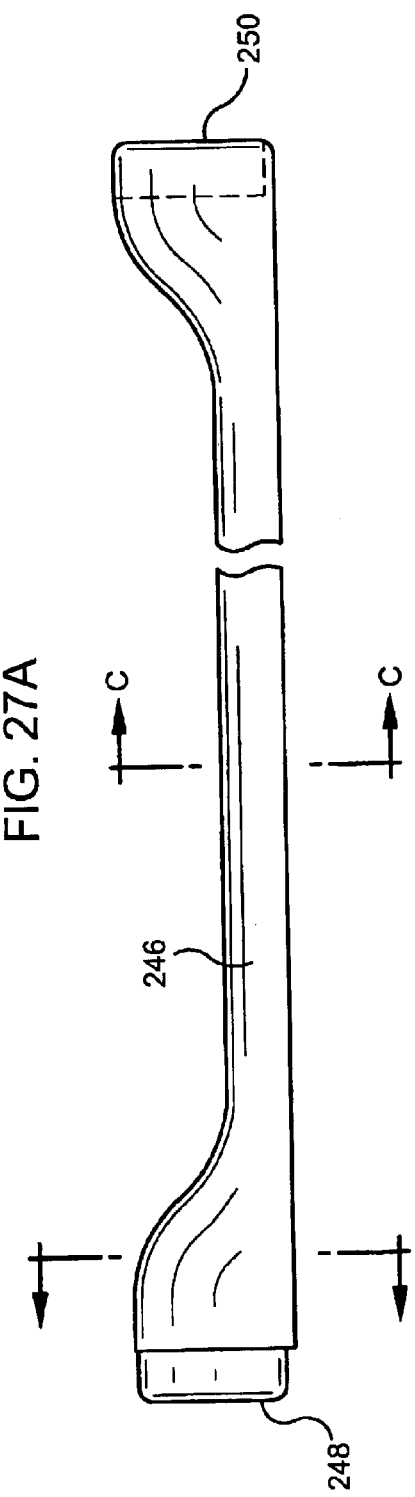
FIGS. 27a to c show an alternative plunger embodiment.
Figure 27C:
Figure 27B:
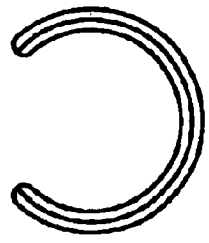

Another plunger embodiment is shown in FIGS. 27a to c. This plunger 246 includes an axial slot through the entire length of the plunger. The slot enables pulling the plunger from the side of the bypass graft when removing the plunger and permits pressing the plunger over the side of the bypass graft when placing the plunger over the bypass graft. One end 248 of the plunger has a short length stepped down to form a smaller outer diameter that fits inside the inner diameter of the fitting and provides a stable anchor to insert and manipulate the fitting during delivery of the bypass graft and fitting combination into the vessel. The other end 250 of the illustrated plunger has the inner diameter reamed out and notched for a short length to fit over the outer diameter of the bypass graft and fitting combination during manipulations. The notched region can alternatively be configured to extend a sufficient length such that the plunger covers the fitting exterior, to protect the fitting during insertion through the sheath. This especially important when inserted end-side fittings that require constraining the petals in a reduced diameter profile for advancing the fitting and bypass graft combination through the sheath. This also helps constrain foldable or compressible fittings in their reduced diameters for insertion through a sheath having a smaller diameter than the expanded diameters of the fittings. Since this plunger maintains its integrity upon removal from the bypass graft, it may be used to deploy multiple bypass graft and fitting combinations.

Figure 28:
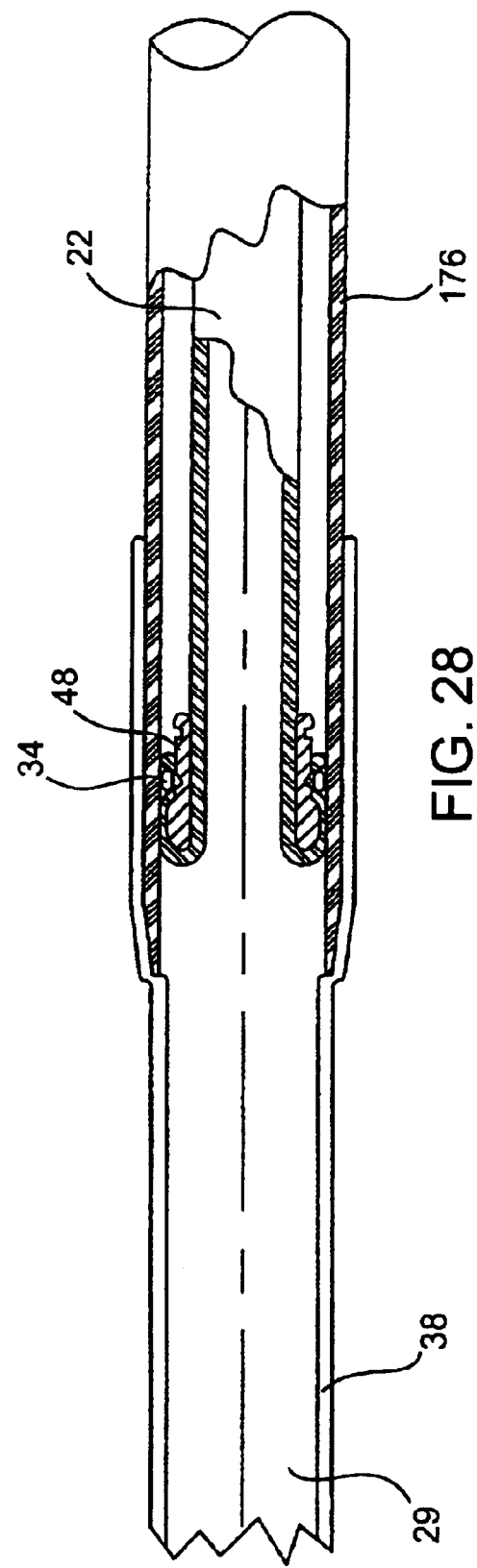
FIG. 28 shows a bypass graft and fitting combination being inserted through a sheath in accordance with a delivery system embodiment of the invention.

FIG. 28 is an enlarged view of sheath 176 inserted into host vessel 29 with dilator 174 removed, and with bypass graft 22 everted about fitting 48 and retained by ring 34.

For situations where blood flow is occluded and an incision has been made through the vessel wall, a modified hockey stick introducer may be used to insert the bypass graft and fitting combination into the host vessel. FIGS. 29a to f show a "hockey stick" introducer 252 having a tapered distal end and a partially enclosed body. This hockey stick introducer is advanced through the incision and expands the vessel wall so the bypass graft and fitting combination may be advanced through the hockey stick introducer lumen and into the host vessel without catching the top part of the fitting on the vessel wall. This is especially important when the bypass graft and fitting combination has an outer diameter larger than the inner diameter of the vessel where the host vessel must be expanded to insert the bypass graft and fitting combination. The hockey stick introducer may incorporate an extension perpendicular to the longitudinal axis that provides a handle to manipulate the hockey stick introducer. In addition, the hockey stick introducer may incorporate at least one spring-loaded jaw to grab the host vessel wall after access has been obtained and permit manipulating the expanded host vessel by using the hockey stick introducer. This is especially useful when reattaching severed vessels, which requires significant manipulations while repositioning the host vessel ends for bonding.

Additional Delivery System Features

As previously described in U.S. application Ser. No. 08/966,003 filed Nov. 7, 1997, the needle and dilator may incorporate a number of additional features to facilitate positioning at the host vessel. A number of sensors may be placed within the tapered region of the dilator such that they face axially or laterally with respect to the axis of the dilator lumen. As a result, imaging modalities may be directed forward or around the periphery of the dilator. For both configurations, the sensors may be oriented around the dilator at known angular increments. Sensors used to position the delivery system include ultrasonic transducers, such as those fabricated from piezoelectric material, infrared transducers, or fiberoptics. Four ultrasonic transducers may be placed around the dilator separated by 90 degrees to provide a 3-dimensional interpretation of anatomic structures in front of the dilator to better detect the host vessel. Conventional phased array imaging modalities may be used to derive images extending distal to the dilator or around the dilator circumference. Sensors may be placed at the distal end of the needle to facilitate positioning the needle at the target vessel location. These sensors may be used in concert with the dilator sensors to provide better imaging resolution and determine the location of the needle tip relative to the end of the dilator.

Another feature which may be used in the dilator and needle is the inclusion of steering, unidirectional or bi-directional. A steering mechanism may be positioned within the sheath, dilator, and/or needle. Typically, the steering mechanism consists of a pull-wire terminating to a flat spring (constrained with a thin walled tubing such as PET or PTFE) or collar and incorporated in the sheath, dilator, or needle having a more flexible distal section compared to the proximal tube body. When tension is placed on the pull-wire, the sheath, dilator, or needle is deflected into a curve. This helps direct the delivery system to the target vessel location. The pullwire may be wound, crimped, spot welded and/or soldered to the flat spring or collar placed in the sheath or dilator. This provides a stable point within the sheath or dilators for the pullwire to exert tensile force thus steer the sheath or dilator. To incorporate steering in the needle, the pullwire may be spot welded or soldered to one side of the needle hypotubing. The proximal tube body of the sheath or dilator may be reinforced by incorporating a helically wound wire within the tubing extrusion to provide column support from which to better deflect the distal section.

To perform an end-side anastomosis in accordance with the invention, a delivery system, previously described, may be used to insert the fitting partially into the vessel through a small puncture in the vessel wall. As shown in FIG. 30, one end-side embodiment incorporates a retaining ring 254 similar to ring 140 or 143 having a wide cross-section designed to mate with the distal end of the fitting after being advanced over the fitting. The diameter of the retaining ring is enlarged with an expanding tool (e.g. tool 108 or 160) while the fitting is slightly retracted. With the vessel snuggly around the distal end of a fitting 60, the retaining ring is released securing the vessel wall at the distal end of the fitting. Fittings such as that shown in FIG. 30 may incorporate a notch 56 near the distal end to help hold the vessel wall around the fitting while retracting the fitting and positioning the retaining ring. This attachment methodology inherently places the distal end of the fitting flush with the side of the vessel to help prevent disrupting fluid flow through the host vessel, especially at the attachment site of the fitting. The retaining ring may be further secured by placing a suture 80 through eyelets 100 and tying the ends of the retaining ring closed.

FIG. 30 shows a fitting 256 with barbs 257 to prevent axial movement of the bypass graft 22 relative to the fitting. Alternatively, as shown in FIG. 18, notches may be fabricated in the fitting. The barbs or notches reinforce the compression fit between the bypass graft 22 and the fitting, achieved by positioning retaining rings in the indents defined by the barbs or notches.

Figure 33A:
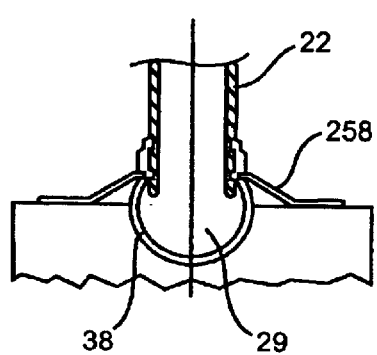
FIGS. 33a and b show a retaining ring incorporating a support mechanism that may be sutured to tissue away from the host vessel.
Figure 33B:
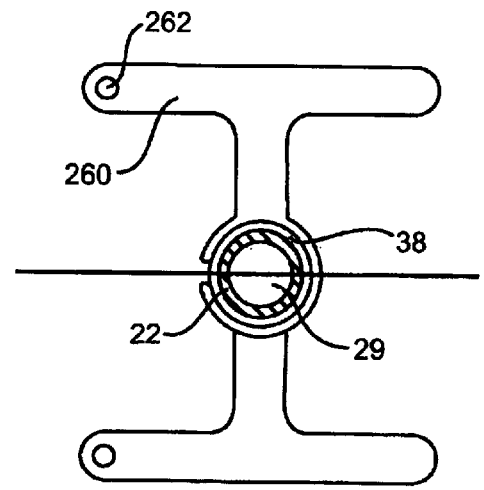

Another end-side fitting embodiment attaches an everted bypass graft to a vessel wall 38. Bypass graft 22 is everted around the distal end of fitting 60 as previously described; the bypass graft is then secured to the fitting using a retaining ring. The bypass graft and fitting are partially inserted through vessel wall 38 using the deployment system described above. The bypass graft and fitting combination is retracted thereby pulling the vessel wall located around the fitting, proximal. A second retaining ring is opened by enlarging its diameter with an expanding tool and advanced over the section of the vessel wall contacting the fitting. The retaining ring is released closing around the vessel wall and fitting. The retaining ring is positioned such that it resides in the notched area of the fitting to prevent axial motion as discussed above. A secondary bond may be created between the vessel wall and the fitting by placing a retaining ring 136 (FIGS. 12a and b) around the distal flared end of the fitting. Alternatively, suture may be used to further secure the vessel wall to the fitting by wrapping the suture around the vessel wall and fitting distal to the retaining rings. As shown in FIGS. 33a and b, a retaining ring 258 may alternatively include extensions 260 with holes 262. The operator can suture or staple this retaining ring to a tissue surface outside the vessel providing an anchor between the retaining ring and the host vessel.

Figure 31:
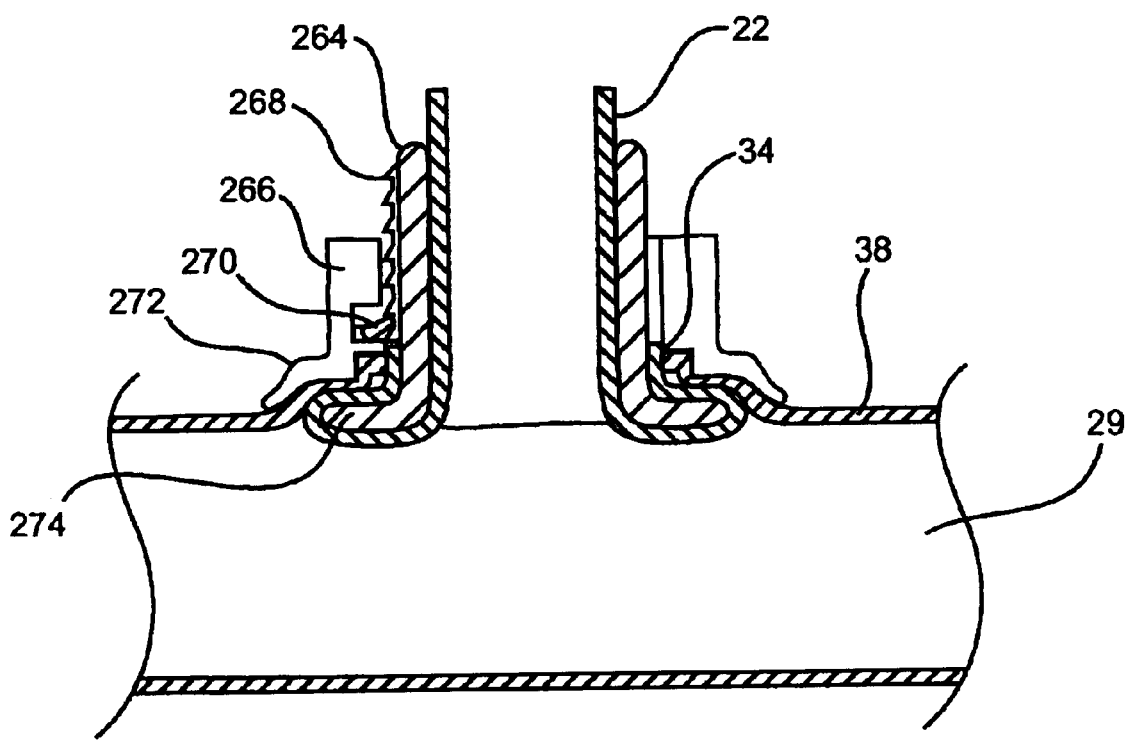
FIG. 31 shows a fitting embodiment using a latching mechanism to secure a bypass graft to a vessel wall.

An embodiment for producing an end-side anastomosis especially designed for large diameter vessels (e.g. the aorta) is shown in FIG. 31. After the bypass graft 22 and fitting 264 are inserted partially through the vessel wall, a self-locking component 266 is advanced over teeth 268 incorporated in the fitting. A ratcheting mechanism 270 prevents the self-locking component from dislodging from the fitting. The distal end 272 of the self-locking component is designed to match a flared end 274 of the fitting. Therefore, as the self-locking component is further advanced relative to the fitting, the vessel wall becomes compressed between the self-locking component and the flared end of the fitting to produce a fluid tight, secure bond. This embodiment is capable of bonding the vessel wall to bypass graft 22 and fitting 264 after the bypass graft has been everted around the fitting.

Figure 32A:
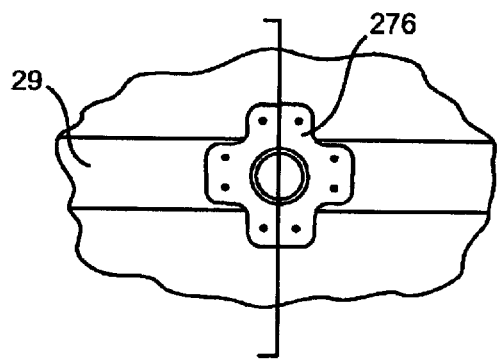
FIGS. 32a to c show a bypass graft secured to a host vessel using end-side fittings in which a flange is used to reinforce the attachment point.
Figure 32B:
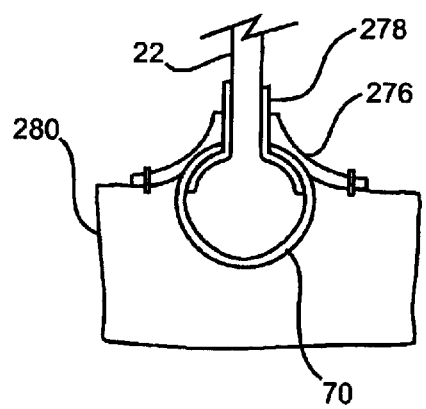
Figure 32C:
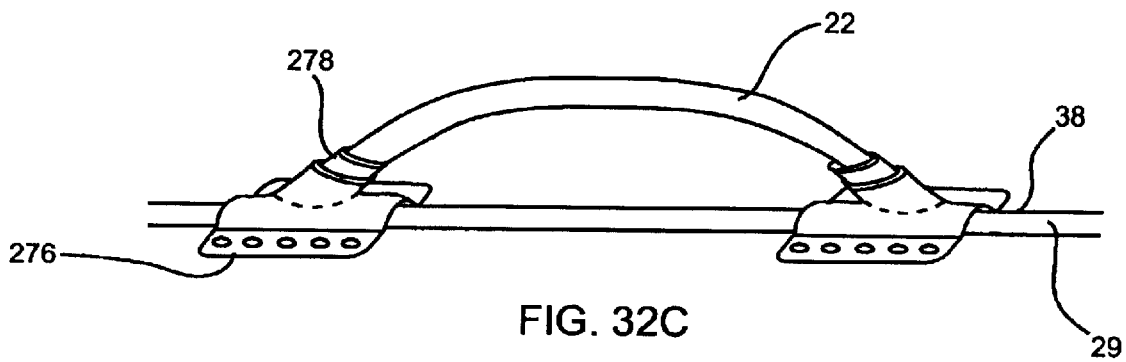

An adaptation of the end-side fitting above, shown in FIGS. 32a and b, uses a flange 276 to secure the vessel wall to the bypass graft. A fitting 278 having a distal flared end is inserted through a puncture into the vessel. Flange 276 mates with the distal, flared end of the fitting, is advanced over the fitting and is secured by suturing or stapling the flange to a tissue surface 280. In this position, the vessel wall is compressed between the fitting and the flange providing a fluid tight seal between the bypass graft and the host vessel. As shown in FIG. 32c, fitting 278 and flange 276 can orient the bypass graft at selected angles relative to the host vessel. An alternative flange 282, shown in FIGS. 34a to d, is inserted into the interior of the vessel and is attached to the vessel wall. The flange contains holes 284 enabling the operator to suture or staple the flange to the vessel wall. The operator locates the holes relative to the puncture site through the vessel wall, advances a needle through the holes and back outside the vessel wall where the suture is tied thereby attaching the flange to the vessel wall. FIG. 35 shows a clip to 286 that can be used to secure flange 276 in lieu of a suture or staples.

Figure 36A:
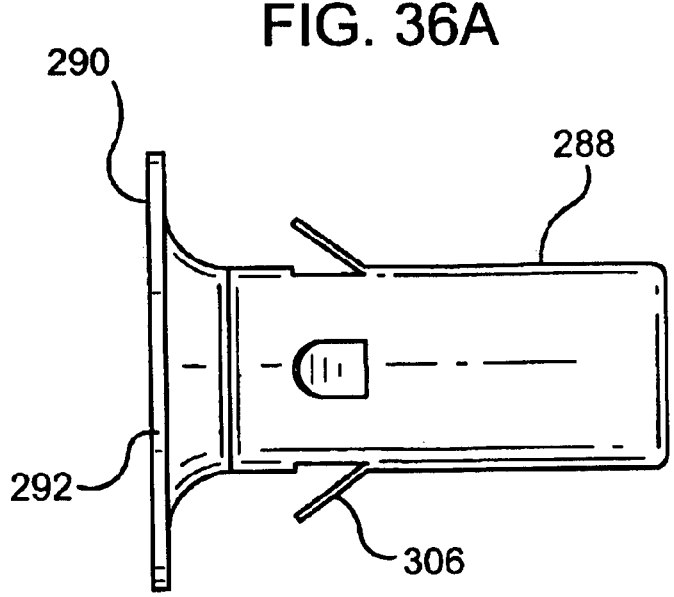
FIGS. 36a to e show an end-side fitting that may be delivered past a vessel wall without the need for a sheath.
Figure 36B:
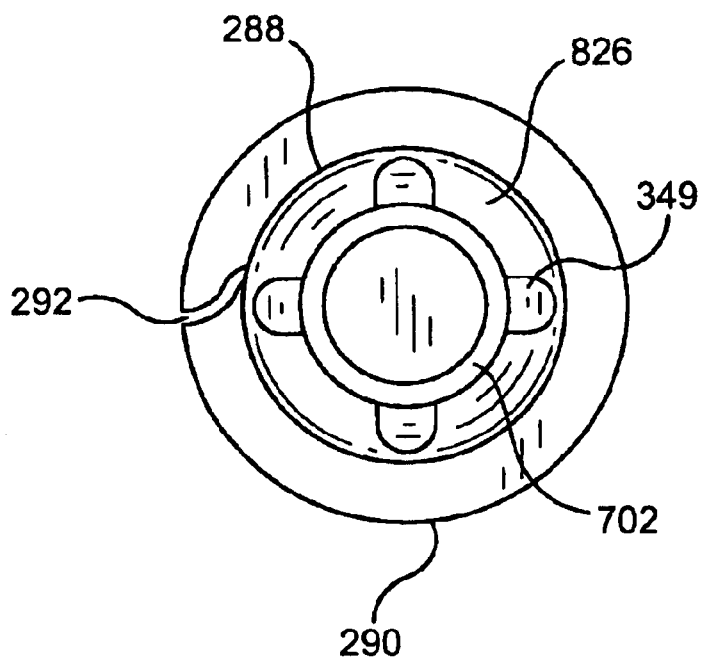
Figure 36C:
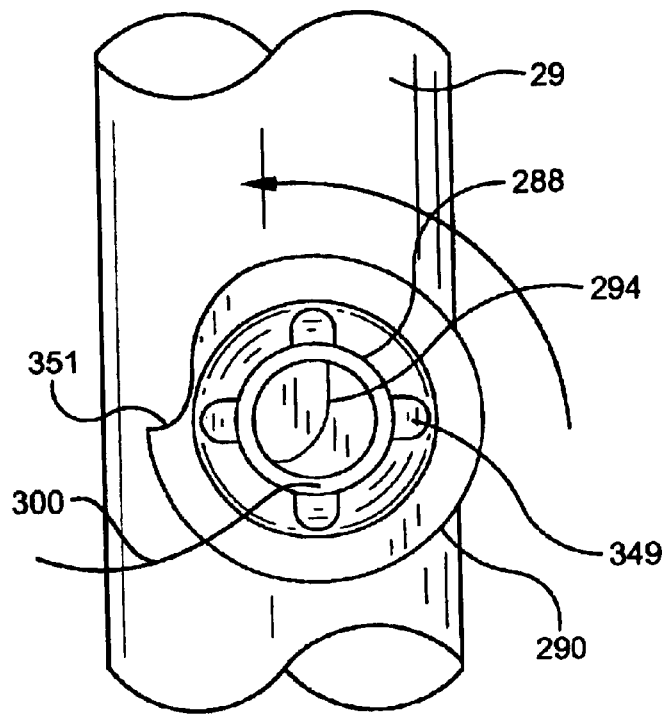
Figure 36D:
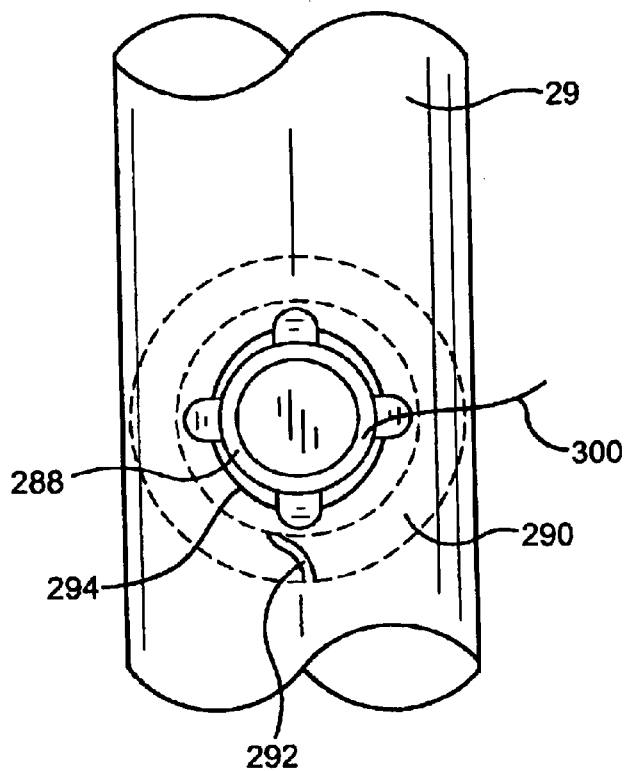
Figure 36E:
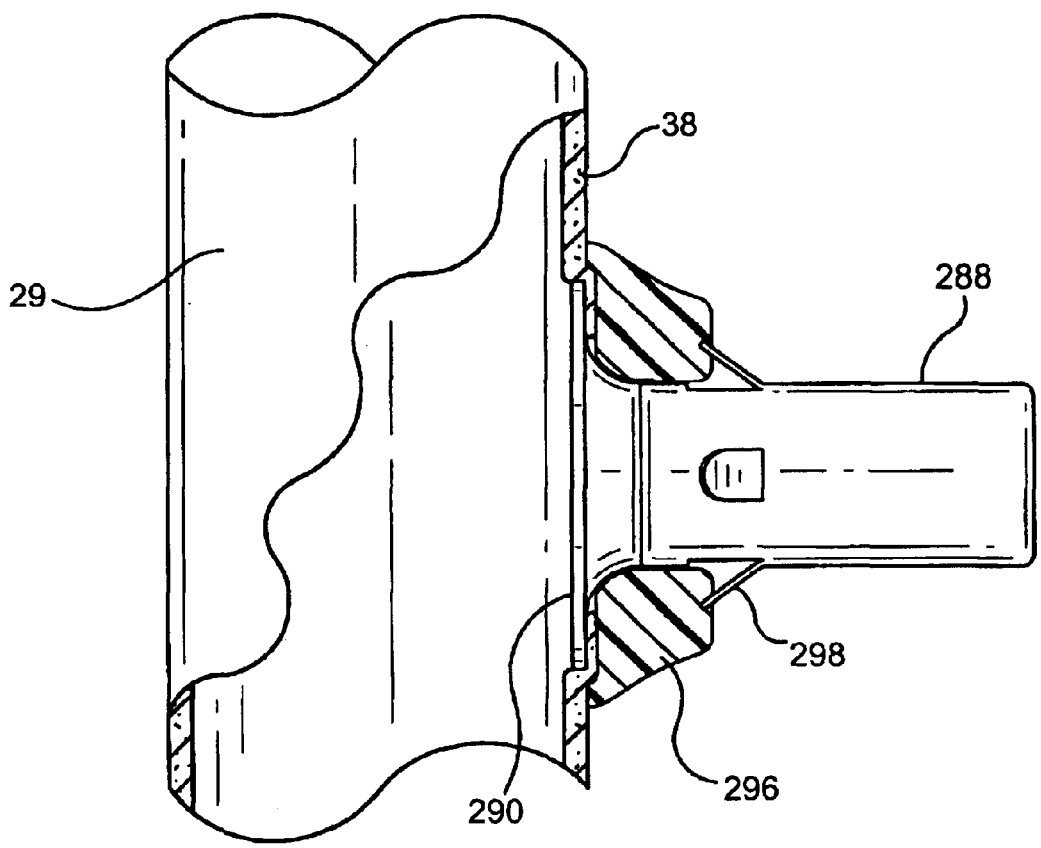

FIGS. 36a to e show an additional embodiment for producing an end-side anastomosis that compresses the vessel wall between two fitting components. A fitting 288 incorporates a flared distal region 290 having a slot 292 that defines two edges. The slotted distal end of the fitting is inserted through a puncture 294 of the vessel wall by positioning the edge of the slotted fitting at the puncture site, angling the distal flared region so the edge may be further advanced through the vessel wall, and rotating the fitting. Upon sufficient rotation of the fitting, the entire flared region of the fitting is advanced into the interior of vessel 29, as shown in FIG. 36d. Then a compression ring 296 is positioned over the fitting and past tabs 298 thereby compressing the vessel wall between flared distal end 290 and compression ring 296, as shown in FIG. 36e. For some applications, a conductive lead 300 is attached to fitting 288.

Figure 37A:
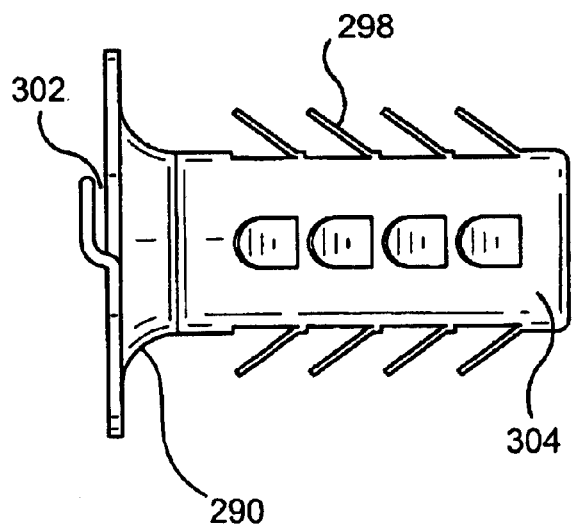
FIGS. 37a to e show alternative end-side fitting that may be delivered past a vessel wall without the need for a sheath.
Figure 37B:
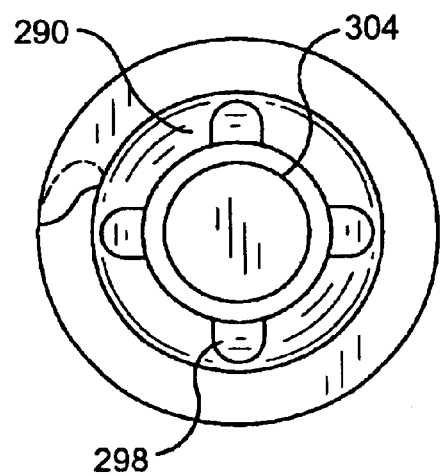
Figure 37C:
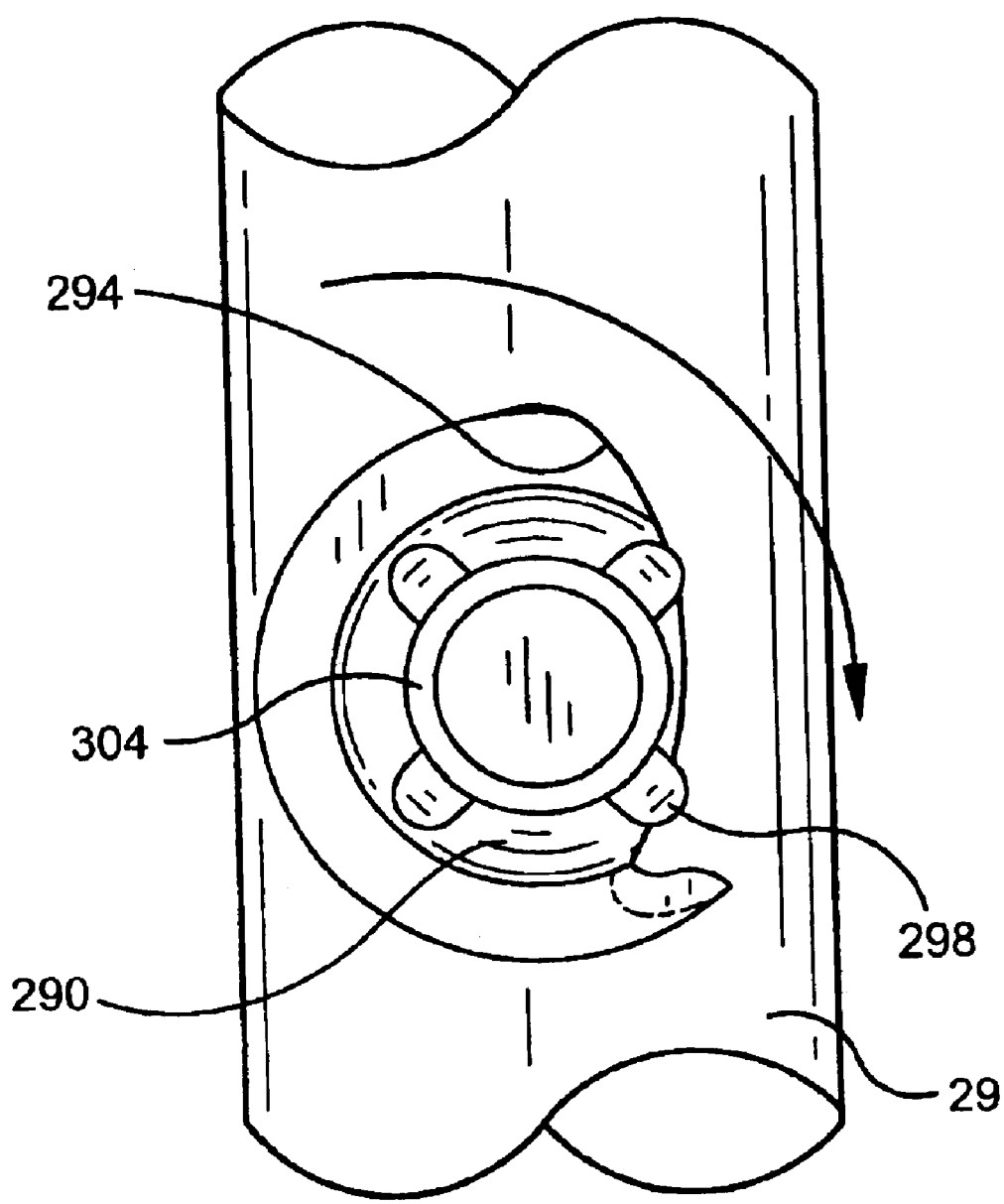

An adaptation of the screw-in fitting embodiment above is shown in FIGS. 37a to c. Here an edge 302 of flared end 290, separated by a slot, overlap to ensure a fluid tight fit in the slotted region after deploying the fitting and securing it to the vessel with a compression ring (not shown). As shown in FIG. 37c, the lower edge is advanced through the puncture site 294, and fitting 304 is rotated to advance the distal, flared end of the fitting into the vessel. Once in the vessel, a compression ring is advanced over the fitting and is locked in place with tabs 298 thereby securing the vessel wall between the distal, flared end of the fitting and the compression ring. The edges for this fitting embodiment are biased to define a slot and facilitate rotation through the vessel wall, and overlap such that they contact enhancing the leak resistance after the compression ring has been used to secure the fitting to the vessel wall. Fitting 304 includes multiple rows of tabs 298 to accommodate various sized vessel walls; this feature is important when treating vascular diseases associated with thickening of the vessel wall.

Figure 37D:
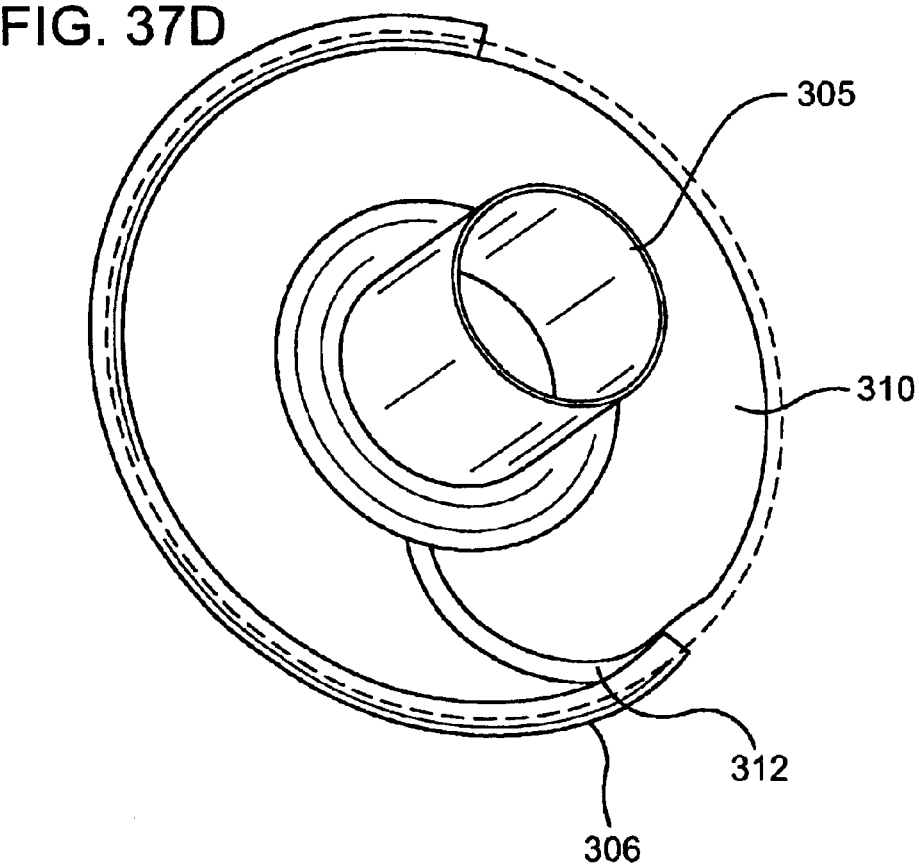
Figure 37E:
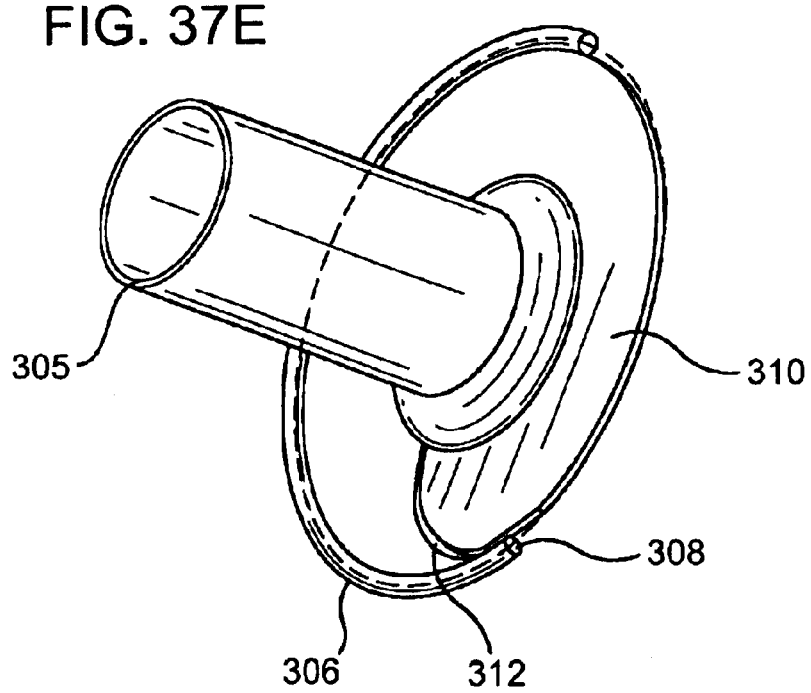

An alternative embodiment screw-in fitting 305 is shown in FIGS. 37d and e. In this configuration, a guidewire is inserted through the vessel wall and into the interior of the host vessel by puncturing the vessel wall with a needle and inserting the guidewire through the lumen of the needle; the needle is removed from around the guidewire after inserting the guidewire through the vessel wall. An insertion tubing 306 containing a central lumen 308 follows the periphery of the flared end 310 and is adapted to pass a guidewire. The guidewire is fed through the insertion tubing to facilitate screwing the fitting past the vessel wall. The insertion tubing extends approximately 40% to 80% around the flared end circumference. Alternatively, the insertion tubing may be configured in sections extending around the circumference of the flared end so the physician may determine how far around the flared end the guidewire must extend to rotate the flared end past the host vessel wall. A slot 312 through the distal flared end is adapted to accept the thickness of the vessel wall and enables screwing the fitting through the vessel wall. As the screw-in fitting is advanced over the guidewire and rotated, the fitting simultaneously expands the puncture through vessel wall and inserts more of the distal flared end into the vessel interior. Once the flared end of the fitting is inserted into the host vessel interior, the guidewire is removed and the fitting is secured to the vessel wall using a compression ring as described above, applying adhesives to the bond, suturing the fitting, or other bonding process.

Figure 38A:
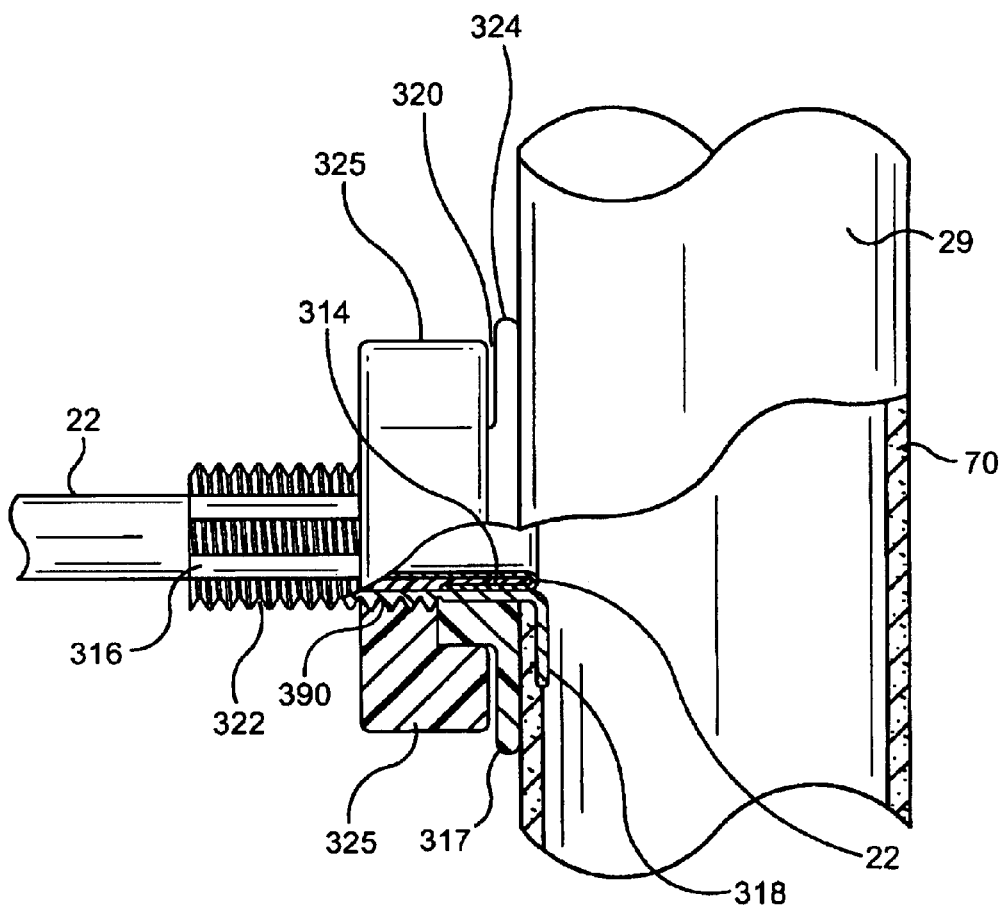
FIGS. 38a to c show an end-side fitting, incorporating a retaining ring with petals, designed to compress the host vessel wall between two fitting components.
Figure 38B:
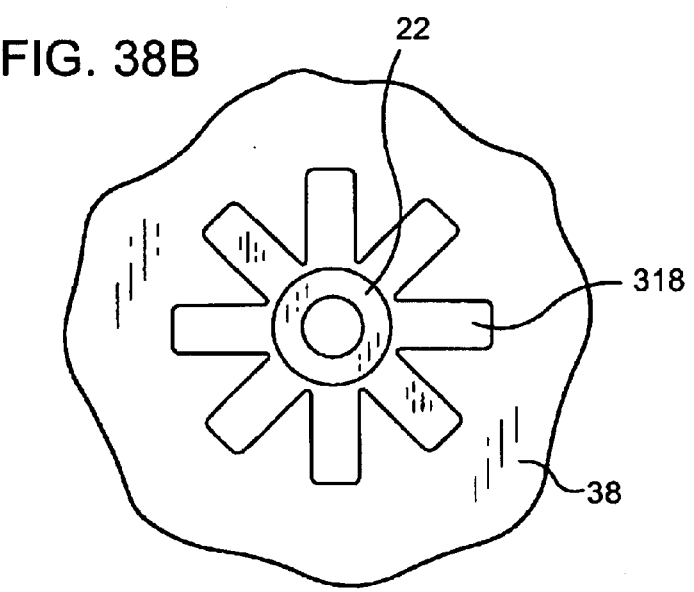
Figure 38C:
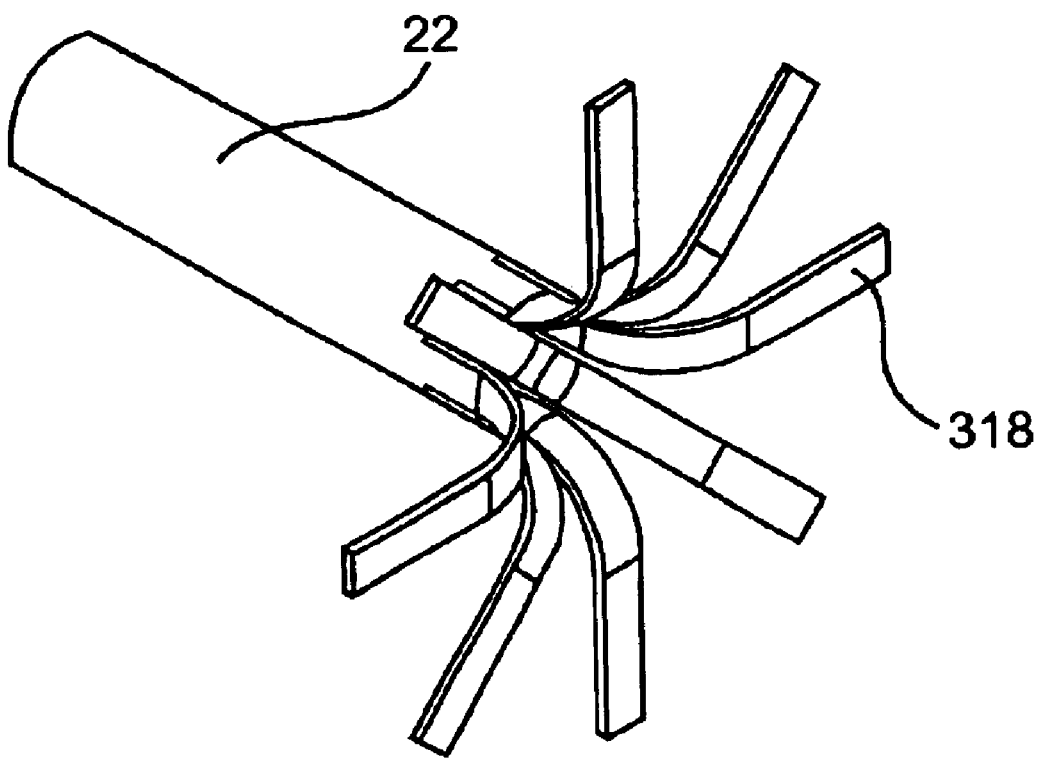

An alternative embodiment for performing an end-side anastomosis is shown in FIGS. 38a to c. The embodiment shown in FIGS. 38a to c includes a fitting 314 with a bypass graft 22 everted over the distal end of the fitting. A retaining housing 316 is used to secure the bypass graft to the fitting. This retaining housing permits radial expansion during placement over the bypass graft and fitting, yet has a preshaped memory to compress around the bypass graft and fitting thereby securing the bypass graft to the fitting. This retaining housing has petals 318 at its distal end, which compress into a low profile during delivery through a sheath and expand radially once deployed inside vessel 29. The petals extend at an angle between 30 and 150 degrees from the axis of the retaining housing. Petals 318 can extend at an angle larger than 90 degrees from the retaining housing axis to increase the force exerted by the petals against the vessel wall when the retaining housing is retracted against the host vessel wall.

The number of petals 318 incorporated in the retaining housing design depends on the size of the bypass graft and the size of the host vessel. In this illustrated embodiment, eight petals are used. After advancing the fitting through a sheath and past the vessel wall, the fitting is advanced beyond the end of the sheath and is no longer constrained by the sheath, thus expands towards its resting configuration. Then the bypass graft and fitting combination is gently retracted to engage the interior vessel wall with the petals. For mechanical securing, a compression ring 320 is advanced over the fitting thereby compressing vessel wall 38 between the petals of the retaining housing and the compression ring.

As shown in FIG. 38a, the retaining housing may incorporate threads 322 with which to screw the compression ring and secure the compression ring relative to the retaining housing. The threads are oriented only along the sections of the retaining housing configured to engage the compression ring; the slotted regions enabling the retaining housing to radially expand do not include threads. The compression ring is alternatively locked in place using a ratchet mechanism, adhesives, sutures, or other attachment means to secure the compression ring in place. The compression ring for this embodiment incorporates two components: 1) a distal, flexible o-ring or disk 324 designed to produce a fluid tight seal and prevent damaging the vessel wall by excess compression; 2) a proximal, more rigid locking ring 325 used to maintain the position of the o-ring or disk relative to the vessel wall. The locking ring shown in FIG. 38a is designed to match the threads incorporated in the retaining housing.

Figure 39A:
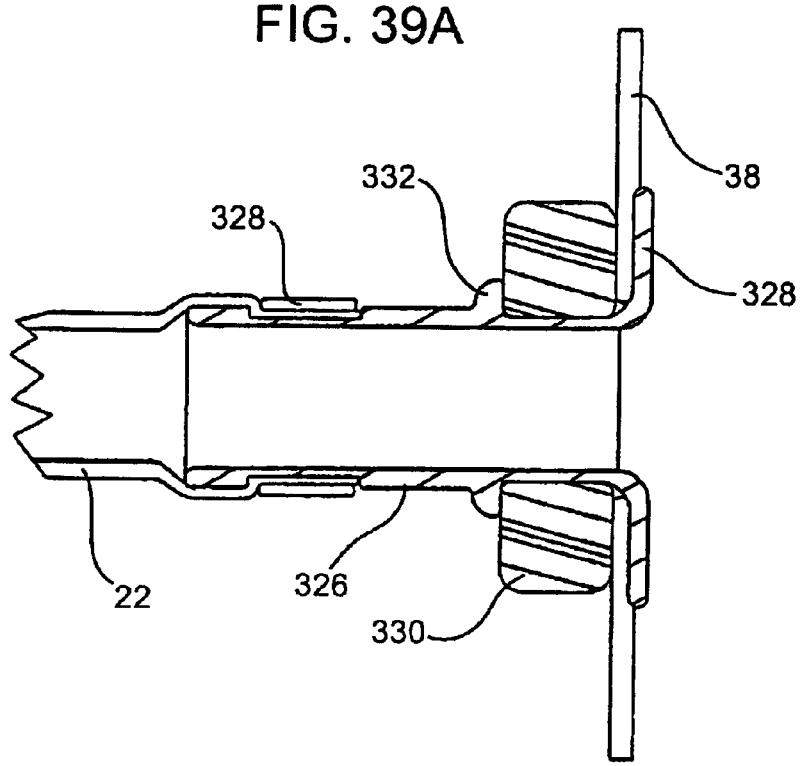
FIGS. 39a to c show an end-side fitting, incorporating a retaining ring with petals, designed to compress the host vessel wall between two fitting components.
Figure 39B:
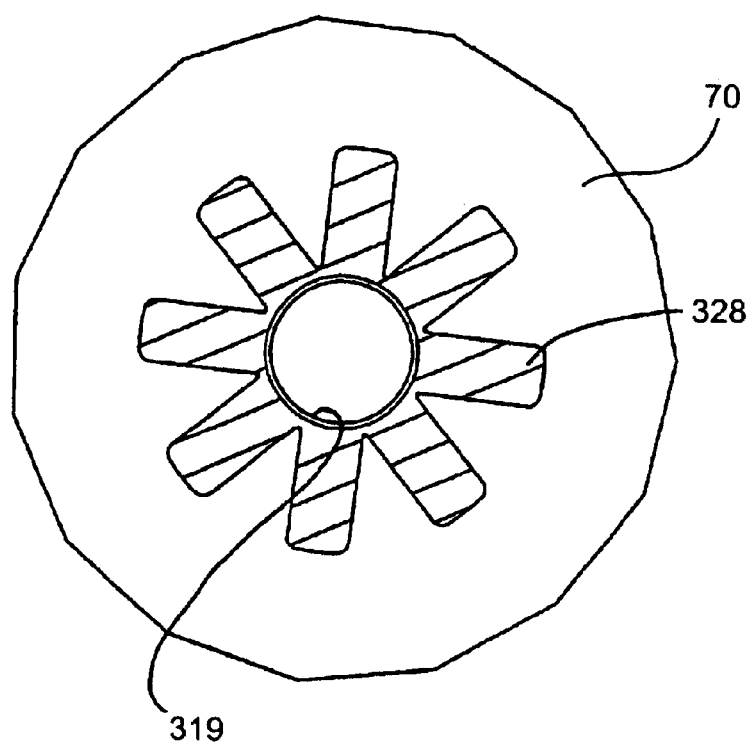
Figure 39C:
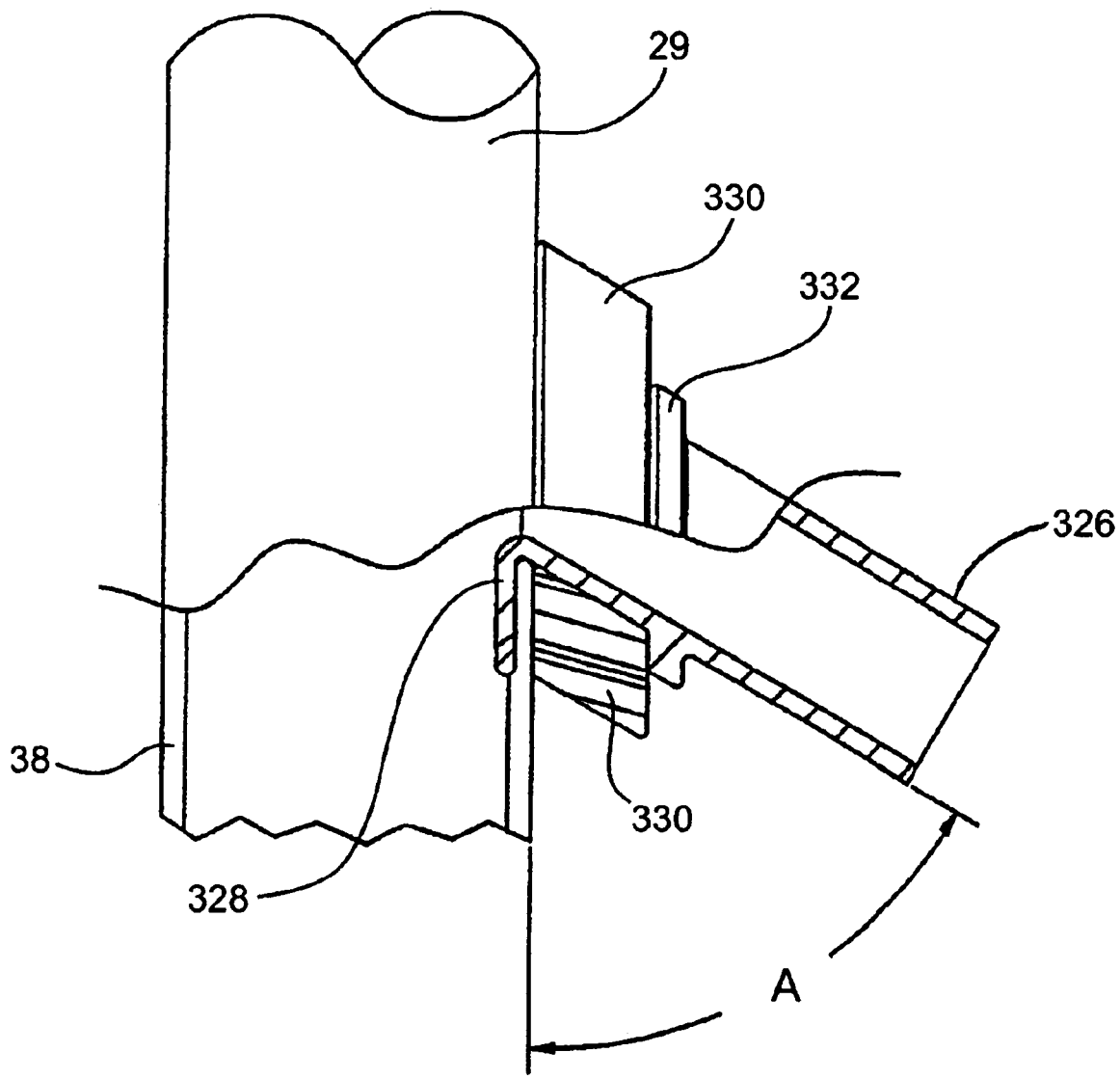

FIGS. 39a to c show another fitting 326 used to produce an end-side anastomosis. In this embodiment, the fitting incorporates petals 328 that collapse into a low profile during delivery through a sheath and extend radially outward once deployed into the vessel interior. In this embodiment, bypass graft 22 is advanced over the outside of fitting 326 and is secured using a retaining ring 329. Alternatively, the fitting is laminated between layers of bypass graft material. A compression ring 330 is advanced over the fitting, after deploying the fitting into the interior of the vessel, and is used to compress the vessel wall between the deployed petals of the fitting and a protrusion 332 on the fitting. This secures the fitting to the vessel wall. As shown in FIG. 39c, the fittings that incorporate petals and the compression rings used to produce end-side anastomoses may be configured to produce an angle (A) between bypass graft 22 and the interior of the host vessel. Like petals 316, petals 328 of fitting 326 extend at an angle between 30 and 150 degrees from the axis of the fitting. The angle of the petals can be chosen to increase the force exerted by the petals against the vessel wall when the fitting is secured using compression ring 330.

Figure 15A:
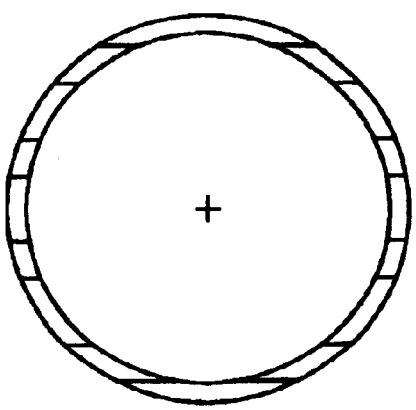
FIGS. 15a to d show alternative expandable, collapsible retaining ring embodiments.
Figure 15B:
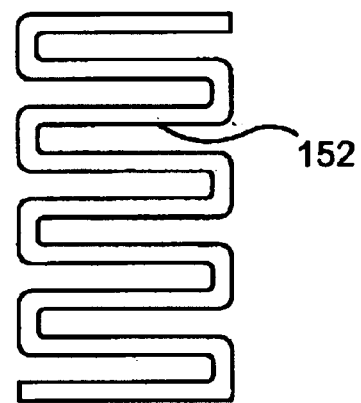
Figure 15C:
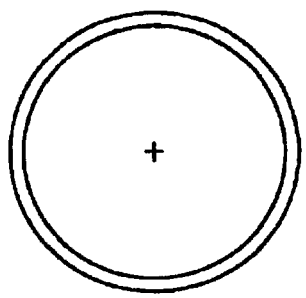
Figure 15D:
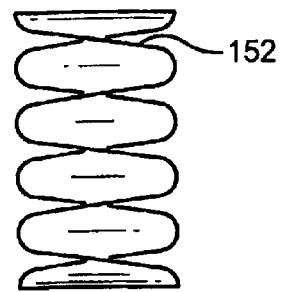
Figure 15E:
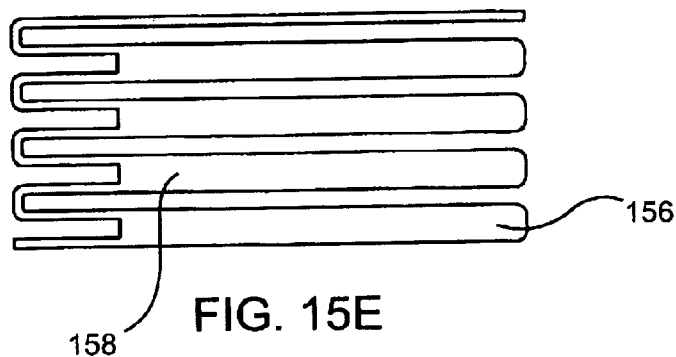
FIGS. 15e and f show an expandable, collapsible retaining ring including petals to make an end-end fitting able to produce an end-side anastomosis.
Figure 15F:
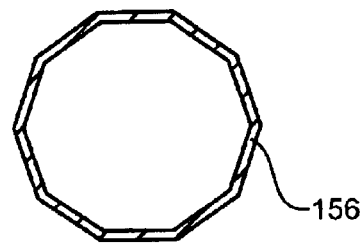
Figure 40A:
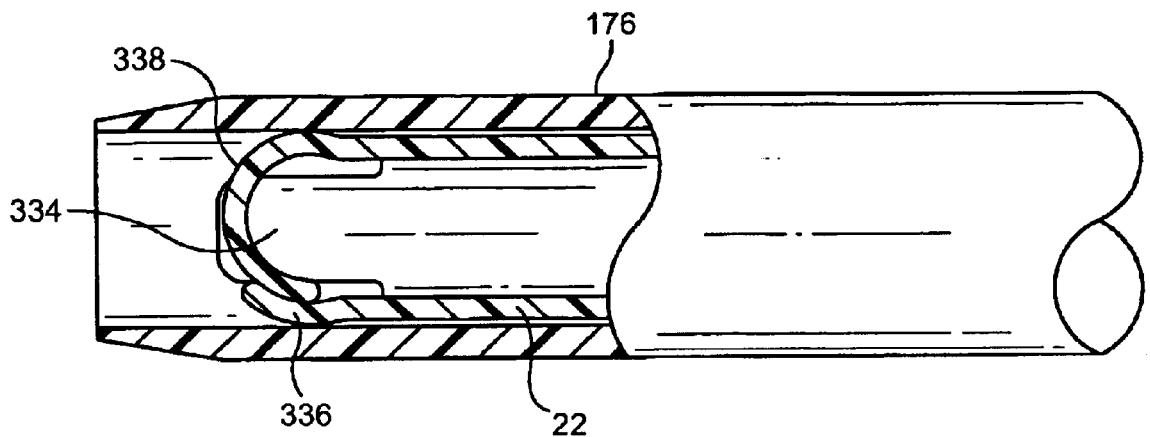
FIGS. 40a to g show an end-side fitting specifically designed for host vessels having small and medium diameters.
Figure 40B:
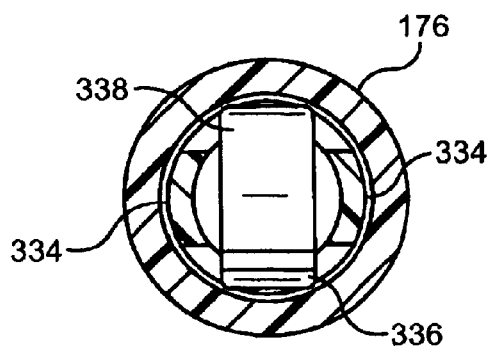
Figure 40C:
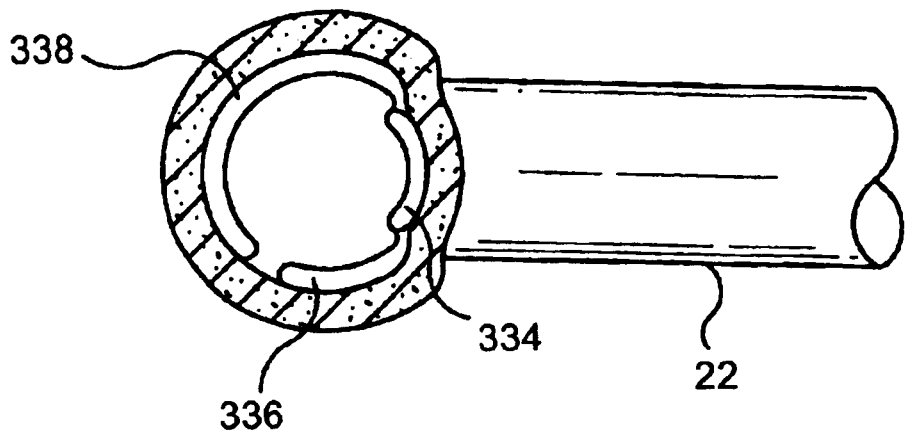
Figure 40D:
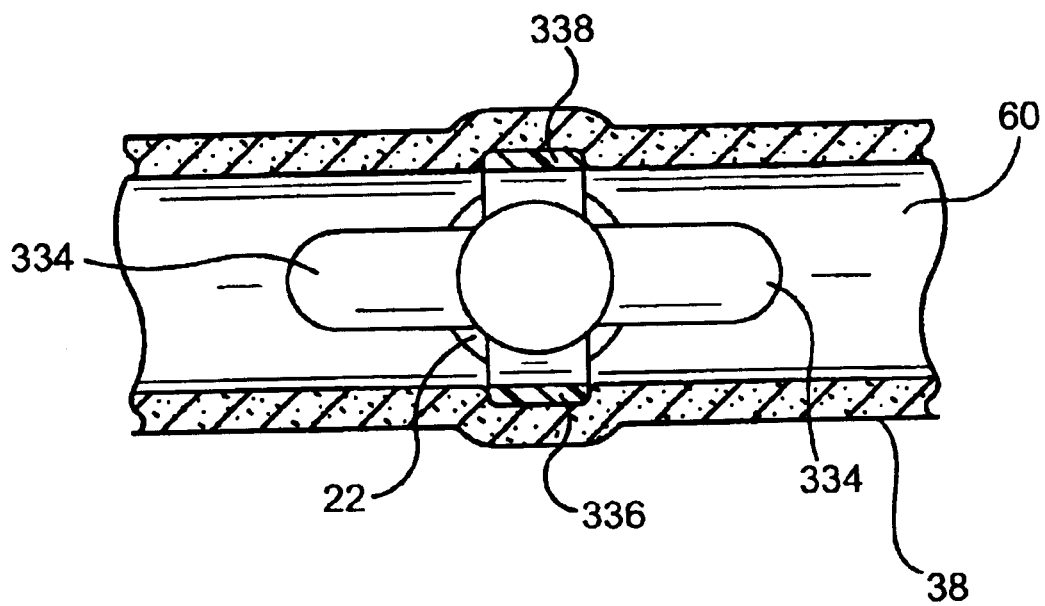
Figure 40F:
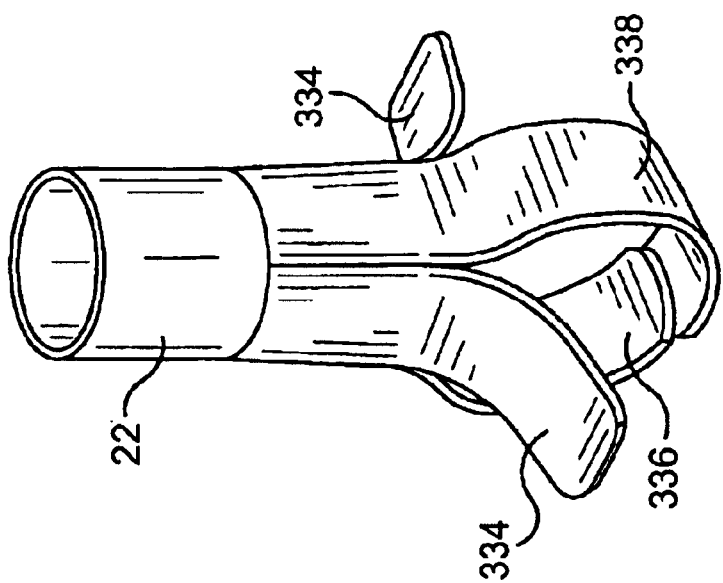
Figure 40E:
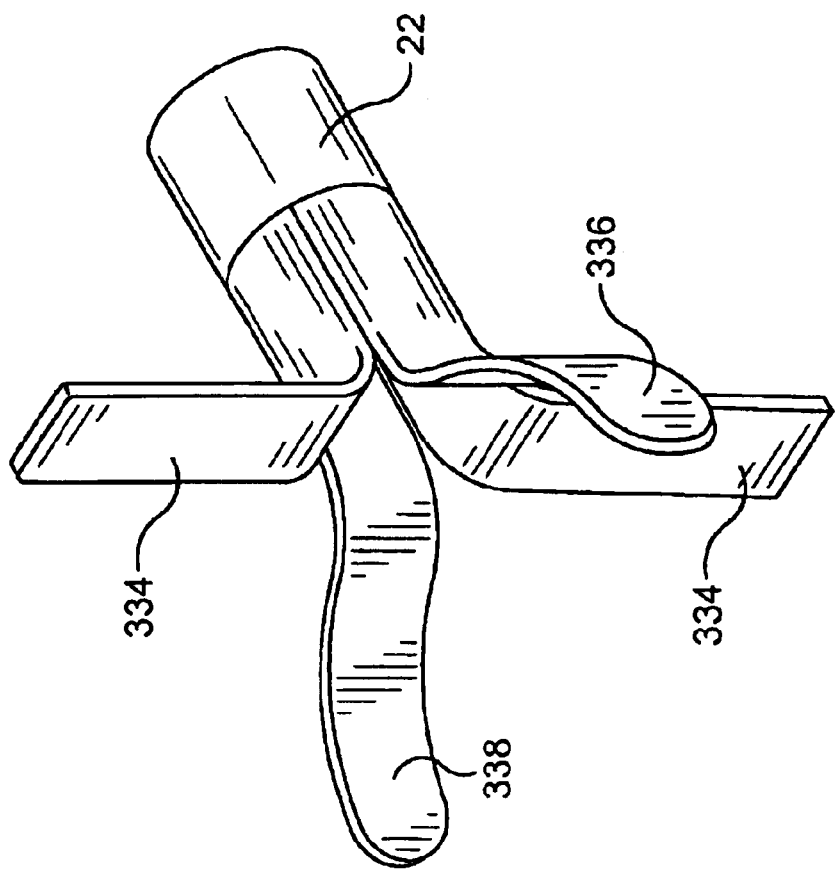
Figure 40G:
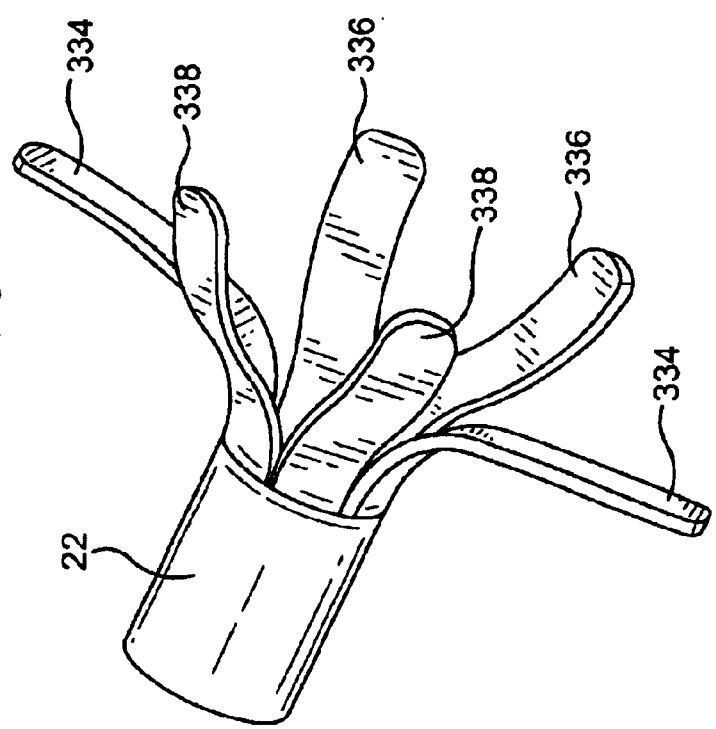

FIGS. 40a to g show an embodiment for producing end-side anastomoses mostly targeting medium to small diameter vessels (e.g. peripheral vessels and coronary vessels). For circumstances where the bypass graft is everted around the fitting and secured using a retaining ring, the petals are incorporated into the retaining ring design, as shown in FIGS. 15e and f; otherwise, the petals are incorporated into the fitting design. The petals shown in this embodiment are incorporated into the fitting design. The fitting incorporates petals that secure a bypass graft to medium and small diameter vessels. As shown in FIGS. 40a and b, four petals are collapsed into a low profile for insertion through a sheath 176 during deployment into the vessel. Once positioned, the sheath 40 is retracted or the fitting is advanced beyond the sheath enabling the petals to expand toward their resting shape. This fitting includes two petals 334 designed to extend axially along the vessel and preformed to contact the host vessel wall. The fitting also includes two other petals 336 and 338 designed to extend radially around a portion of the vessel. The petals provide a structure to prevent the fitting from pulling out of the vessel, restrict rotation of the fitting relative to the bypass graft, ensure the host vessel does not collapse or constrict at the anastomosis site, and provide a support to compress the vessel wall between fitting components. Petals 336 and 338 are configured to return to a closed configuration in their resting state, as shown in FIG. 40f. Alternatively, these petals are configured to expand beyond the closed configuration in their resting state, as shown in FIG. 40e. The latter configuration helps the fitting petals exert radial force on the host vessel to better support the fitting within the host vessel and keep the host vessel open at the bond interface. These end-side fittings may alternatively include more than 4 petals. FIG. 40g shows an end-side fitting having two axially oriented petals 334 and four radially oriented petals 336 and 338. The petals 336 and 338 on this end-side fitting embodiment are configured to expand beyond the closed configuration in their resting state; alternatively, the petals may be configured to return to a closed configuration in their resting state. All fittings that produce end-side anastomoses may be configured to produce an angle between the bypass graft 22 and the interior of the host vessel, preferably from 30 to 90 degrees.

Figure 41A:
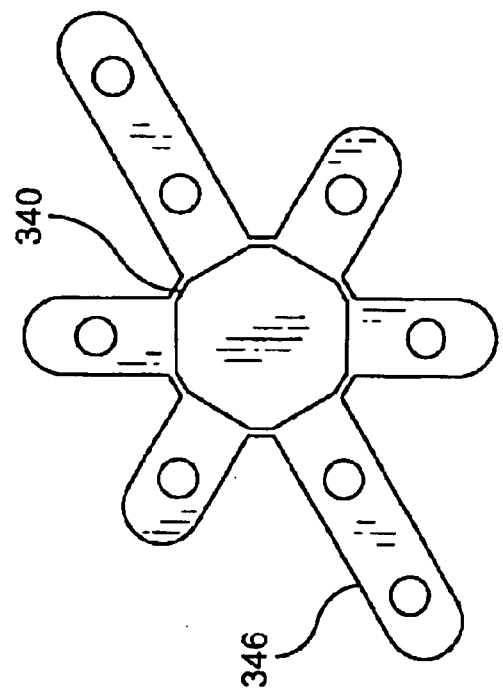
Figure 41B:
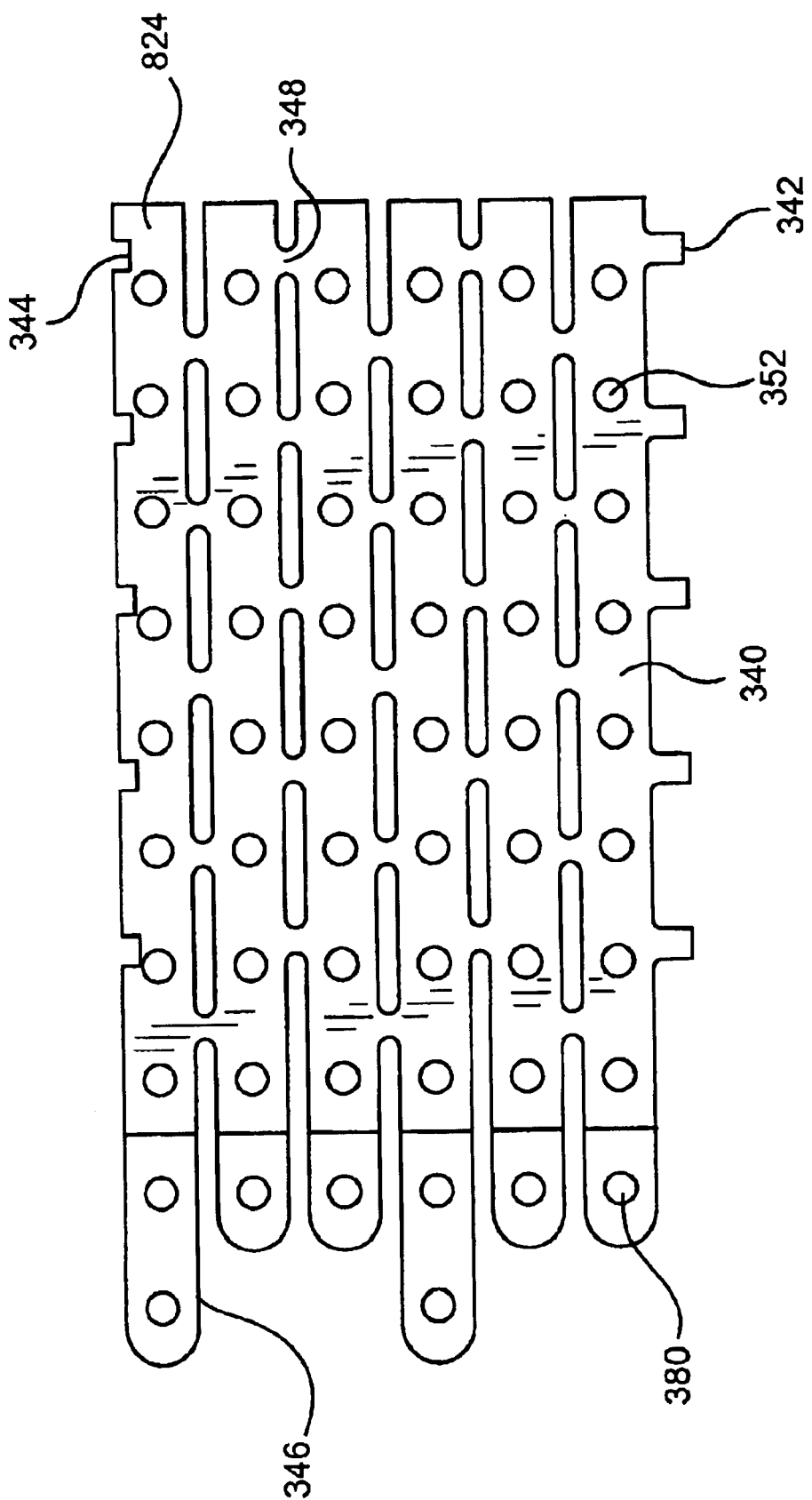
Figure 41C:
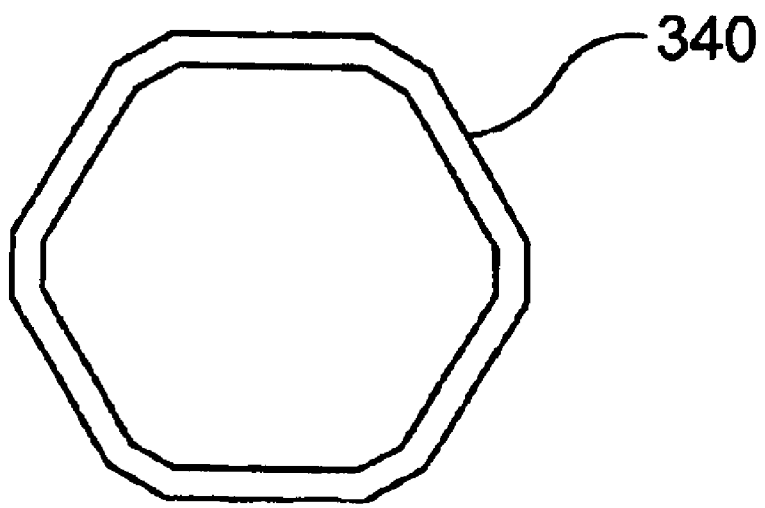
Figure 41D:
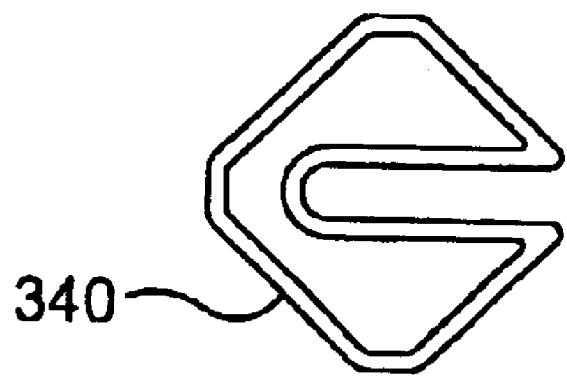
Figure 41H:
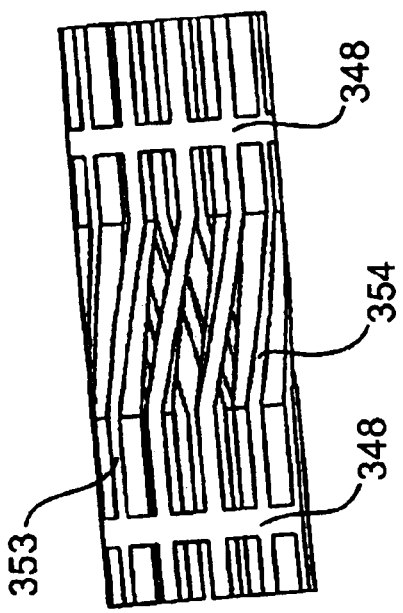

FIGS. 41a to f show an adaptation of the end-side fitting that may be folded to insert through a sheath with a smaller diameter than the fitting. As shown in FIG. 41b, this foldable fitting 340 may be fabricated from a sheet of metal material that has been chemically etched, EDM, or laser drilled into the pattern shown; other manufacturing processes may alternatively be used. The opposite sides 342 and 344 of the fitting match so they may be bonded together (e.g. spot welded, soldered, adhesively bonded, or other process) to form the expanded cross-section shown in FIG. 41c. Alternatively, the fitting may be fabricated from a tubular metal material using chemical etching, EDM, laser drilling, or other manufacturing process to form the desired pattern.

As shown in FIG. 41a, petals 346 are preshaped to expand radially outward once they have been deployed outside the introducing sheath. In this configuration the vessel wall can be compressed between the petals of the fitting and a compression ring as described above. The fitting is also designed to fold into a reduced diameter (shown in FIG. 41d) during deployment and expand toward its resting shape once positioned past the distal end of the sheath. The fitting includes links 348 that are fabricated by reducing the thickness or width of the fitting material and act as hinges for the fitting to fold into a low profile. The foldable fitting embodiment shown in FIGS. 41a to f is designed with 6 sides connected with links 348 so two adjacent sides are able to fold inward thereby reducing the diameter for insertion through the delivery system. The foldable fitting may further be configured so two more adjacent sides that are opposite to the initially folded sides are able to fold inward and further decrease the profile for insertion through the delivery system. To provide a fitting with six sides including two opposing pairs of adjacent sides that fold inward, the pairs of foldable sides are fabricated with a width less than the width of the other sides. This applies to a four-sided fitting as well. In general, the pair of adjacent sides that fold inward have smaller widths than the remaining sides.

Petals 346 are either extensions of the sides or are separate components bonded to the sides through spot welding, thermal bonding, or adhesive bonding. The petals are pre-shaped to contact the vessel wall, depending on the application and size of the vessel. When petals are formed by extending and pre-shaping the sides, more than one side can be linked to form a single petal. This feature is especially useful as the number of sides increases to facilitate folding the fitting. The sides may be linked during production of the fitting by chemical etching, EDM, or laser drilling. Alternatively, the sides may be spot welded or soldered together to form links. The links of the petals can also permit folding to facilitate folding of the entire fitting for insertion through a small diameter sheath. All end-side embodiments can be modified to fold into a reduced diameter.

In the embodiment illustrated in FIGS. 41e and f, the foldable fitting incorporates a synthetic graft material 350 extruded, injection molded, or dipped onto fitting 340. These manufacturing processes cause the graft material to fill slots and holes 352 cut in the fitting. This produces a more reliable bond between the synthetic graft material and the expandable, foldable fitting. The covered fitting will still be able to expand and fold as long as synthetic graft materials having a high percent elongation characteristic are chosen. That way, the graft material may stretch along the folds incorporated in the fitting. A biological bypass graft (e.g. harvested vessel) may be sutured to the holes incorporated in the fitting, whether or not the fitting includes a synthetic graft material. The manufacturing processes and materials for fabricating this foldable end-side fitting may also be used to fabricate end-end fittings by excluding the petals from the design. In addition, the foldable fittings may extend throughout the length of the bypass graft and be configured to maintain the potential to fold into a reduced diameter.

Figure 41G:
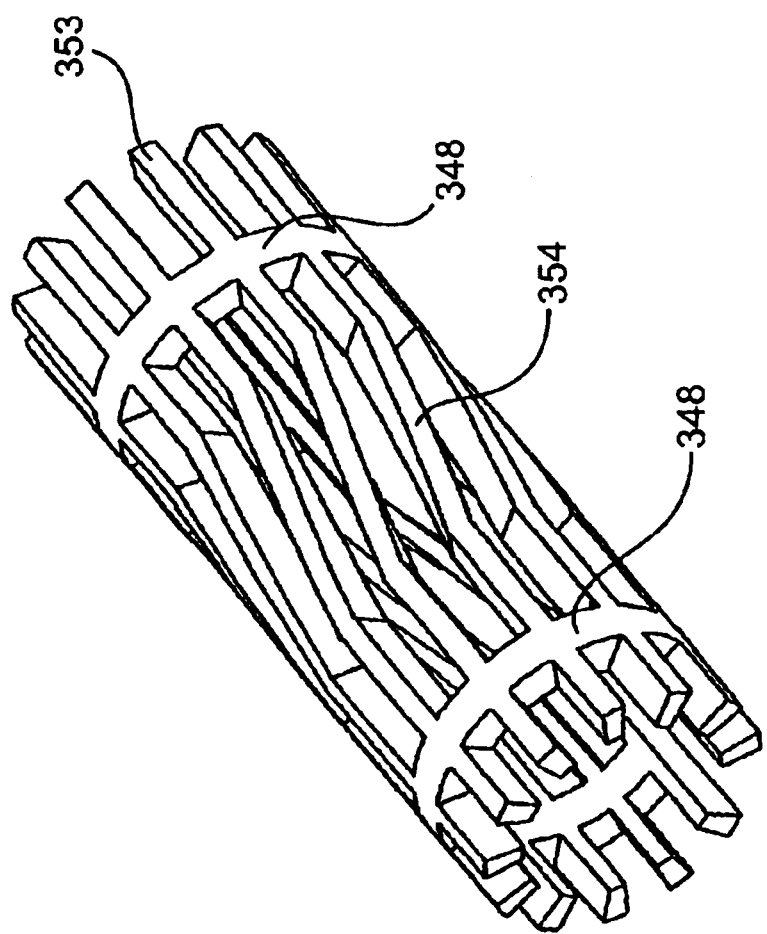

The foldable fitting 353 may have more than 6 sides and be configured so multiple adjacent sides fold inward to further reduce the profile for introduction, as shown in FIGS. 41g and h. Foldable fitting 353 includes twelve sides interconnected with links. When the fitting includes more than six sides, multiple pairs of adjacent sides can be folded inward without varying the widths of the sides. This further reduces the folded diameter of the fitting because pairs of adjacent sides folding inward do not interfere with the folding of opposite pairs of adjacent sides. The foldable fitting shown in FIGS. 41g and h also present another adaptation to the foldable fitting, axial flexibility. By breaking the sides into more than one longitudinal section and connecting the sections with slanted links 354, the fitting may still be folded along the links 822 and 826 but increases flexibility along the fitting axis. This feature is especially useful when the fitting structure extends the length of the bypass graft where axial flexibility is important to the deployment of the bypass graft and conformance to the vasculature.

Figure 42:
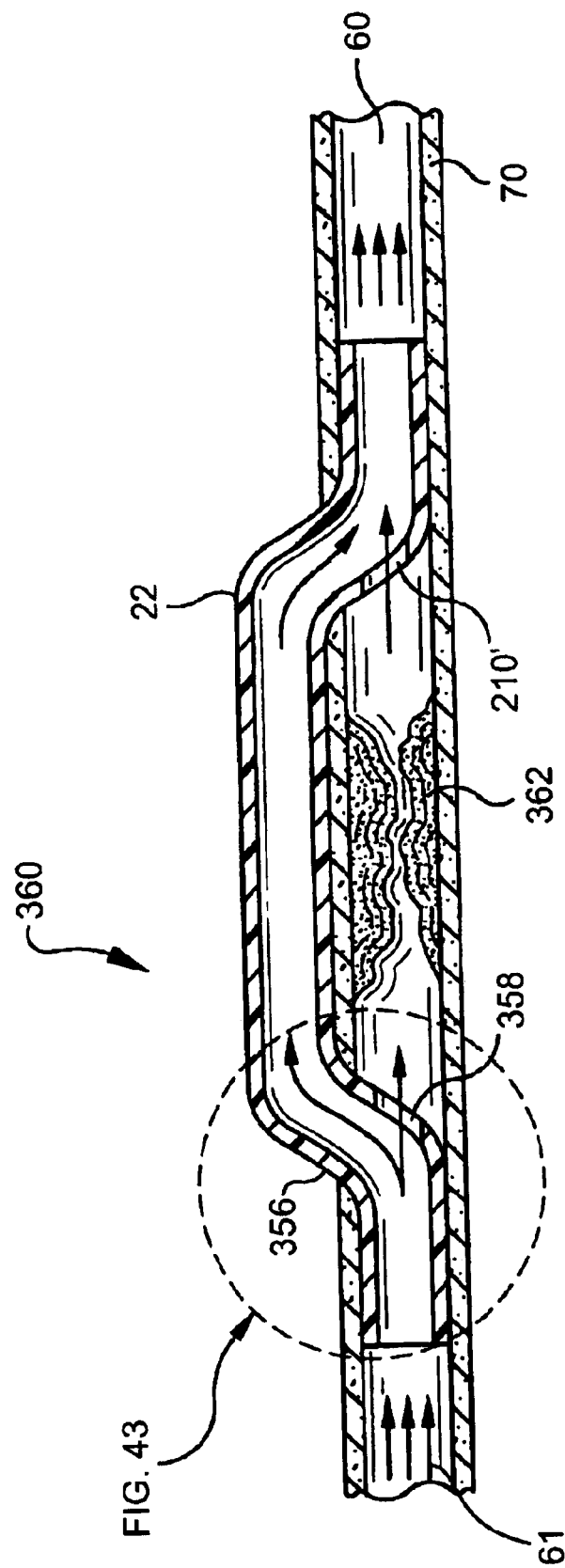
FIG. 42 shows a bypass graft and fitting combination attached to a host vessel and designed to preserve flow proximal to the anastomosis site.
Figure 43A:
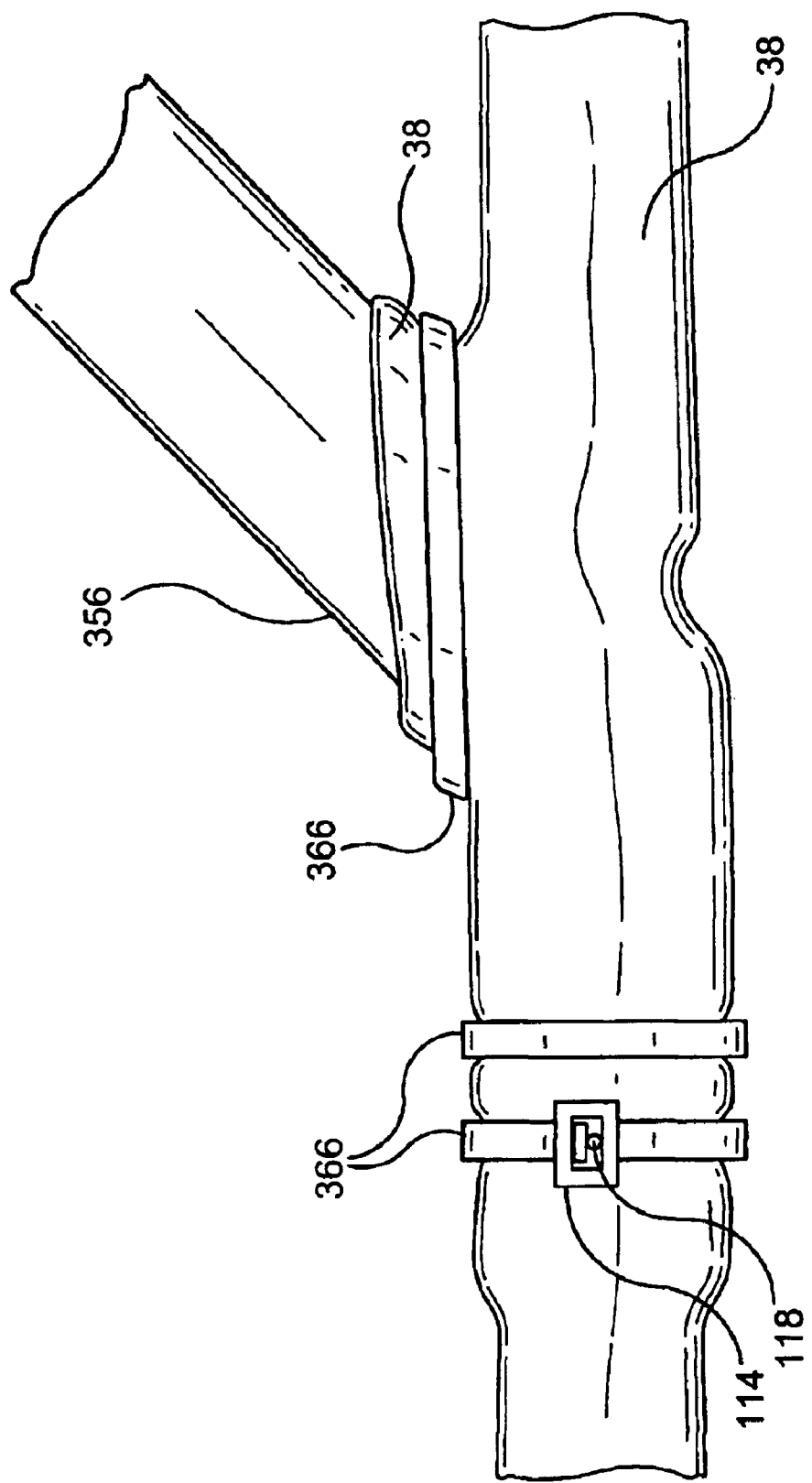
FIGS. 43a and b are close-up views of the bypass graft and fitting combination shown in FIG. 42.
Figure 43B:
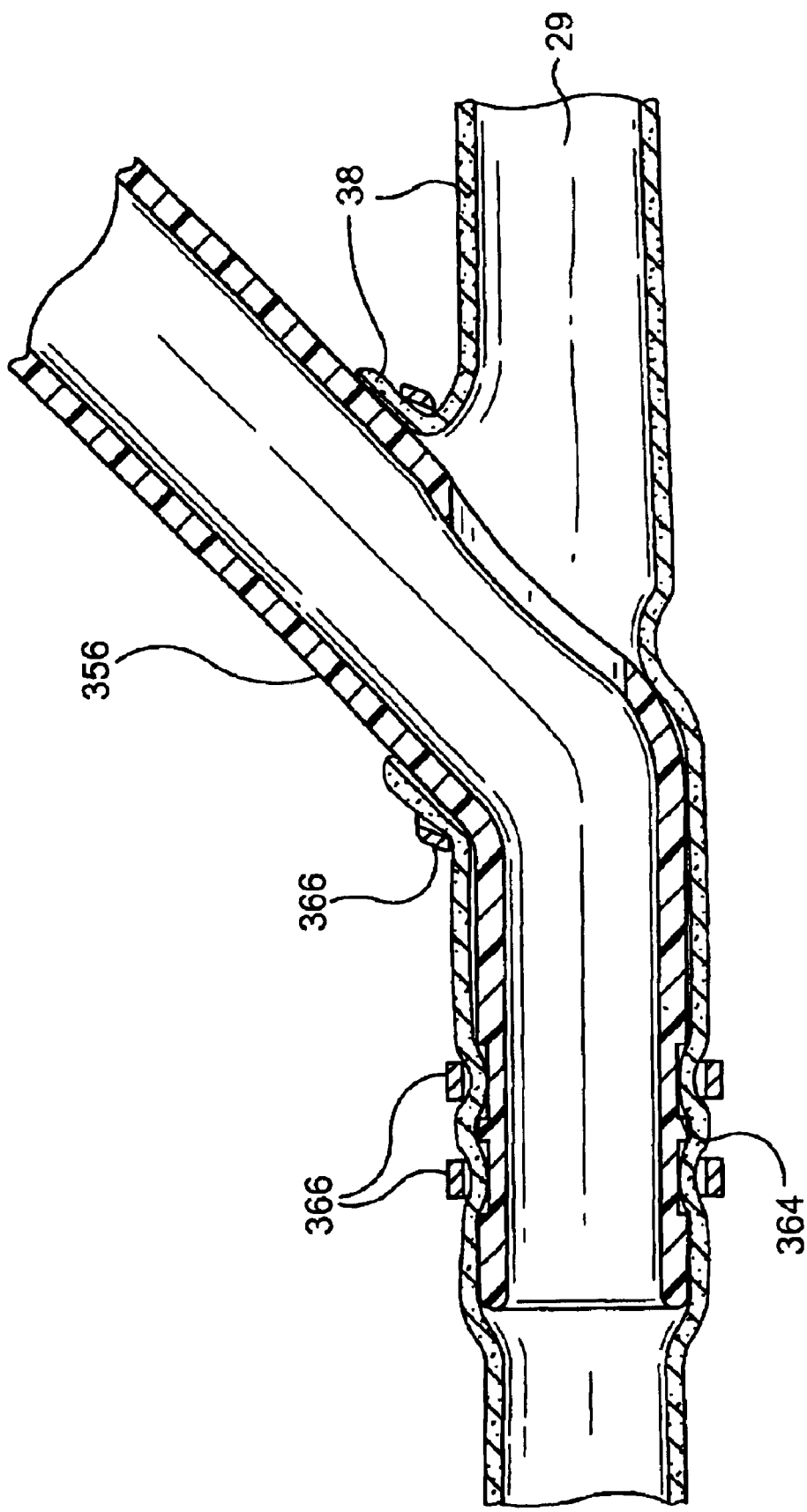
FIGS. 43c to g show alternative bypass graft and fittings designed to maintain retrograde blood flow.
Figure 43C:
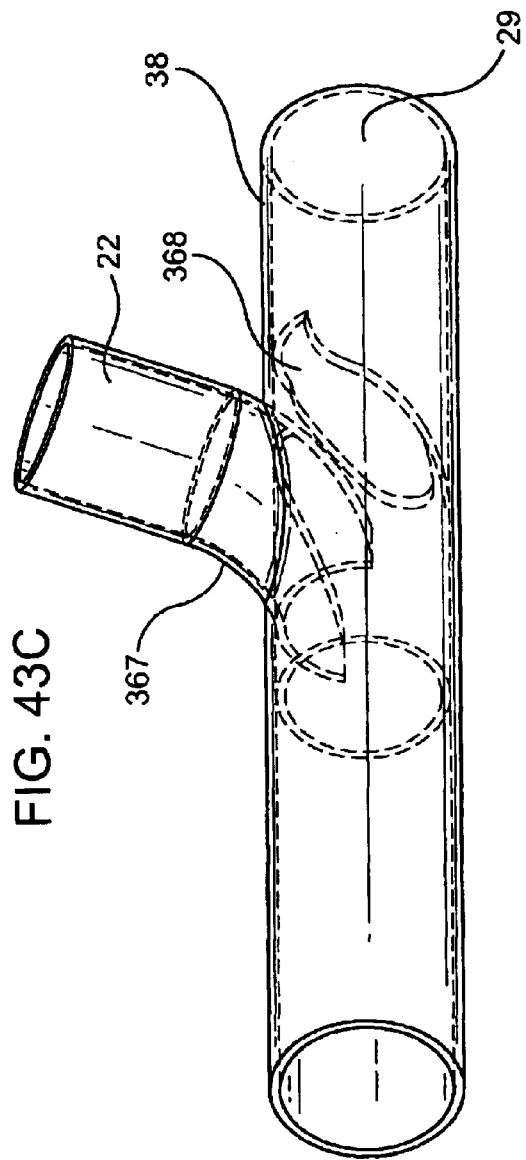
Figure 43D:
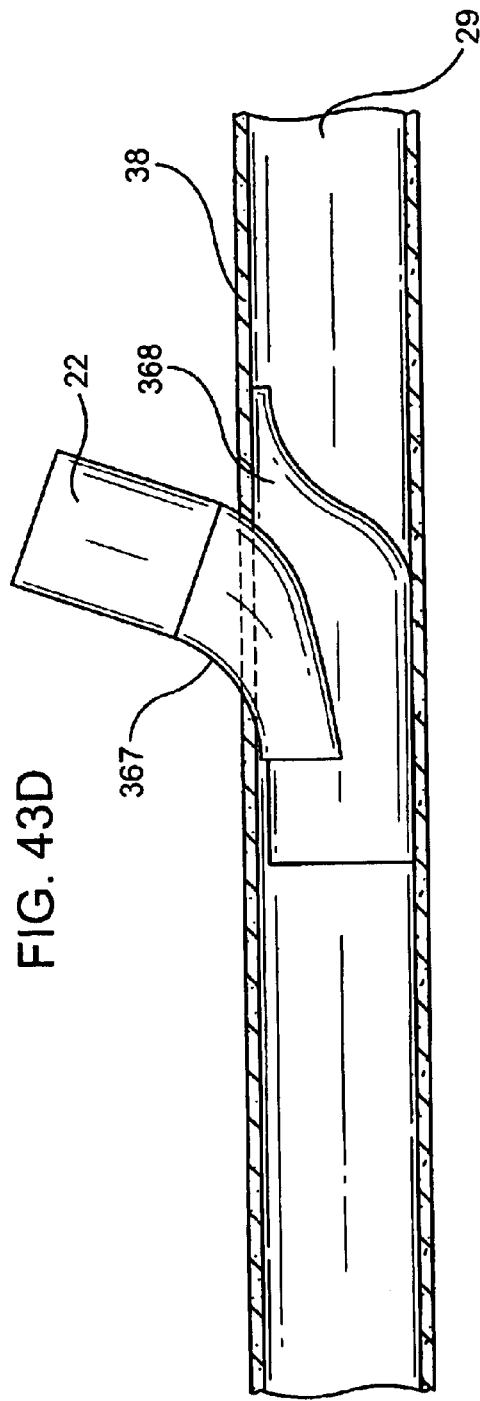
Figure 43E:
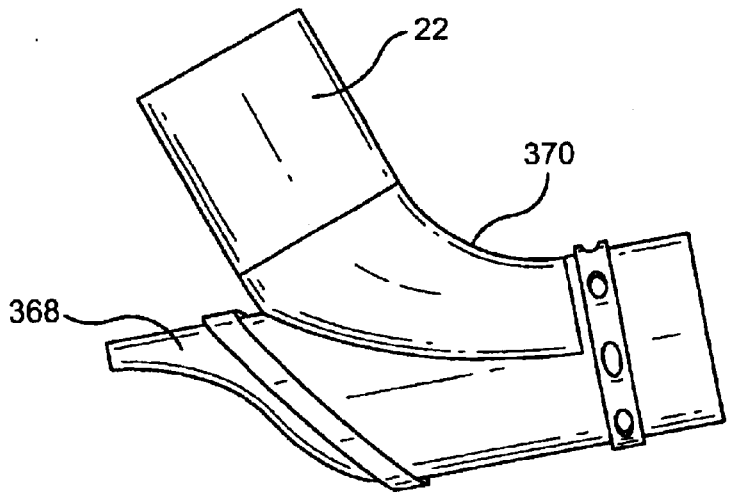

FIGS. 42, 43a, and 43b show an end-end fitting that permits retrograde blood flow through the anastomosis site. The fitting 356 has holes 358 through the angled sections of the fittings to preserve fluid flow through the vessel distal and/or proximal, depending on the location of the fitting within the host vessel. For example, FIG. 42 shows a bypass graft and fitting system 360 which, after deployed within and attached to the vessel, maintains blood flow through the stenosis as well as establishes a passage around the lesion 362. In addition, end-end fitting 356 maintains blood flow to branching vessels proximal to the anastomosis site.

As shown in FIGS. 43a and b, fittings 356 are attached to the vessel at two locations. The fitting is placed within the vessel and contacts the interior surface of the vessel along a substantial length. FIG. 43b shows that the fitting may incorporate barbs 364 to prevent axial dislodgment of the fitting from the host vessel. These barbs may also provide a support to secure a retaining ring or suture to mechanically secure the fitting to the host vessel. The second attachment location is at the insertion site through the vessel wall. A compression ring or retaining ring 366 may be used to compress the vessel wall around the fitting and prevent fluid from leaking at the insertion site. This fitting is particularly useful for medium diameter vessels (>3 mm) where synthetic bypass grafts are used to supplement the blood flow through the vessel or shunt the blood flow to other vessels or organs.

FIGS. 43c to g show additional end-end fitting embodiments that permit retrograde blood flow. A fitting 367 shown in FIGS. 43c and d incorporate a modification to the embodiment shown in FIGS. 43a and b in that a short proximal extension 368 contacts the vessel wall along the insertion site into the host vessel. This provides a structure to attach a compression ring and produce a fluid tight bond at the insertion site. Of course, a locking mechanism is incorporated in the fitting design to enable securing a compression ring to the fitting.

Figure 43F:
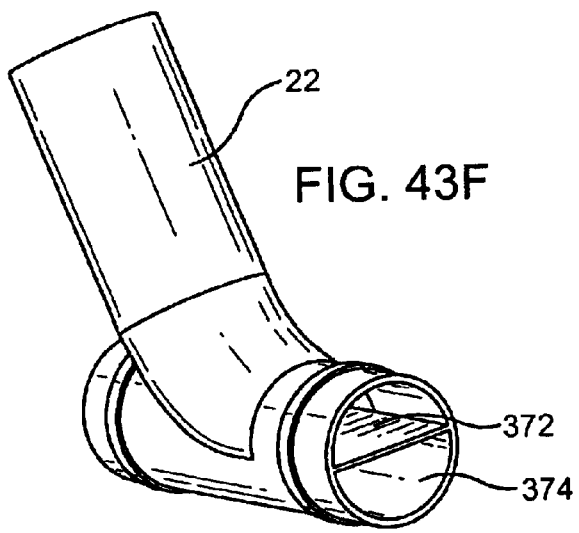
Figure 43G:
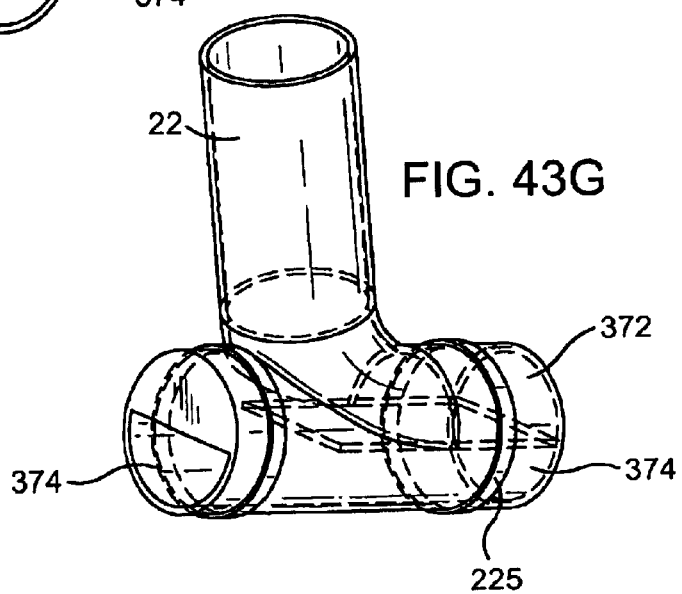

FIGS. 43f and g show another end-end fitting 370 that permits retrograde perfusion. This fitting incorporates distal and proximal extensions used to secure the fitting to the host vessel using retaining rings; alternatively the distal and proximal extensions provide support to secure the fitting to the host vessel wall at the insertion site using a compression ring. This fitting also includes two separate lumens; one lumen 372 connects blood flow from the bypass graft 22 to the host vessel, and the second lumen 374 connects blood flow between regions of the host vessel proximal to the anastomosis site and distal to the anastomosis site.

Other fittings used to produce end-end anastomoses do not permit retrograde blood flow. FIG. 18 shows two end-end fittings that are attached in-line along a vessel 29. The fittings are designed to support the bypass graft at the vessel wall insertion site and prevent the host vessel from constricting the diameter of the bypass graft 22. As previously described, bypass graft 22 may be advanced through the graft fitting and everted around the distal end of the fitting. A retaining ring 34 is used to secure the bypass graft 22 to the fitting and is positioned within the notched region 56 of the fitting. When the bypass graft 22 does not need to be everted, such as when using synthetic bypass grafts, the bypass graft may be attached to the exterior of the fitting as shown in FIG. 18, or the fitting may be laminated between layers of synthetic bypass graft material. In addition to securing the bypass graft, the fittings help maintain the patency of the bypass graft by preventing the bypass graft from collapsing at the insertion site. These end-end fittings are particularly useful when performing in-line anastomoses along a vessel and around a vascular abnormality. They are also useful to treat total occlusions when retrograde blood flow is not beneficial.

Additional Graft Fitting Features

Figure 44:
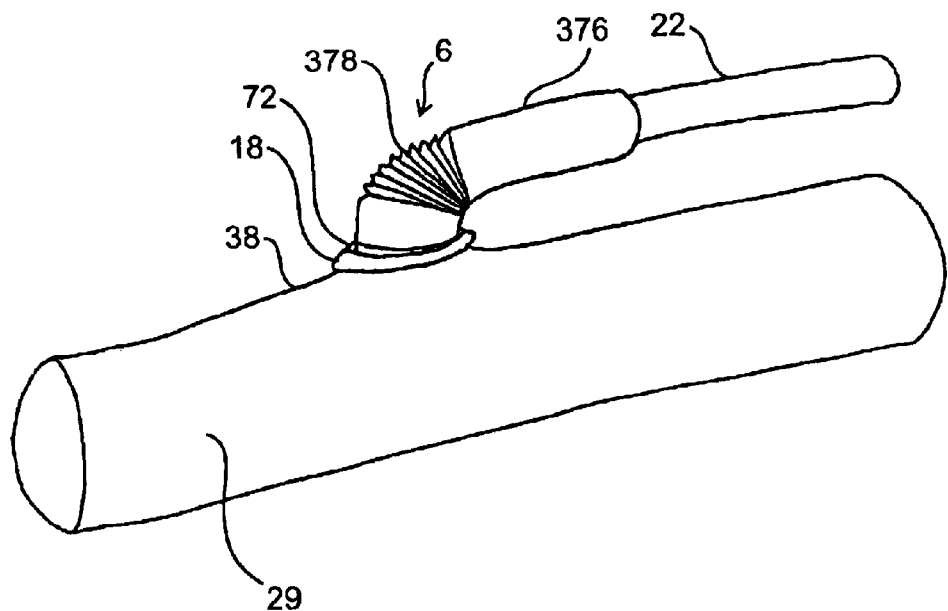
FIG. 44 is an elevated view of a bypass graft and fitting combination attached to a host vessel wall and incorporating a strain relief around the fitting.

Additional features may be included in any of the fitting configurations described above. FIG. 44 shows a fitting 376 similar to the disclosed configurations having a strain relief 378 just proximal to the anastomosis. This strain relief provides additional support to the bypass graft 22 while preventing kinking, especially during the manipulations involved in inserting and attaching the opposite end of the bypass graft. In addition, the strain relief reduces the profile of the fitting, making it less traumatic during use.

Figure 45A:
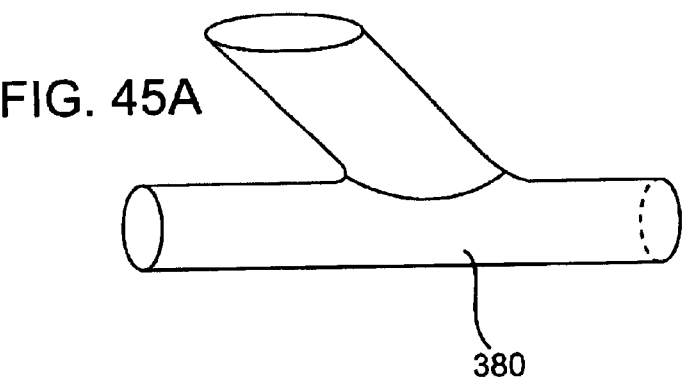
FIGS. 45a to c show "Y" fittings used to attach multiple bypass grafts from a single vessel attachment point.
Figure 45B:
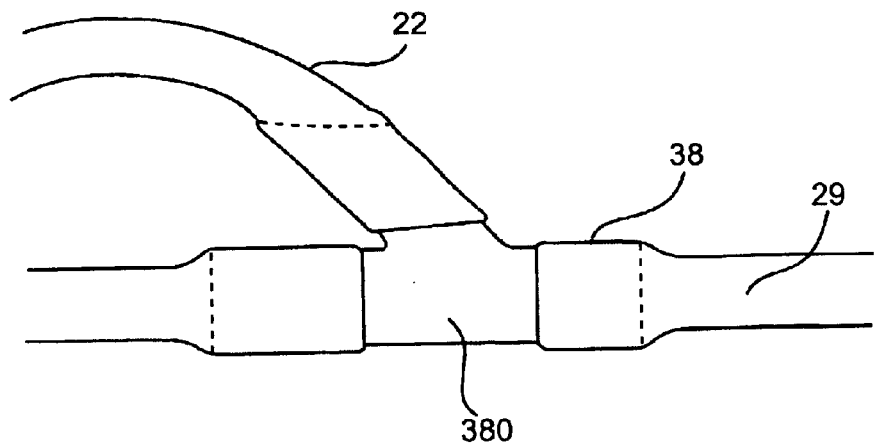
Figure 45C:
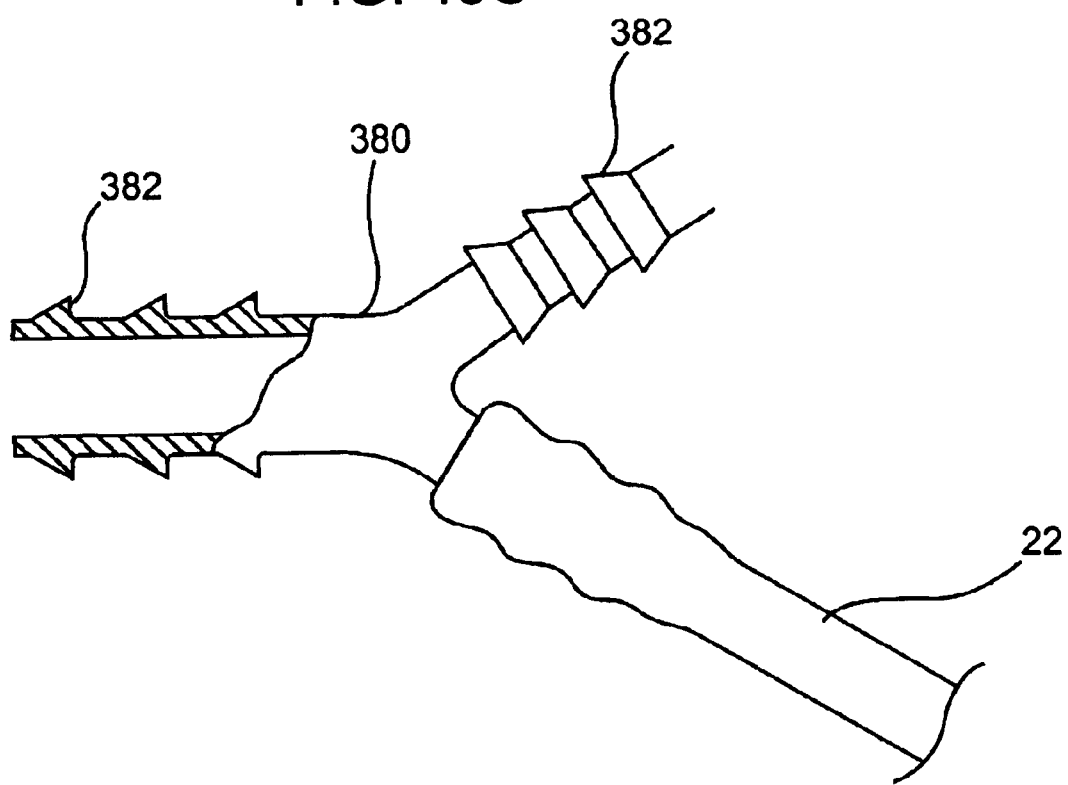

FIGS. 45a to c show a "Y" fitting 380 that used to branch fluid flow distant from the anastomosis site. The bypass graft may be secured to the "Y" fittings 380 using retaining rings previously described. Additionally, the "Y" fitting 380 (shown in FIG. 45c) may include barbs 382 to improve the bond between the bypass graft 22 and "Y" fitting. As with the modular fittings 48 previously described in FIG. 3, the "Y" fittings 380 may have a larger cross-sectional area at the source end (i.e. the end located at the inflow of fluid from a vessel) than at the branches.

Figure 46A:
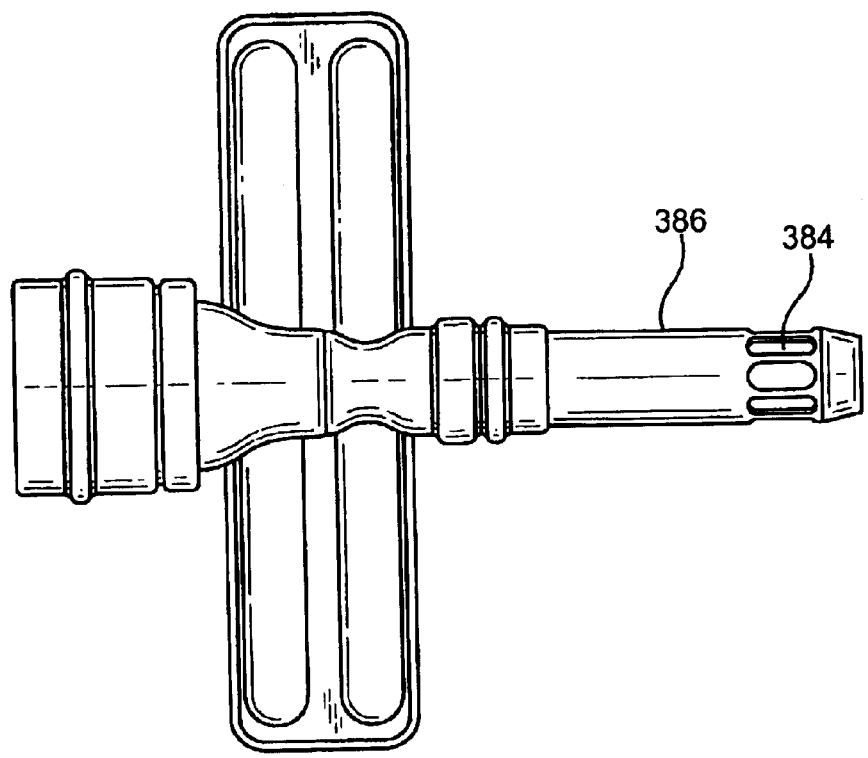
FIGS. 46a and b show tear-away sheath embodiments.
Figure 46B:
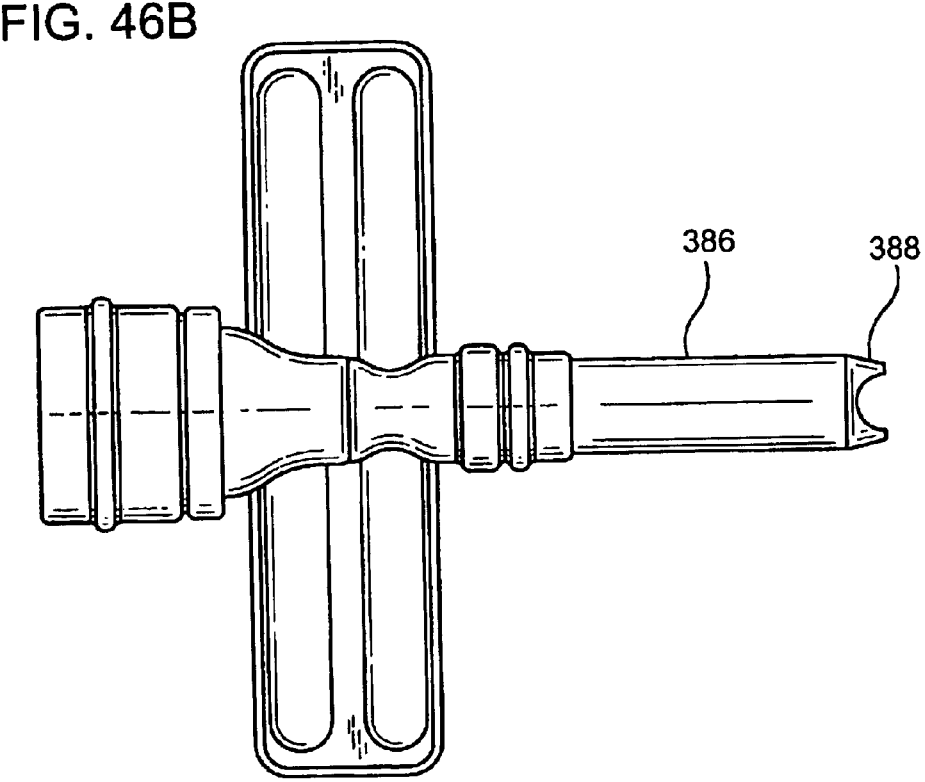

The tear-away sheaths may incorporate features to better maintain blood flow through the host vessel while the tear-away sheath is positioned inside the lumen of the host vessel. FIG. 46a shows cut-out areas 384 oriented along the tear-away sheath 386 and distributed radially around the sheath that permit blood to flow through the cut-out areas in the sheath and past the distal lumen of the sheath. Alternative distributions and geometries for the cut-out areas may be chosen based on the application and insertion requirements for the bypass graft. FIG. 46b shows a tear-away sheath incorporating an anchoring extension 388 at the distal end of the sheath. The extension is designed to maintain access between the tear-away sheath and the host vessel when the sheath is positioned perpendicular to the host vessel, and temporarily anchor the sheath against the vessel wall.

The length of the sheath should be limited to that required to access the interior of the host vessel while ensuring short bypass grafts may be inserted past the distal end of the sheath, especially when the bypass graft has been secured at the opposite end. To make the sheath suitable for less invasive access, a long side arm extension to the sheath may be incorporated to support the sheath during manipulations. The side arm should define two separable sections that permit splitting and remotely tear the sheath into two sections to remove from around the bypass graft.

Figure 47:
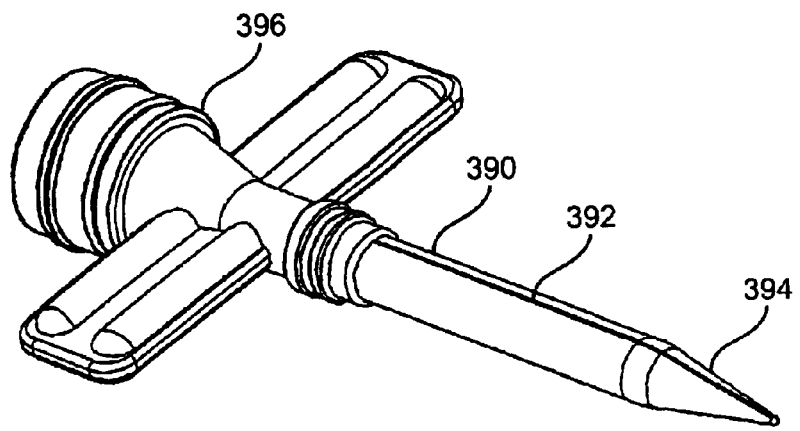
FIG. 47 shows a dilating sheath embodiment.
Figure 48A:
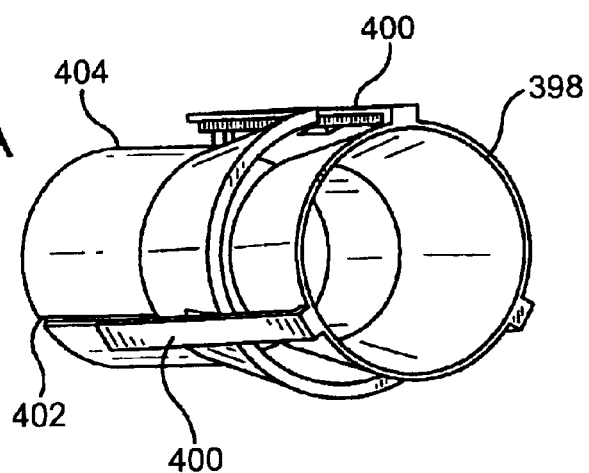
FIGS. 48a to d show an axial snap end-end fitting designed to rapidly attach a bypass graft to the fitting.
Figure 48B:
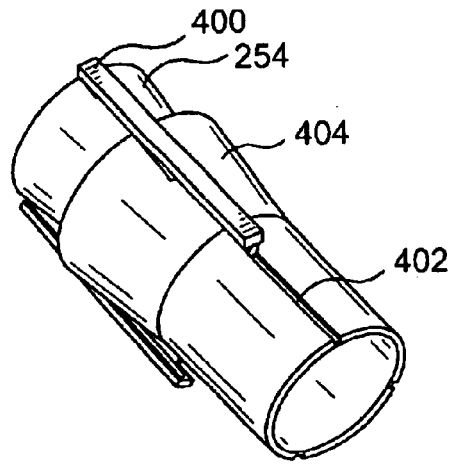
Figure 48C:
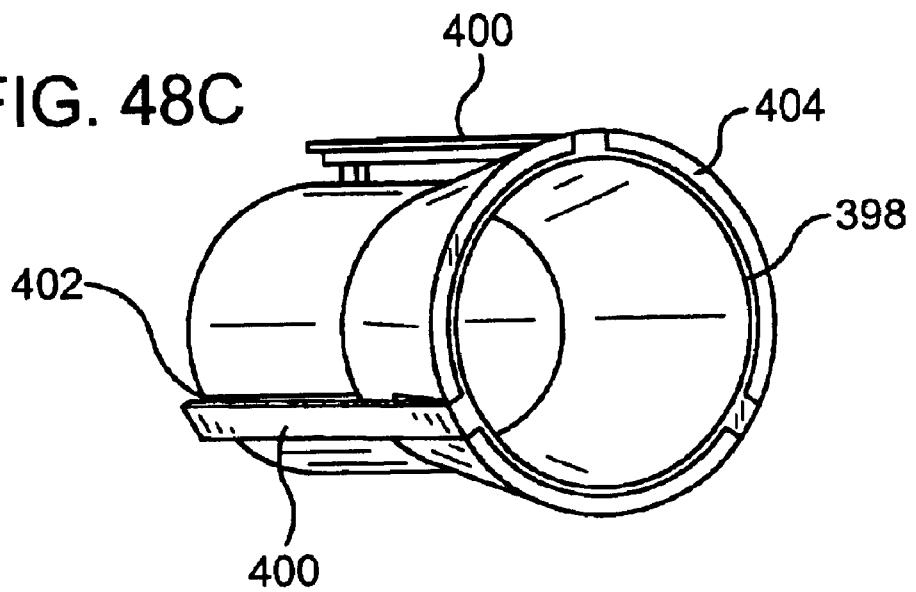
Figure 48D:
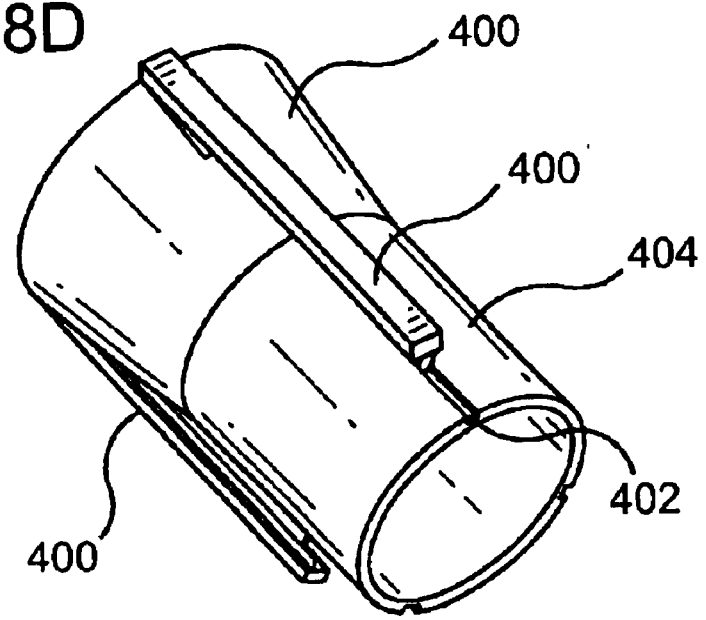
Figure 49A:
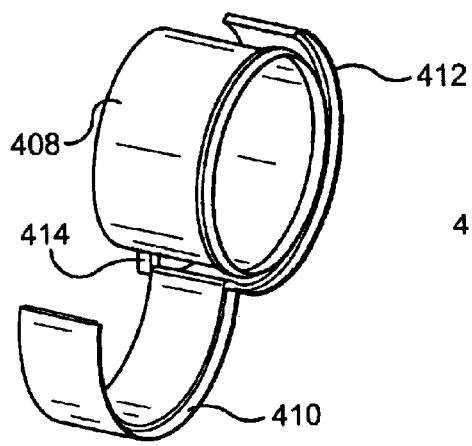
FIGS. 49a to d show a radial snap end-end fitting designed to rapidly attach a bypass graft to the fitting.
Figure 49B:
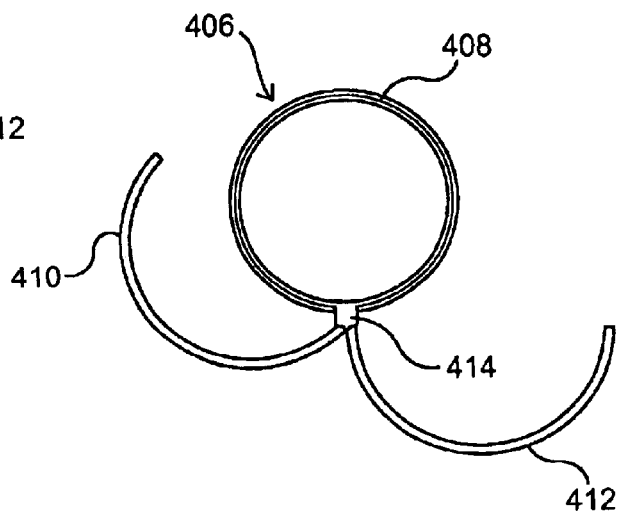
Figure 49C:
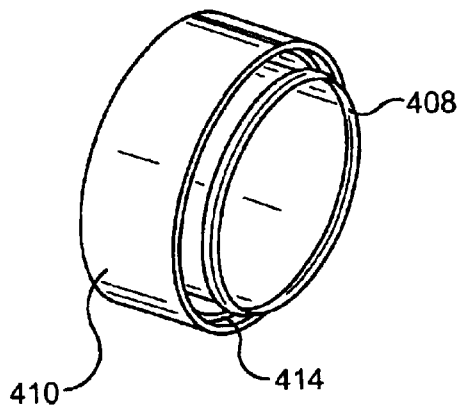
Figure 49D:
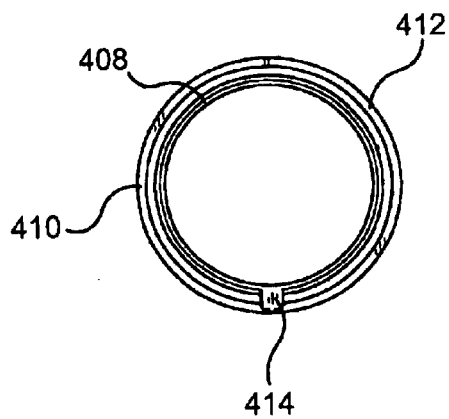

FIG. 47 shows an adaptation of a delivery system that combines the tear-away sheath and the dilating member into one component. A dilating sheath 390 contains at least one groove, slit, or series of perforations 392 that enables splitting the dilating sheath for removal from around the bypass graft. The dilating sheath also contains a tapered distal end 394 that is designed to follow a needle or guidewire through a puncture in the vessel wall and expand the puncture to facilitate inserting the main section of the dilating sheath into the vessel. The dilating sheath has a central lumen (not shown) adapted to pass the bypass graft and fitting combination. A plunger is used to advance the bypass graft and fitting combination past the tapered end of the dilating sheath and into the host vessel. As discussed for the tear-away sheath, the dilating sheath contains a hub 396 and hemostatic valve that permit splitting along the at least one groove, slit, or series of perforations.

The tapered end of the dilating sheath must prevent collapsing while inserting through and opening the puncture site, and enable expanding so the bypass graft and fitting combination may be advanced into the host vessel lumen. The tapered end may be fabricated by cutting the end of the sheath tubing into three or more sections such that each section tapers distally, forming the sections such that they create a single tapered distal end (the sections may overlap partially), and covering the tapered distal end with a material having a low durometer and a large percent elongation (e.g.

silicone and urethane). The sections are formed such that they exert radial force to prevent collapsing while the dilating sheath is advanced through the puncture site. The covering provides a fluid tight coating around the tapered end that elongates as the sections are spread apart; this enables expanding the diameter of the tapered end while the bypass graft and fitting combination are inserted through the tapered end. An alternative fabrication process eliminates the need for the covering and bonds the overlapping sections with an adhesive. The adhesive holds the position of the tapered end sections and produces a fluid tight interface between the sections but permits separating the sections as the plunger advances the bypass graft and fitting combination through the positioned dilating sheath.

A further adaptation of the tapered end takes advantage of materials having high water adsorption rates. Materials such as cellulose acetate are stiff when dehydrated and extremely flexible when hydrated. The dilating sheath tubing may be fabricated from cellulosics or similar material such that the tapered end is split into three or more sections and formed into a taper. The dilating sheath is allowed to dry where it is relatively stiff and exhibits sufficient column strength to expand the puncture site. Once inside the vessel lumen, the tubing material is exposed to fluid causing it to become more flexible. At this point, the tapered end may be separated into the three or more sections as the bypass graft and fitting combination are advanced into the host vessel.

FIGS. 48a to d show an alternative to the snap fitting described above. The distal and proximal pieces are integrated into one component. This adaptation facilitates manipulation of the bypass graft relative to the fitting since the operator only needs to hold the bypass graft and a single fitting. Otherwise, the operator needs to hold the proximal piece, distal piece, and bypass graft while securing the bypass graft to the fitting. A distal piece 398 contains locking hinges 400 designed to move axially along rails 402 incorporated in the proximal piece 404. The locking hinges move along the rails but are unable to be separated from the proximal piece. To accomplish this, the distal ends of the locking hinges, positioned inside the rail openings, are larger than the width of the rail openings. The distal ends of the locking hinges also have extensions that mate and lock to teeth incorporated in the rails of the snap fitting. During operation, the bypass graft is inserted through the lumen of proximal piece 404 and is advanced over the tapered end of distal piece 398. Then, the proximal piece is moved along the locking hinges of the distal piece compressing the bypass graft between the proximal piece and distal piece. The ends of the locking hinges are secured to the mating teeth of the rails to secure the distal piece relative to the proximal piece. The distal piece as shown is configured for end-end anastomoses. However, it can be modified with features described below to accommodate end-side anastomoses. This snap fitting can be configured to evert the bypass graft, by modifying the fitting such that distal piece 398 can be advanced over proximal piece 404 and compress the bypass graft between the distal piece and proximal piece. The bypass graft is advanced a sufficient amount through the inner surface of the proximal piece and is positioned over the outer surface of the distal piece. When the distal piece is advanced over the proximal piece, the bypass graft is everted over the end of the proximal piece and compressed between the distal and proximal pieces.

FIGS. 49a to d show an alternative snap fitting 406 that has a central piece 408 and a lockable outer pieces 410 and 412. The outer pieces form a single cylindrical component or two distinct sections that are designed to pivot about a hinge

Figure 50A:
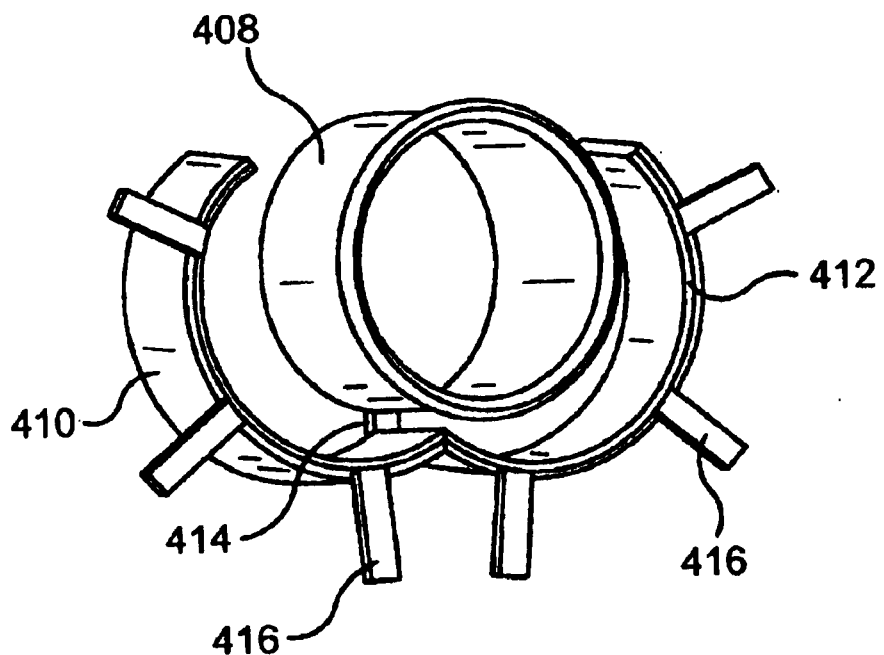
FIGS. 50a and b show a radial snap end-side fitting designed to rapidly attach a bypass graft to the fitting.
Figure 50B:
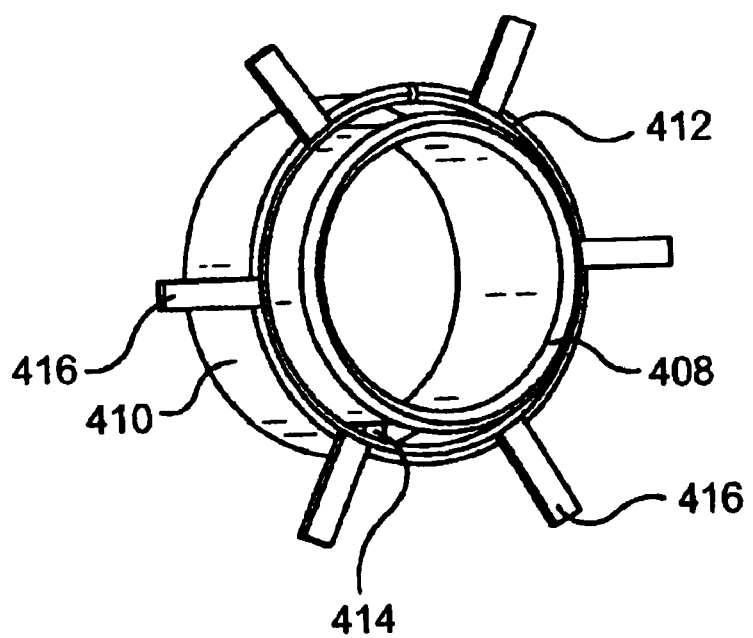

414. The hinge connects the central piece and the outer pieces to facilitate manipulating the snap fitting and the bypass graft. The bypass graft is fed over the central piece from the side of the snap fitting not containing the hinge. The hinge is located on one side of the central piece to facilitate advancing the bypass graft over the central piece without having to cut an incision through the distal end of the bypass graft. After the bypass graft has been positioned over the central piece, the outer piece is closed together compressing the bypass graft between the outer piece and the central piece. A locking mechanism is designed at the contacting ends of the outer pieces and is configured to bond the outer pieces in a closed, cylindrical position to reliably secure the bypass graft to the snap fitting. This may be achieved by incorporating mating teeth on opposite ends of the outer piece tailored to interlock when the ends overlap. As shown in FIGS. 50a and b, this snap fitting may incorporate petals 416 or other suitable modification (not shown but described below) so the fitting may be used to produce end-side anastomoses. Snap fitting 406 can be used to secure the bypass graft in an everted orientation. The bypass graft is inserted through the inner surface of central piece 408 and is everted around the end of the central piece. With the bypass graft everted around the central piece and located on the outer surface of the central piece, outer pieces 410 and 412 are locked, compressing the everted graft against the central piece.

With the embodiments of the invention described above, the bypass graft may be bonded to the fittings prior to securing the fittings to the host vessel. As a result, this step may be performed outside the patient enabling the physician to ensure a strong and leak resistant bond. Another advantage of the fitting embodiments described above are that they may be configured to only or mostly expose the endothelial layer 62 of a biological bypass graft to blood flow. This prevents thrombosis and other interactions observed between foreign materials and blood.

Figure 51A:
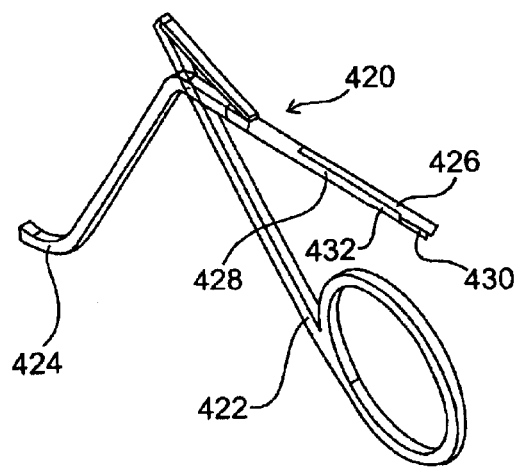
FIGS. 51a to d show a compression tool designed to atraumatically advance a compression ring over an end-side fitting.
Figure 51B:
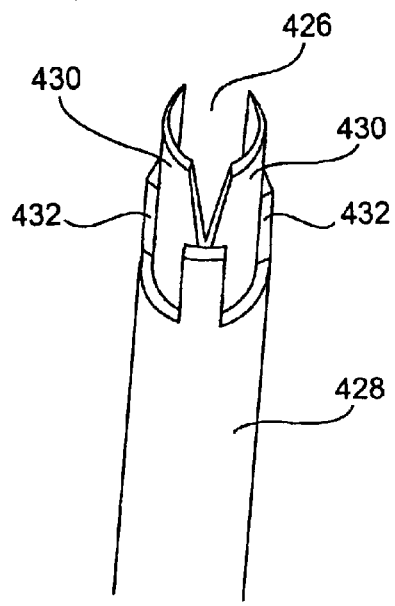
Figure 51C:
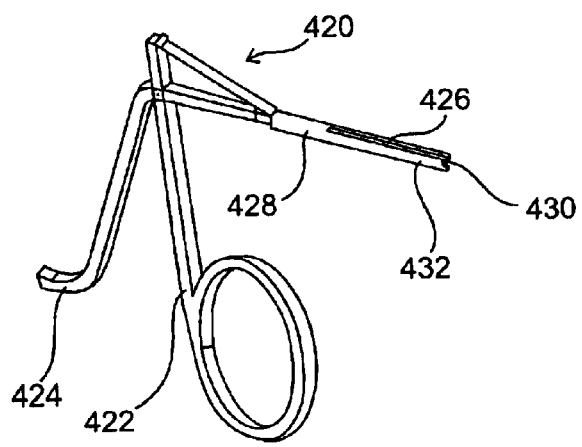
Figure 51D:
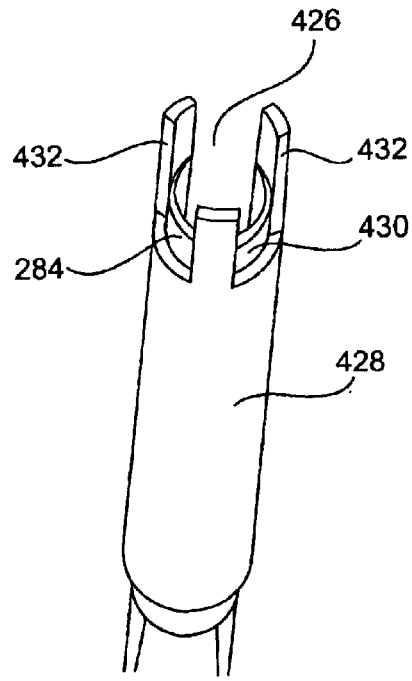

FIGS. 51a to d show a compression tool 420 designed to advance a compression ring over an end-side fitting without pulling the fitting out of the host vessel or damaging the fitting or host vessel during the securing process. FIGS. 51a and b show the compression tool in the relaxed position. The compression tool has a front handle piece 422 and a rear handle piece 424 spread apart in the relaxed position. The handle pieces are squeezed together to advance the compression ring over the end-side fitting as shown in FIGS. 51c and d. The compression tool may be spring loaded to return to the relaxed position when the force causing the handle pieces to squeeze together is removed. The compression tool has a slot 426 through the distal section adapted to fit over the side of the bypass graft and fitting. This eliminates the need to preload the bypass graft through the compression tool prior to the procedure, and facilitates removing the compression tool after securing the bypass graft to the host vessel. As shown in FIG. 51b, the compression tool incorporates a slide 428 adapted to move along grasping legs 430. The grasping legs are anchored to the rear handle piece and the slide is advanced by squeezing the front handle piece towards the rear handle piece. The slide and the grasping legs are configured to define the slot 426 through the distal section of the compression tool. The grasping legs 430 are flared outward as they extend distally to fit around the proximal end of the fitting in the relaxed state and close around the fitting (shown in FIG. 51d) as the slide is advanced over the grasping legs.

Slide extensions 432 are either incorporated in the distal end of the slide design or are bonded to the slide, depending on the manufacturing process and whether the slide extensions are fabricated from the same material as the slide. The slide extensions exert a radial spring force to close the grasping legs around the fitting, and push the compression ring over the end-side fitting. The compression ring is placed over the grasping legs and against the slide extensions prior to advancing the compression ring over the fitting. Then, the compression tool is positioned so the grasping legs extend over the proximal end of the end-side fitting. The front handle piece is squeezed toward the rear handle piece causing the slide 428 to advance over the grasping legs. Simultaneously, the grasping legs close around the fitting temporarily securing the compression tool to the fitting, and the compression ring is advanced over the fitting. This compression tool provides an anchor for grabbing the proximal end of the fitting and advancing the compression ring. This facilitates compressing the vessel wall between the petals of the fitting inside the vessel and the compression ring outside the vessel.

Figure 52A:
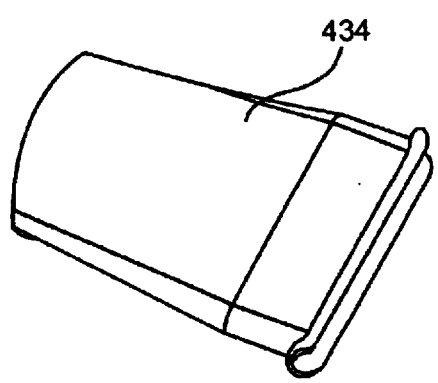
FIGS. 52a to d show another embodiment of an end-side fitting.
Figure 52B:
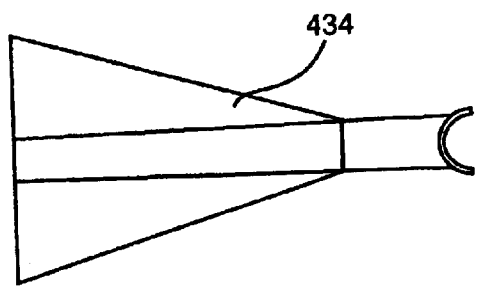
Figure 52C:
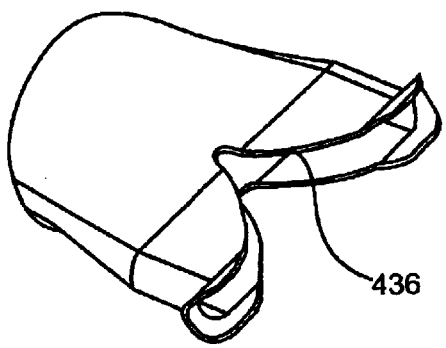
Figure 52D:
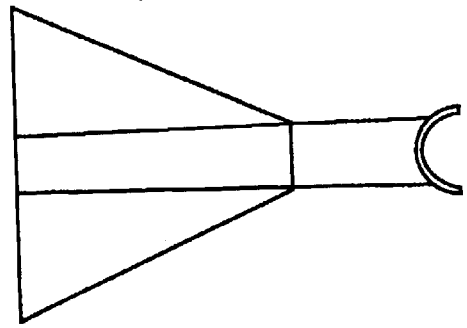

End-side fittings may be oval in cross-section as shown at 434 in FIGS. 52a and b. This facilitates an end-side anastomosis between a large diameter bypass graft and a small diameter host vessel. When saphenous veins are harvested, they contained valves directing blood flow towards the heart. The diameter of the saphenous vein increases in the direction along the blood flow path. Instead of removing the valves and damaging the vein, the saphenous vein can be oriented such that the valves direct blood flow from the aorta to the coronary arteries during a coronary artery bypass grafting procedure. Thus, the larger diameter section of the saphenous vein is located at the coronary artery and the smaller diameter section of the saphenous vein is located at the aorta. The fittings can account for this by making the geometry of the everted saphenous vein oval to facilitate inserting an elongated fitting through the delivery sheath. The sheath cross-section also can be oval. Alternatively, the end-side fitting may include a central slot 436 as shown in FIGS. 52c and d. The central slot permits compressing the fitting into a low profile for insertion through a smaller diameter sheath. When the fitting is advanced beyond the sheath, it expands toward its oval configuration.

Figure 53A:
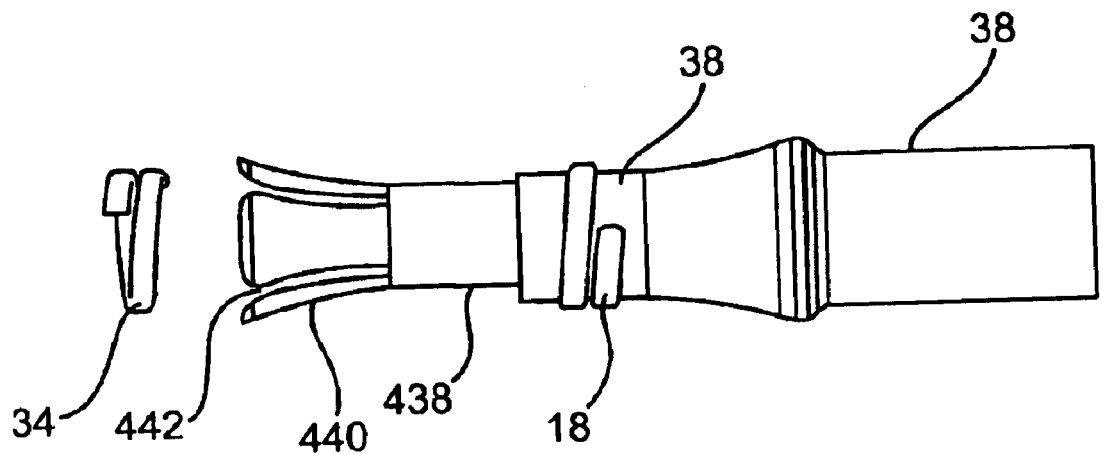
FIGS. 53a and b show another embodiment of an end-end fitting.
Figure 53B:
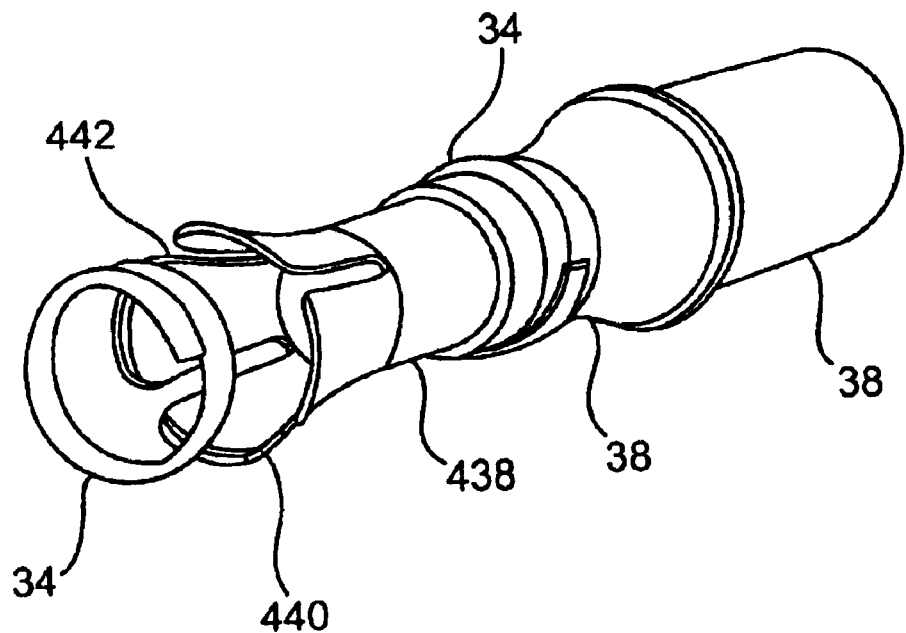

FIGS. 53a and b show a temporary graft 438 that can maintain blood flow between two vessel ends for a short time before a permanent end-end anastomosis. The temporary graft has two end-end fittings 440 connected with a short length of graft material. The graft material may be a polymer, silicone, or metal. Graft 440 is fabricated from a hypotube (stainless steel or nickel titanium) in which longitudinal slots 442 in the ends form the opposite end-end fittings. The ends of the fittings are flared outward and treated to impose a memory elastic characteristic. Thus, the fittings are compressible into a low profile for insertion into a vessel, and return towards an expanded resting configuration when an external compressing force is removed. A slidable or splittable tubing (not shown) can be used to provide the compressive force. In addition, the hockey stick device described above can be use to insert the end-end fittings into the host vessel ends. After graft 438 is positioned, retaining rings 34 are advanced over the end-end fittings to compress the vessel wall against the fittings and thus temporarily secure the graft to the host vessel. The retaining rings are removable from around the fittings when the physician is ready to perform the permanent anastomosis. Then, previously described fittings and securing modalities are put to use. Temporary graft 438 rapidly provides blood flow between severed vessels or vessel ends during transplantations, when it is important to minimize ischemia time.

The fittings can be fabricated with holes, notches, and slots cut in the fitting, using laser drilling, EDM, milling, or other manufacturing processes. The fittings also can be covered with a porous material, such as collagen, fibrinogen, gelatin, and urethane, to further define a structure incorporating holes, notches, and slots. The holes, notches and slots encourage neointimal cell growth to decrease biological interactions of the portion of the fitting exposed to blood.

The fittings in accordance with this invention may be used in any combination to secure bypass grafts at discrete vessel locations. In addition, synthetic and biological bypass grafts may also be used in any combination with the graft fittings to produce passages around vascular abnormalities during a particular procedure.

What is claimed is:

1. An anastomotic connector comprising:
   a fitting having a tubular portion and a flange extending substantially transverse from a distal end thereof, the flange having a thickness and a slot extending non-radially with respect to the tubular portion through the entirety of the thickness and defining an acute tissue dilating tip configured for insertion into an opening within a vessel wall, wherein rotation of the fitting facilitates entry of the flange into the opening; and at least one tab extending from the tubular portion.

2. The connector of claim 1 additionally comprising a ring adapted to fit over the tubular portion and to hold tissue positioned between the ring and the flange.

3. The connector of claim 2 wherein the at least one tab is configured to secure the ring to the tubular portion.

4. The connector of claim 1 wherein at least one section of tubing is disposed along at least a portion of an edge of the flange the tubing defining a lumen.

5. The connector of claim 4 additionally comprising a wire disposed at least partially through the lumen.

6. The connector of claim 1, wherein the flange comprises a first portion and a second portion separated form the first portion by the slot, the first portion of the flange being longitudinally offset from the second portion of the flange.

7. The connector of claim 6, wherein the first portion of the flange longitudinally overlaps the second portion of the flange.

8. An anastomotic graft and fitting system comprising:
   a fitting having a tubular portion with a first radius, a proximal end and a flared distal end, the flared distal end having an edge defining at least one additional radius larger than the first radius, the edge additionally defining at least one aperture extending into the flared distal end, and wherein at least one section of tubing is disposed along at least a portion of the edge, the tubing defining a lumen;
   a wire at least partially disposed through the lumen; and
   a tubular graft affixed to the fitting.

9. A method for creating an anastomosis comprising:
   creating a puncture in a vessel wall;
   disposing a fitting near said puncture, said fitting having a tubular portion with a first radius and a proximal end, the fitting having a flared distal end defining an edge, the edge defining at least one additional radius larger than the first radius, the edge additionally defining at least one aperture extending into the flared distal end;
   rotating the fitting such that the aperture captures the vessel wall as the edge is introduced into the puncture and through the vessel wall; and
   continuing to rotate the fitting until the entire flared distal end passes through the puncture and the vessel wall such that when the rotation is complete the flared distal end is disposed inside a vessel lumen defined by said vessel wall and the tubular portion is disposed outside the vessel lumen.

10. The method of claim 9 additionally comprising the step of securing the fitting to the vessel wall by advancing a ring over the tubular portion such that the ring fixes the vessel wall against the flared distal end.

11. The method of claim 9 wherein the fitting is attached to a graft.

12. The method of claim 9 wherein the distal flared end additionally comprises at least one section of tubing disposed at least partially along the edge, said tubing defining a lumen; and
   wherein a wire disposed in the lumen is inserted through the vessel wall and through the lumen to facilitate placing the flared end through the vessel wall.

13. The method of claim 9 wherein the puncture is created by introducing into the vessel wall a dilating tip in the flared distal end created by the edge and a second edge defined by the aperture.

14. The method of claim 9 wherein the flared distal end does not move relative to the fitting tubular portion.

* * * * *